United States Patent
Agarwal et al.

(10) Patent No.: US 10,130,616 B2
(45) Date of Patent: *Nov. 20, 2018

(54) SECURININE AND NORSECURININE ANALOGUE COMPOUNDS FOR THE TREATMENT OF MYELOID DISORDERS

(71) Applicant: Case Western Reserve University, Cleveland, OH (US)

(72) Inventors: Mukesh Agarwal, Solon, OH (US); David Wald, Shaker Heights, OH (US); Mahesh Gundluru, Lexington, KY (US); Goutam Karan, Lexington, KY (US); Zhiqiang Xia, Lexington, KY (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/026,916

(22) PCT Filed: Oct. 3, 2014

(86) PCT No.: PCT/US2014/059158
§ 371 (c)(1),
(2) Date: Apr. 1, 2016

(87) PCT Pub. No.: WO2015/051317
PCT Pub. Date: Apr. 9, 2015

(65) Prior Publication Data
US 2016/0263089 A1    Sep. 15, 2016

Related U.S. Application Data

(60) Provisional application No. 62/051,595, filed on Sep. 17, 2014, provisional application No. 61/886,448, filed on Oct. 3, 2013.

(51) Int. Cl.
*A61K 31/553* (2006.01)
*A61K 31/407* (2006.01)
*A61K 31/4355* (2006.01)
*A61K 31/437* (2006.01)
*A61K 31/554* (2006.01)
*A61K 45/06* (2006.01)

(52) U.S. Cl.
CPC .......... *A61K 31/437* (2013.01); *A61K 31/407* (2013.01); *A61K 31/553* (2013.01); *A61K 31/554* (2013.01); *A61K 45/06* (2013.01)

(58) Field of Classification Search
None
See application file for complete search history.

(56) References Cited

U.S. PATENT DOCUMENTS

2014/0018383 A1    1/2014  Wald

OTHER PUBLICATIONS

University of Maryland Medical Center. (2016).Web: <http://umm.edu/health/medical/altmed/condition/myeloproliferative-disorders>.*
American Cancer Society. Causes, Risk Factors, and Prevention. Can Acute Lymphocytic Leukemia be prevented? (2014) Web < https://www.cancer.org/cancer/acute-lymphocytic-leukemia/causes-risks-prevention/prevention.html>.*
Gan, Li-She. Organic Letters 8(11) (2006) 2285-2288.*
Gupta, K., et al., "Securinine a Myeloid Differentiation Agent with Therapeutic Potential for AML", PLos ONE, 2011, vol. 6 No. 6, pp. 1-10, Published Jun. 24, 2011, (online journal) [retrieved from internet on Nov. 18, 2014]< URL: http://www.plosone.org/article/info%3Adoi%2F10.1371%2Fjournal.pone.0021203>.

* cited by examiner

*Primary Examiner* — Deepak R Rao
*Assistant Examiner* — Laura M Daniel
(74) *Attorney, Agent, or Firm* — Tarolli, Sundheim, Covell & Tummino LLP

(57) ABSTRACT

The present application relates to securinine or norsecurinine analogs that, when administered to immature myeloid cells, promote differentiation of these cells to mature cells that do not readily proliferate. Therefore, the agents are useful in the treatment of myeloid disorders including myeloproliferative disorders, acute myeloid leukemia, and autoimmune diseases. The agents may also be used as a myeloablative agent in conjunction with a bone marrow transplant or stem cell therapy.

18 Claims, No Drawings

SECURININE AND NORSECURININE ANALOGUE COMPOUNDS FOR THE TREATMENT OF MYELOID DISORDERS

RELATED APPLICATIONS

This application is a national stage filing under 35 U.S.C. § 371 of International Application No. PCT/US2014/059158, filed on Oct. 3, 2014, which claims the benefit of the filing date under 35 U.S.C. § 119(e) to U.S. provisional application 61/886,448, filed Oct. 3, 2013, and to U.S. provisional application 62/051,595, filed Sep. 17, 2014, the entire contents of which are hereby incorporated herein by reference. International Application PCT/US/2014/059158 was published under PCT Article 21(2) in English.

BACKGROUND OF THE INVENTION

Acute Myeloid Leukemia (AML) is one of the most common forms of leukemia in adults and despite advances in treatment, the 5 year survival is still less than 50% in adults and significantly lower in the elderly. In fact, the median survival in patients over the age of 56 is less than one year and only 20% of these patients survive two years. Though the prognosis for younger patients is significantly better, disease-free survival at 6 years following complete remission is still only 40% in children and young adults. There is an enormous unmet need for novel therapeutics to improve the morbidity and mortality of these patients, and for patients suffering from other myeloid disorders. This unmet need is particularly high in the elderly who often cannot tolerate traditional chemotherapy due to toxicities. Though there have been a number of clinical trials, there has been little improvement in overall survival in this age group over the last 30 years.

Acute myeloid leukemia is a broad range of disorders that are all characterized by leukemic cells that have a differentiation arrest. AML can be classified morphologically according to the French-American-British criteria by the degree of differentiation as well as extent of cell maturation as M0-M7. Treatment for all subtypes of AML is very similar, except for acute promyelocytic leukemia (APL, M3 subtype). Traditional therapy involves combination systemic chemotherapy. Several different approaches are utilized. However, these approaches usually involve an induction therapy with cytarabine and a second chemotherapeutic such as daunorubicin or idarubicin and consolidation therapy with either a bone marrow transplant or additional chemotherapy. Besides significant side effects from the traditional chemotherapeutics, the efficacy of these agents in treating AML is poor.

To date the only exception to the poor treatment options for AML is the remarkable success of all-trans-retinoic acid (ATRA) for one relatively uncommon AML subtype (5-10% of AML), acute promyelocytic leukemia (APL). Utilizing a combination of ATRA and chemotherapy, the long term survival and presumed cure of 75-85% of patients is possible. ATRA illustrates the great promise for new agents with greater efficacy and less toxicity. In fact, elderly patients with APL who cannot tolerate traditional chemotherapy can achieve complete remission with therapies that utilize ATRA.

ATRA's success stems from the fact that AML is a clonal disease characterized by the arrest of differentiation of immature myeloid cells. ATRA overcomes this block in differentiation by forcing leukemic cells to terminally differentiate so that they are no longer capable of dividing. ATRA is successful in APL due to its ability to reverse the dominant negative effects of the PML-RAR fusion protein created by a chromosomal translocation, classically t(15;17)(q22;q21). This fusion protein interacts with the retinoid x receptor (RXR), nuclear corepressors and histone deacetylase (HDAC) resulting in repression of transcription that leads to the block in differentiation. At pharmacologic doses, ATRA is able to overcome the repression of transcription and differentiation results. Unfortunately, APL is a rare subtype of AML and ATRA has not been found to be clinically useful for other subtypes. As such, there is a need for compounds that efficiently treat other subtypes of AML and other myeloid disorders.

Though many compounds have been shown to have some differentiation-inducing effects in vitro, their clinical utility has been limited by either suboptimal differentiation-inducing capacity and/or toxicity. For example, Vitamin D3 induces potent differentiation, however, it also causes severe hypercalcemia at the required dose. Treatments that promote the differentiation of immature myeloid cells hold considerable promise in improving the long term survival of AML patients while avoiding some of the toxicities of traditional chemotherapy. Treatment of leukemia could be revolutionized by novel compounds due to their potential to cure leukemia and provide elderly patients with alternative non-toxic regimens.

SUMMARY OF THE INVENTION

Embodiments described herein relate to compounds or therapeutic agents that can be used to treat myeloid disorders, such as myeloid proliferative disorders (e.g., acute myeloid leukemia). In some embodiments, these compounds can include securinine or norsecurinine analogues that, when administered to immature myeloid cells of a subject, can promote differentiation of the immature myeloid cells to more mature cells that do not readily proliferate. The compounds of the disclosure have a high-potency and low toxicity in mammalian subjects and can be used in the treatment of myeloid disorders, such as myeloproliferative disorders, acute myeloid leukemia and autoimmune diseases, and to induce and/or promote differentiation of the myeloid cells. The agents can also be used as a myeloablative agent in conjunction with bone marrow transplantation and stem cell therapies.

One aspect of the present invention provides a method of treating a myeloid disorder in a subject. In some embodiments, the method comprises administering to the subject a therapeutically effective amount of at least one securinine or norsecurinine analogue compound that is sufficient to induce differentiation of the cell. In certain embodiments, the securinine or norsecurinine analogue is a compound of Formula (I), Formula (I'), Formula (II), Formula (III), Formula (IV), or Formula (IV') or compounds 1-7, 9, 11, 13-73, 75-88, 90-97, or 99-112 or pharmaceutically acceptable salts thereof.

In some embodiments, the securinine or norsecurinine analogue of Formula (I) is selected from the group consisting of compounds 1, 2, 11, 13, or 14 or pharmaceutically acceptable salts thereof.

In other embodiments, the securinine or norsecurinine analogue of Formula (I') is compound 9 or pharmaceutically acceptable salts thereof.

In certain embodiments, the securinine or norsecurinine analogue of Formula (II) is selected from the group consisting of compounds 3-7 or pharmaceutically acceptable salts thereof.

In some embodiments, the securinine or norsecurinine analogue of Formula (III) is selected from the group consisting of compounds 15-64 or 101-112 or pharmaceutically acceptable salts thereof.

In other embodiments, the securinine or norsecurinine analogue of Formula (IV) is selected from the group consisting of compounds 65-73, 75-88, 90-97, or 99-100 or pharmaceutically acceptable salts thereof.

In certain embodiments, the method of treating a myeloid disorder in a subject comprises administering to the subject a therapeutically effective amount of at least one securinine or norsecurinine analogue of Formula (I), Formula (I'), Formula (II), Formula (III), Formula (IV), or Formula (IV') or compounds 1-7, 9, 11, 13-73, 75-88, 90-97, or 99-112 or pharmaceutically acceptable salts thereof and an anti-proliferative agent in combination with the securinine or norsecurinine analogue. In other embodiments, the anti-proliferative agent is an anti-metabolite and/or a nucleoside analogue, an alkylating agent, an antibiotic-type agent, a hormonal anticancer agent, an immunological agent, an interferon-type agent, or an antineoplastic agent.

In some embodiments, the subject with a myeloid disorder is a mammal. In certain embodiments, the mammal is a human.

In certain embodiments, the myeloid disorder is associated with increased proliferation of cells of the myeloid lineage. In other embodiments, the myeloid disorder is leukemia. In some embodiments, the myeloid disorder is a sarcoma. In certain embodiments, the increased proliferation of the cells is reduced following administration of the securinine or norsecurinine analogue.

In other embodiments, the myeloid disorder is associated with reduced differentiation and/or survival of a myeloid cell or a cell of myeloid lineage. In some embodiments, the myeloid disorder is associated with reduced hematopoiesis of cells of the myeloid lineage. In certain embodiments, the myeloid disorder is an autoimmune disease.

In some embodiments, the myeloid disorder is selected from the group consisting of: acute myeloid leukemia (AML), chronic myeloid leukemia (CML), myelodysplastic syndromes (MDS), myelodysplasia, Myelodysplastic Syndrome (e.g., refractory anemia (RA), refractory anemia with ring sideroblasts (RARS), refractory anemia with excess blasts (RAEB), refractory anemia with excess blasts in transformation (RAEBT), and/or chronic myelomonocytic leukemia (CMMoL)), myeloid sarcoma, chloroma, chronic myeloproliferative diseases (CMPD), essential thrombocythemia, polycythemia vera, chronic myelogenous leukemia, myelofibrosis, myelofibrosis with myeloid metaplasia (MMM—also known as agnogenic myeloid metaplasia or idiopathic myelofibrosis), atypical CMD, chronic neutrophilic leukemia, chronic eosinophilic leukemia, systemic mastocytosis, mast cell disease, chronic neutrophilic leukemia (CNL), chronic eosinophilic leukemia (CEL), hypereosinophilic syndrome (HES), unclassified MPD (UMPD), chronic myelomonocytic leukemia (CMML), juvenile myelomonocytic leukemia (JMML), Down Syndrome related myeloid disorders, and myeloid processes that display overlapping features of MDS and CMPD (hybrid CMD).

In certain embodiments, the subject having the myeloid disorder has a mutation in one or more of the following genes: JAK2, NPM1, MPL, RAS, RUNX1, ASXL1, BCORL1, CBL, DNMT3A, EZH2, IDH1/IDH2, TET2, UTX, SF3B1, SRSF2, U2AF35/U2AF1, ZRSR2, PTPN11, SH3KBP1, CDKN2A/B, TRIM33, CTNNA1, SOCS1 and/or SF3B1.

Another aspect of the invention provides a method of inducing differentiation of a cell of the myeloid lineage. In some embodiments, the method comprises administering to the cell an amount of at least one securinine or norsecurinine analogue compound. In certain embodiments, the securinine or norsecurinine analogue is a compound of Formula (I), Formula (I'), Formula (II), Formula (III), Formula (IV), or Formula (IV') or compounds 1-7, 9, 11, 13-73, 75-88, 90-97, or 99-112 or pharmaceutically acceptable salts thereof.

In some embodiments, the securinine or norsecurinine analogue of Formula (I) is selected from the group consisting of compounds 1, 2, 11, 13, or 14 or pharmaceutically acceptable salts thereof.

In other embodiments, the securinine or norsecurinine analogue of Formula (I') is compound 9 or pharmaceutically acceptable salts thereof.

In certain embodiments, the securinine or norsecurinine analogue of Formula (II) is selected from the group consisting of compounds 3-7 or pharmaceutically acceptable salts thereof.

In some embodiments, the securinine or norsecurinine analogue of Formula (III) is selected from the group consisting of compounds 15-64 or 101-112 or pharmaceutically acceptable salts thereof.

In other embodiments, the securinine or norsecurinine analogue of Formula (IV) is selected from the group consisting of compounds 65-73, 75-88, 90-97, or 99-100 or pharmaceutically acceptable salts thereof.

In certain embodiments, the method of inducing differentiation of a cell of the myeloid lineage comprises administering to the subject a therapeutically effective amount of at least one securinine or norsecurinine analogue of Formula (I), Formula (I'), Formula (II), Formula (III), Formula (IV), or Formula (IV') or compounds 1-7, 9, 11, 13-73, 75-88, 90-97, or 99-112 or pharmaceutically acceptable salts thereof and an anti-proliferative agent in combination with the securinine or norsecurinine analogue. In other embodiments, the anti-proliferative agent is an anti-metabolite and/or a nucleoside analogue, an alkylating agent, an antibiotic-type agent, a hormonal anticancer agent, an immunological agent, an interferon-type agent, or an antineoplastic agent.

In certain embodiments, the cell of the myeloid lineage is in a subject. In some embodiments, the subject is a mammal. In certain embodiments, the mammal is a human.

In other embodiments, the cell is a common myeloid progenitor cell, myeloblast, megakaryoblast, proerythroblast, monoblast, promegakaryocyte, megakaryocyte, basophilic erythroblast, polychromatic erythroblast, orthochromatic erythroblast (normoblast), polychromatic erythrocyte, promonocyte, monocyte, or any one of a basophilic/neutrophilic/eosinophilic precursor cells.

In certain embodiments, the cell of the myeloid lineage is a cancer cell. In some embodiments, the cancer cell is a leukemic cell or sarcoma cell.

DETAILED DESCRIPTION OF THE INVENTION

Definitions

In order that the invention described herein may be fully understood, the following detailed description is set forth.

Unless defined otherwise, all technical and scientific terms used herein have the same meaning as those commonly understood by one of ordinary skill in the art to which this invention belongs. Although methods and materials similar or equivalent to those described herein can be used in the practice or testing of the present invention, suitable methods and materials are described below. The materials, methods and examples are illustrative only, and are not intended to be limiting. All publications, patents and other documents mentioned herein are incorporated by reference in their entirety.

Each embodiment of the invention described herein may be taken alone or in combination with one or more other embodiments of the invention.

Throughout this specification, the word "a" will be understood to imply the inclusion of one or more of the integers modified by the article "a."

Throughout this specification, the word "comprise" or variations such as "comprises" or "comprising" will be understood to imply the inclusion of a stated integer or groups of integers but not the exclusion of any other integer or group of integers.

The term "or" as used herein should be understood to mean "and/or", unless the context clearly indicates otherwise.

"Myeloid disorder" means any disease, disorder or condition associated with aberrant proliferation, differentiation and/or survival of a cell of the myeloid lineage (e.g., a common myeloid progenitor cell). In some embodiments, the myeloid disorder is associated with increased proliferation of a cell of the myeloid lineage (e.g., myeloid leukemia). In some embodiments, the myeloid disorder is associated with reduced differentiation and/or survival of a myeloid cell or a cell of myeloid lineage. In some embodiments, the myeloid disorder is associated with reduced hematopoiesis of cells of the myeloid lineage. In some embodiments, the myeloid disorder is an autoimmune disease. Examples of myeloid disorders include, but are not limited to, any one of: acute myeloid leukemia (AML), chronic myeloid leukemia (CML), myelodysplastic syndromes (MDS), myelodysplasia, Myelodysplastic Syndrome (e.g., refractory anemia (RA), refractory anemia with ring sideroblasts (RARS), refractory anemia with excess blasts (RAEB), refractory anemia with excess blasts in transformation (RAEBT), and/or chronic myelomonocytic leukemia (CMMoL)), myeloid sarcoma, chloroma, chronic myeloproliferative diseases (CMPD), essential thrombocythemia, polycythemia vera, chronic myelogenous leukemia, myelofibrosis, myelofibrosis with myeloid metaplasia (MMM—also known as agnogenic myeloid metaplasia or idiopathic myelofibrosis), atypical CMD, chronic neutrophilic leukemia, chronic eosinophilic leukemia, systemic mastocytosis, mast cell disease, chronic neutrophilic leukemia (CNL), chronic eosinophilic leukemia (CEL), hypereosinophilic syndrome (HES), unclassified MPD (UMPD), chronic myelomonocytic leukemia (CMML), juvenile myelomonocytic leukemia (JMML), Down Syndrome related myeloid disorders, and myeloid processes that display overlapping features of MDS and CMPD (hybrid CMD). In some embodiments, a subject having a myeloid disorder has a mutation in one or more of the following genes: JAK2, NPM1, MPL, RAS, RUNX1, ASXL1, BCORL1, CBL, DNMT3A, EZH2, IDH1/IDH2, TET2, UTX, SF3B1, SRSF2, U2AF35/U2AF1, ZRSR2, PTPN11, SH3KBP1, CDKN2A/B, TRIM33, CTNNA1, SOCS1 and/or SF3B1. In some embodiments, a myeloid disorder is any of the myeloid disorders described in Murati et al., 2012, BMC Cancer, 12:304.

A cell of the myeloid lineage includes common myeloid progenitor cells and any cell derived from a common myeloid progenitor cell. In some embodiments, a cell of the myeloid lineage is one or more of the following: a common myeloid progenitor cell, megakaryoblast, promegakaryocyte, megakaryocyte, proerythroblast (pronormoblast), basophilic erythroblast, polychromatic erythroblast, orthochromatic erythroblast (normoblast), polychromatic erythrocyte (reticulocyte), monoblast, promonocyte, monocyte, or any basophil/neutrophil/eosinophil precursor cells (e.g., promyelocyte, myelocyte, metamyelocyte or band). In some embodiments, a cell of the myeloid lineage is selected from the group consisting of: a thrombocyte, erythrocyte, mast cell, basophil, neutrophil, eosinophil, macrophage, and myeloid dendritic cell. In some embodiments, a cell of the myeloid lineage is a tumor cell. In some embodiments, a cell of the myeloid lineage is a cancer cell. In some embodiments, the cell of the myeloid lineage is a leukemic cell. In some embodiments, the cell is a myeloid sarcoma cell.

The term "securinine" refers to the compound (6S,11aR,11bS)-9,10,11,11a-tetrahydro-8H-6,11b-methanofuro[2,3-c]pyrido[1,2-a]azepin-2(6H)-one, with a molecular formula of $C_{13}H_{15}NO_2$, a molecular weight of 217.2637, and a CAS Registry Number of 5610-40-2.

The term "norsecurinine" refers to the compound ((6S,10aR,10bS)-8,9,10,10a-tetrahydro-6,10b-methanofuro[2,3-c]pyrrolo[1,2-a]azepin-2(6H)-one, with a molecular formula of $C_{12}H_{13}NO_2$, a molecular weight of 203.2371, and a CAS Registry Number of 2650-35-3.

The terms "securinine analogues" or "norsecurinine analogues" refer to chemical compounds that are structurally similar to securinine or norsecurinine but differ slightly in composition (as in the replacement of one atom by an atom of a different element or in the presence of a particular functional group, or the replacement of one functional group by another functional group). Thus, a securinine analogue or a norsecurinine analogue is a compound that is similar or comparable in function and appearance to securinine or nonsecurinine, but not in structure or origin to the reference compound. The term "securinine analogue" can include analogues of norsecurinine.

It will be noted that the structure of some of the compounds of the application include asymmetric (chiral) carbon or sulfur atoms. It is to be understood accordingly that the isomers arising from such asymmetry are included herein, unless indicated otherwise. Such isomers can be obtained in substantially pure form by classical separation techniques and by stereochemically controlled synthesis. The compounds of this application may exist in stereoisomeric form, and therefore can be produced as individual stereoisomers or as mixtures. Compounds of the present application containing one or multiple asymmetrically substituted atoms may be isolated in optically active or racemic forms. It is well known in the art how to prepare optically active forms, such as by resolution of racemic forms, by synthesis from optically active starting materials, or by synthesis using optically active reagents.

In certain embodiments, compounds of the application may be racemic. In certain embodiments, compounds of the application may be enriched in one enantiomer. For example, a compound of the application may have greater than 30% ee, 40% ee, 50% ee, 60% ee, 70% ee, 80% ee, 90% ee, or even 95% or greater ee.

In certain embodiments, the therapeutic preparation may be enriched to provide predominantly one enantiomer of a compound (e.g., of formula (I) or (II)). An enantiomerically enriched mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, compounds of the application may have more than one stereocenter. In certain such embodiments, compounds of the application may be enriched in one or more diastereomer. For example, a compound of the application may have greater than 30% de, 40% de, 50% de, 60% de, 70% de, 80% de, 90% de, or even 95% or greater de.

In certain embodiments, the therapeutic preparation may be enriched to provide predominantly one diastereomer of a compound (e.g., of Formula (I) or (II)). A diastereomerically enriched mixture may comprise, for example, at least 60 mol percent of one diastereomer, or more preferably at least 75, 90, 95, or even 99 mol percent.

The term "isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center" whereas a sulfur bound to three or four different substitutents, e.g. sulfoxides or sulfinimides, is likewise termed a "chiral center".

The term "chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has 2n−1 enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Alternatively, when one or more chiral centers are present, a stereoisomer may be characterized as (+) or (−). Absolute configuration refers to the arrangement in space of the substituents attached to the chiral center. The substituents attached to the chiral center under consideration are ranked in accordance with the Sequence Rule of Cahn, Ingold and Prelog (Cahn et al., Angew. Chem. Inter. Edit. 1966, 5, 385; errata 511; Cahn et al., Angew. Chem. 1966, 78, 413; Cahn and Ingold, J. Chem. Soc. 1951 (London), 612; Cahn et al., Experientia 1956, 12, 81; Cahn, J., Chem. Educ. 1964, 41, 116).

The term "geometric isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules. Further, the structures and other compounds discussed in this application include all atropic and geometric isomers thereof.

The term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "derivative" refers to compounds that have a common core structure, and are substituted with various groups as described herein.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 1996, 96, 3147-3176.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile. Lists of salts are found in Remington's Pharmaceutical Sciences, 18th ed. (Mack Publishing Company, 1990). In certain embodiments, contemplated salts of the compounds include, but are not limited to, alkyl, dialkyl, trialkyl or tetra-alkyl ammonium salts. In certain embodiments, contemplated salts of compounds include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, trimethamine, and zinc salts. In certain embodiments, contemplated salts of compounds include, but are not limited to, Na, Ca, K, Mg, Zn or other metal salts.

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl)N-Mannich bases, Schiff bases and enaminones of amino functional groups, oximes, acetals, ketals and enol esters of ketone and aldehyde functional groups, and the like, See Bundegaard, H. "Design of Prodrugs" p 1-92, Elesevier, New York-Oxford (1985).

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

The term "analogue" refers to a chemical compound that is structurally similar to another but differs slightly in composition (as in the replacement of one atom by an atom of a different element or in the presence of a particular functional group, or the replacement of one functional group by another functional group). Thus, an analogue is a compound that is similar or comparable in function and appearance, but not in structure or origin to the reference compound.

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2.sup.nd ed. 1991); Harrison and Harrison et al., Compendium of Synthetic Organic Methods, Vols. 1-8 (John Wiley and Sons, 1971-1996); and Kocienski, Protecting Groups, (Verlag, $3^{rd}$ ed. 2003).

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), it is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and in some embodiments, aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The term "alkyl" refers to a linear, branched or cyclic hydrocarbon group of 1 to about 24 carbon atoms is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "substituted alkyl" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" or a "heteroaralkyl" moiety is an alkyl substituted with an aryl or heteroaryl group (e.g., phenylmethyl (benzyl)). If not otherwise indicated, the terms "alkyl" and "lower alkyl" include linear, branched, cyclic, unsubstituted, substituted, and/or heteroatom-containing alkyl or lower alkyl, respectively.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, or having 5 to 8 carbon atoms.

The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocylcohexenyl) in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The terms "alkyl", "alkenyl", and "alkynyl" are intended to include moieties which are diradicals, i.e., having two points of attachment. A nonlimiting example of such an alkyl moiety that is a diradical is —$CH_2CH_2$—, i.e., a $C_2$ alkyl group that is covalently bonded via each terminal carbon atom to the remainder of the molecule.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. In some embodiments, substituents identified as "$C_1$-$C_6$ alkoxy" or "lower alkoxy" herein contain 1 to 3 carbon atoms, and in particular embodiments, such substituents contain 1 or 2 carbon atoms (i.e., methoxy and ethoxy).

The term "alkoxyalkyl" refers to an alkyl group substituted with an alkoxy group and may be represented by the general formula alkyl-O-alkyl.

The term "alkylamino", as used herein, refers to an amino group substituted with at least one alkyl group.

The terms "alkylthio" or "alkylsulfanyl" as used herein, refer to a thiol group substituted with an alkyl group and may be represented by the general formula alkylS—.

The term "amide", as used herein, refers to a group

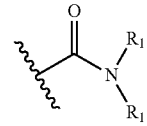

wherein each $R_1$ independently represent a hydrogen or hydrocarbyl group, or two $R_1$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

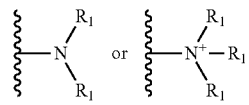

wherein each $R_1$ independently represents a hydrogen or a hydrocarbyl group, or two $R_1$ are taken together with the N atom to which they are attached complete a heterocycle having from 4 to 8 atoms in the ring structure.

The term "aminoalkyl", as used herein, refers to an alkyl group substituted with an amino group.

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and in some embodiments, aryl groups can contain 5 to 14 carbon atoms. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diaryl amino, and alkylaryl amino), acylamino (including alkylcarbonylamino, arylcarbonylamino, carbamoyl and ureido), amidino, imino, sulfhydryl, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl). If not otherwise indicated, the term "aryl" includes unsubstituted, substituted, and/or heteroatom-containing aromatic substituents.

The term "azido" is art-recognized and refers to the group —N=N+=N−.

The term "carbamate" is art-recognized and refers to a group

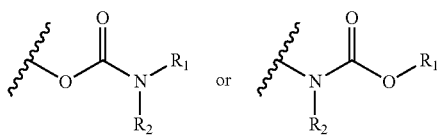

wherein $R_1$ and $R_2$ independently represent hydrogen or a hydrocarbyl group, such as an alkyl group, or $R_1$ and $R_2$ taken together with the intervening atom(s) complete a heterocycle having from 4 to 8 atoms in the ring structure.

The term carbamoyl is art-recognized and refers to the group represented by —(CO)—NH$_2$.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "cycloalkyl alkyl", as used herein, refers to an alkyl group substituted with a cycloalkyl group.

The term "carbonate" is art-recognized and refers to a group —OCO$_2$—R$_1$, wherein R$_1$ represents a hydrocarbyl group.

The term "carboxy", as used herein, refers to a group represented by the formula —CO$_2$H.

The term "cyano" is art-recognized and refers to the group —CN.

The term "cyanato" is art-recognized and refers to the group —O—CN.

The term "ester", as used herein, refers to a group —C(O)OR$_1$ wherein R$_1$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The term "formyl" is art-recognized and refers the group —(CO)—H.

The terms "hetaralkyl" and "heteroaralkyl", as used herein, refers to an alkyl group substituted with a hetaryl group.

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

Heterocyclyl groups can be saturated or unsaturated and include pyrrolidine, oxolane, thiolane, piperidine, piperazine, morpholine, lactones, lactams, such as azetidinones and pyrrolidinones, sultams, and sultones. Heterocyclic groups such as pyrrole and furan can have aromatic character. They include fused ring structures, such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —CF$_3$, or —CN, or the like.

The term "halo" or "halogen" refers to fluoro, chloro, bromo, and iodo. "Counterion" is used to represent a small, negatively charged species such as fluoride, chloride, bromide, iodide, hydroxide, acetate, and sulfate.

The term "imino" is art-recognized and refers to the group represented by —CR$_1$=NH, wherein R$_1$ is selected from the group comprising hydrogen or hydrocarbyl.

The term "isocyanato" is art-recognized and refers to the group —O—N$^+$=C$^-$.

The term "isocyano" is art-recognized and refers to the group —N$^+$ C$^-$.

The term "isothiocyanato" is art-recognized and refers to the group —S—CN.

The term "nitro" is art-recognized and refers to the group represented by —NO$_2$.

The term "nitroso" is art-recognized and refers to the group represented by —NO.

The term "phosphono" is art-recognized and refers to the group represented by —P(O)(OH)$_2$.

The term "phosphonato" is art-recognized and refers to the group represented by —P(O)(O$^-$)$_2$.

The term "phosphinato" is art-recognized and refers to the group represented by —P(O)(O$^-$)$_2$.

The term "phospho" is art-recognized and refers to the group represented by —PO$_2$.

The term "phosphino" is art-recognized and refers to the group represented by —PH$_2$.

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The terms "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as alkyl, alkenyl, alkynyl, aryl, heteroaryl, cycloalkyl, heterocyclyl, alkaryl, aralkyl, halo, hydroxyl, silyl, sulfhydryl, alkoxy, alkenyloxy, alkynyloxy, aryloxy, acyl, acyloxy, alkoxycarbonyl, aryloxycarbonyl, alkylcarbonato, arylcarbonato, carboxy, carboxylato, carbamoyl, thiocarbamoyl, carbamido, cyano, isocyano, cyanato, isocyanato, isothiocyanato, azido, formyl, thioformyl, amino, alkylamido, imino, nitro, nitroso, sulfo, sulfonato, alkylsulfanyl, arylsulfanyl, alkylsulfinyl, arylsulfinyl, alkylsulfonyl, arylsulfonyl, phosphono, phosphonato, phosphinato, phospho, and phosphino.

The term "sulfonamide" is art-recognized and refers to the group represented by the general formulae

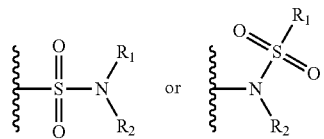

wherein R$_1$ and R$_2$ independently represents hydrogen or hydrocarbyl, such as alkyl, or R$_1$ and R$_2$ taken together with the intervening atom(s) complete a heterocycle having from 4 to 8 atoms in the ring structure.

The terms "sulfoxide" or "alkylsulfinyl" are art-recognized and refer to the group —S(O)—R$_1$, wherein R$_1$ represents a hydrocarbyl.

The terms "sulfonate" or "sulfo" are art-recognized and refer to the group SO$_3$H, or a pharmaceutically acceptable salt thereof.

The terms "sulfone" or "alkylsulfonyl" are art-recognized and refer to the group —S(O)$_2$—R$_1$, wherein R$_1$ represents a hydrocarbyl.

The term "thioalkyl", as used herein, refers to an alkyl group substituted with a thiol group.

The term "thiocarbamoyl" is art-recognized and refers to the group —(CS)—NH$_2$.

The term "thioester", as used herein, refers to a group —C(O)SR$_1$ or —SC(O)R$_1$ wherein R$_1$ represents a hydrocarbyl.

The term "thioether", as used herein, is equivalent to an ether, wherein the oxygen is replaced with a sulfur.

The term "urea" is art-recognized and may be represented by the general formula

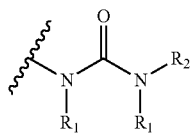

wherein $R_1$ and $R_2$ independently represent hydrogen or a hydrocarbyl, such as alkyl, or either occurrence of $R_1$ taken together with $R_2$ and the intervening atom(s) complete a heterocycle having from 4 to 8 atoms in the ring structure.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The term "stability," "stable," "stable compound," or "stable structure" in the context of a chemical structure refers to the chemical state when a system is in its lowest energy state, or in chemical equilibrium with its environment. Thus, a stable compound (or, e.g., a compound containing a number of atoms or substitutions that are stable) is not particularly reactive in the environment or during normal use, and retains its useful properties on the timescale of its expected usefulness. A stable compound is sufficiently robust to survive isolation, and as appropriate, purification from a reaction mixture, and formulation into an efficacious therapeutic agent.

The terms "free compound" is used herein to describe a compound in the unbound state.

Throughout the description, where compositions are described as having, including, or comprising, specific components, it is contemplated that compositions also may consist essentially of, or consist of, the recited components. Similarly, where methods or processes are described as having, including, or comprising specific process steps, the processes also may consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "small molecule" is an art-recognized term. In certain embodiments, this term refers to a molecule, which has a molecular weight of less than about 2000 amu, or less than about 1000 amu, and even less than about 500 amu.

All percentages and ratios used herein, unless otherwise indicated, are by weight.

The term "ED50" is art-recognized. In certain embodiments, ED50 means the dose of a drug, which produces 50% of its maximum response or effect, or alternatively, the dose, which produces a pre-determined response in 50% of test subjects or preparations. The term "LD50" is art-recognized. In certain embodiments, LD50 means the dose of a drug, which is lethal in 50% of test subjects. The term "therapeutic index" is an art-recognized term, which refers to the therapeutic index of a drug, defined as LD50/ED50.

The terms "$IC_{50}$," or "half maximal inhibitory concentration" is intended to refer to the concentration of a substance (e.g., a compound or a drug) that is required for 50% inhibition of a biological process, or component of a process, including a protein, subunit, organelle, ribonucleoprotein, etc.

The terms "healthy" and "normal" are used interchangeably herein to refer to a subject or particular cell or tissue that is devoid (at least to the limit of detection) of a disease condition.

Securinine and Norsecurinine Analogues

Embodiments described herein relate to compounds or therapeutic agents that, in some embodiments, can be used to induce and/or promote differentiation of immature myeloid cells as well as to methods and assays of identifying therapeutic agents or compounds capable of inducing differentiation of immature myeloid cells. Agents in accordance with the invention have a high-potency and low toxicity in mammalian subjects and can be used in the treatment of myeloid disorders, such as myeloproliferative disorders, acute myeloid leukemia and auto immune disease. The agents can also be used as a myeloablative agent in conjunction with bone marrow transplantation and stem cell therapies.

The agents in accordance with the present invention can be used alone or in combination with other differentiation inducing agents, anti-proliferative agents, and/or chemotherapeutic agents for the treatment of proliferative and/or other neoplastic disorders.

In some embodiments, the securinine analogue and norsecurinine analogue compounds can include compounds that when administered to immature myeloid cells of a subject can promote differentiation of the immature myeloid cells to more mature cells that do not readily proliferate. The securinine and norsecurinine analogues can be identified using the nitroblue tetrazolium (NBT) reduction assay described herein.

In some embodiments, the securinine and norsecurinine analogues are represented by general Formula (I):

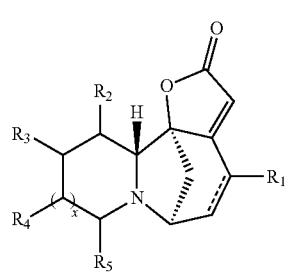

Formula (I)

or pharmaceutically acceptable salts thereof, wherein as valence and stability permit:

═══ represents a single or double bond;

x is 0 or 1;

$R_1$ is hydrogen or substituted or unsubstituted alkyl, alkenyl, alkynyl, aryl, heteroaryl, cycloalkyl, heterocyclyl, cycloalkylalkyl, heterocyclylalkyl, heteroaralkyl, aralkyl, halo, silyl, hydroxyl, sulfhydryl, alkoxy, alkenyloxy, alkynyloxy, alkoxyalkyl, alkoxyalkenyl, aryloxy, acyl, alkylcarbonato, arylcarbonato, carboxy, carboxylato, carbamoyl, alkylcarbamoyl, arylcarbamoyl, thiocarbamoyl, carbamido, cyano, isocyano, cyanato, isocyanato, isothiocyanato, azido, formyl, thioformyl, amino, alkylamino, arylamino, cycloalkylamino, heterocyclylamino, cycloalkylalkylamino, arylalkylamino, heteroarylalkylamino, aminoalkyl, imino, nitro, nitroso, sulfo, sulfonato, alkylsulfanyl, arylsulfanyl, cycloalkylsulfanyl, heterocyclylsulfanyl, heteroarylsulfanyl, amidoalkylsulfanyl, arylalkysulfanyl, heteroarylalkylsulfanyl, alkylsulfinyl, arylsulfinyl, alkylsulfonyl, arylsulfonyl, phosphono, phosphonato, phosphinato, phospho, phosphino, thioalkyl, or thioaryl;

$R_2$, $R_3$, $R_4$, and $R_5$ are each independently hydrogen or substituted or unsubstituted alkyl, alkenyl, alkynyl, aryl, heteroaryl, cycloalkyl, heterocyclyl, cycloalkylalkyl, heterocyclylalkyl, heteroaralkyl, aralkyl, halo, silyl, hydroxyl, sulfhydryl, alkoxy, alkenyloxy, alkynyloxy, alkoxyalkyl, alkoxyalkenyl, aryloxy, acyl, alkylcarbonato, arylcarbonato, carboxy, carboxylato, carbamoyl, alkylcarbamoyl, arylcarbamoyl, thiocarbamoyl, carbamido, cyano, isocyano, cyanato, isocyanato, isothiocyanato, azido, formyl, thioformyl, amino, alkylamino, arylamino, cycloalkylamino, heterocyclylamino, cycloalkylalkylamino, arylalkylamino, heteroarylalkylamino, aminoalkyl, imino, nitro, nitroso, sulfo, sulfonato, alkylsulfanyl, arylsulfanyl, cycloalkylsulfanyl, heterocyclylsulfanyl, heteroarylsulfanyl, amidoalkylsulfanyl, arylalkysulfanyl, heteroarylalkylsulfanyl, alkylsulfinyl, arylsulfinyl, alkylsulfonyl, arylsulfonyl, phosphono, phosphonato, phosphinato, phospho, phosphino, thioalkyl, or thioaryl; and wherein adjacent R groups may be linked to form a cyclic or polycyclic ring, wherein the ring is a substituted or unsubstituted aryl, a substituted or unsubstituted heteroaryl, a substituted or unsubstituted cycloalkyl, or a substituted or unsubstituted heterocyclyl.

In certain embodiments, === represents a double bond.

In certain embodiments when x is 1 and === represents a double bond, at least one of $R_1$, $R_2$, $R_3$, $R_4$, and $R_5$ is other than hydrogen.

In certain embodiments, $R_1$ is hydrogen, halogen, or optionally substituted alkyl, aryl, alkenyl, or alkynyl and === represents a double bond.

In certain embodiments, x is 0 and === represents a double bond. In certain such embodiments, $R_5$ is alkoxyalkyl. In certain such embodiments, $R_2$ and $R_3$ are hydrogen.

In certain embodiments, x is 0, $R_5$ is alkoxyalkyl, $R_2$ and $R_3$ are hydrogen, $R_1$ is optionally substituted alkenyl, and === represents a double bond. In certain embodiments, x is 0, $R_5$ is alkoxyalkyl, $R_2$ and $R_3$ are hydrogen, $R_1$ is optionally substituted alkynyl, and === represents a double bond.

In certain embodiments, x is 1. In certain embodiments, x is 1 and === represents a double bond. In certain such embodiments, $R_2$, $R_3$, $R_4$, and $R_5$ are each hydrogen.

In certain embodiments, x is 1, $R_1$ is optionally substituted alkenyl, $R_2$, $R_3$, $R_4$, and $R_5$ are each hydrogen, and === represents a double bond. In certain embodiments, x is 1, $R_1$ is optionally substituted alkynyl, $R_2$, $R_3$, $R_4$, and $R_5$ are each hydrogen, and === represents a double bond.

In certain embodiments, the compound of Formula (I) is selected from:

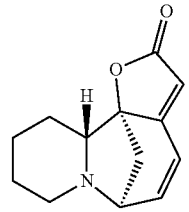

Securinine

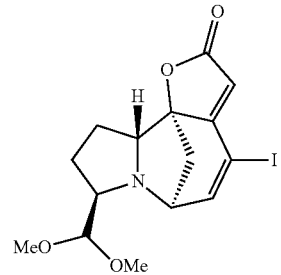

1

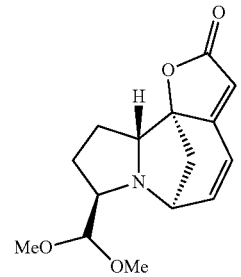

2

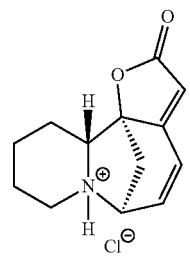

10

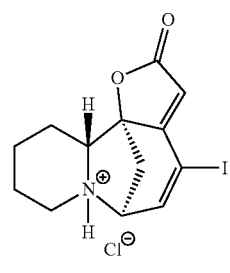

11

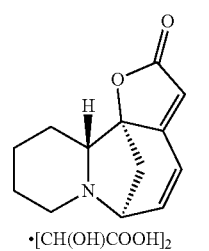

12

-continued

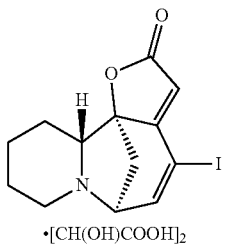

13

·[CH(OH)COOH]₂

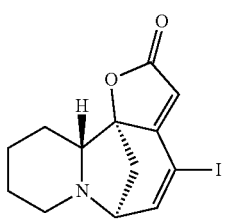

14 or pharmaceutically acceptable salts thereof. For example, the compound is selected from compounds 1, 2, 11, 13, or 14 or pharmaceutically acceptable salts thereof. In some embodiments, the compound is selected from compounds 11, 13, or 14 or pharmaceutically acceptable salts thereof. In other embodiments, the compound is selected from compounds 1 or 2 or pharmaceutically acceptable salts thereof.

In some embodiments, the securinine and norsecurinine analogues are represented by Formula (I'):

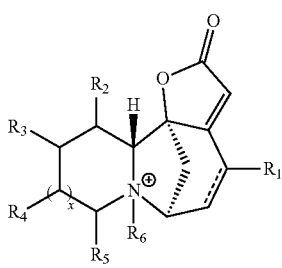

Formula (I')

or pharmaceutically acceptable salts thereof, wherein as valence and stability permit:

=== represents a single or double bond;

x is 0 or 1;

$R_1$ is hydrogen or substituted or unsubstituted alkyl, alkenyl, alkynyl, aryl, heteroaryl, cycloalkyl, heterocyclyl, cycloalkylalkyl, heterocyclylalkyl, heteroaralkyl, aralkyl, halo, silyl, hydroxyl, sulfhydryl, alkoxy, alkenyloxy, alkynyloxy, alkoxyalkyl, alkoxyalkenyl, aryloxy, acyl, alkylcarbonato, arylcarbonato, carboxy, carboxylato, carbamoyl, alkylcarbamoyl, arylcarbamoyl, thiocarbamoyl, carbamido, cyano, isocyano, cyanato, isocyanato, isothiocyanato, azido, formyl, thioformyl, amino, alkylamino, arylamino, cycloalkylamino, heterocyclylamino, cycloalkylalkylamino, arylalkylamino, heteroarylalkylamino, aminoalkyl, imino, nitro, nitroso, sulfo, sulfonato, alkylsulfanyl, arylsulfanyl, cycloalkylsulfanyl, heterocyclylsulfanyl, heteroarylsulfanyl, amidoalkylsulfanyl, arylalkysulfanyl, heteroarylalkylsulfanyl, alkylsulfinyl, arylsulfinyl, alkylsulfonyl, arylsulfonyl, phosphono, phosphonato, phosphinato, phospho, phosphino, thioalkyl, or thioaryl;

$R_2$, $R_3$, $R_4$, and $R_5$ are each independently hydrogen or substituted or unsubstituted alkyl, alkenyl, alkynyl, aryl, heteroaryl, cycloalkyl, heterocyclyl, cycloalkyl alkyl, heterocyclylalkyl, heteroaralkyl, aralkyl, halo, silyl, hydroxyl, sulfhydryl, alkoxy, alkenyloxy, alkynyloxy, alkoxyalkyl, alkoxyalkenyl, aryloxy, acyl, alkylcarbonato, arylcarbonato, carboxy, carboxylato, carbamoyl, alkylcarbamoyl, arylcarbamoyl, thiocarbamoyl, carbamido, cyano, isocyano, cyanato, isocyanato, isothiocyanato, azido, formyl, thioformyl, amino, alkylamino, arylamino, cycloalkylamino, heterocyclylamino, cycloalkylalkylamino, arylalkylamino, heteroarylalkylamino, aminoalkyl, imino, nitro, nitroso, sulfo, sulfonato, alkylsulfanyl, arylsulfanyl, cycloalkylsulfanyl, heterocyclylsulfanyl, heteroarylsulfanyl, amidoalkylsulfanyl, arylalkysulfanyl, heteroarylalkylsulfanyl, alkylsulfinyl, arylsulfinyl, alkylsulfonyl, arylsulfonyl, phosphono, phosphonato, phosphinato, phospho, phosphino, thioalkyl, or thioaryl;

wherein adjacent R groups may be linked to form a cyclic or polycyclic ring, wherein the ring is a substituted or unsubstituted aryl, a substituted or unsubstituted heteroaryl, a substituted or unsubstituted cycloalkyl, or a substituted or unsubstituted heterocyclyl; and wherein $R_6$ is $C_1$-$C_6$ alkyl.

In certain embodiments, === represents a double bond.

In certain embodiments when x is 1 and === represents a double bond, at least one of $R_1$, $R_2$, $R_3$, $R_4$, and $R_5$ is other than hydrogen.

In certain embodiments, $R_1$ is hydrogen, halogen, or optionally substituted alkyl, aryl, alkenyl, or alkynyl and === represents a double bond.

In certain embodiments, x is 0 and === represents a double bond. In certain such embodiments, $R_5$ is alkoxyalkyl. In certain such embodiments, $R_2$ and $R_3$ are hydrogen.

In certain embodiments, x is 0, $R_5$ is alkoxyalkyl, $R_2$ and $R_3$ are hydrogen, $R_1$ is optionally substituted alkenyl, and === represents a double bond. In certain embodiments, x is 0, $R_5$ is alkoxyalkyl, $R_2$ and $R_3$ are hydrogen, $R_1$ is optionally substituted alkynyl, and === represents a double bond.

In certain embodiments, x is 1. In certain embodiments, x is 1 and === represents a double bond. In certain such embodiments, $R_2$, $R_3$, $R_4$, and $R_5$ are each hydrogen.

In certain embodiments, x is 1, $R_1$ is optionally substituted alkenyl, $R_2$, $R_3$, $R_4$, and $R_5$ are each hydrogen, and === represents a double bond. In certain embodiments, x is 1, $R_1$ is optionally substituted alkynyl, $R_2$, $R_3$, $R_4$, and $R_5$ are each hydrogen, and === represents a double bond.

In certain embodiments, the compound of Formula (I') is selected from:

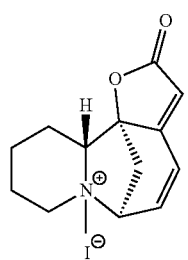

8

-continued

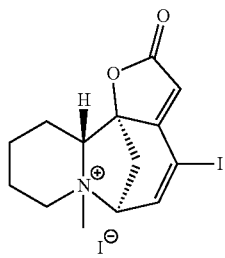

and pharmaceutically acceptable salts thereof. For example, the compound is selected from compound 9 or pharmaceutically acceptable salts thereof.

In some embodiments, the securinine and norsecurinine analogues of Formula (I) are represented by the general Formula (II):

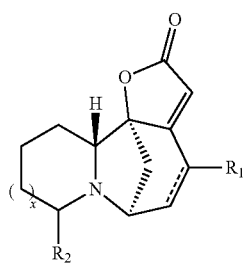

Formula (II)

or pharmaceutically acceptable salts thereof, wherein as valence and stability permit:
=== represents a single or double bond;
x is 0 or 1;
$R_1$ is hydrogen or substituted or unsubstituted alkyl, alkenyl, alkynyl, aryl, heteroaryl, cycloalkyl, heterocyclyl, cycloalkylalkyl, heterocyclylalkyl, heteroaralkyl, aralkyl, halo, silyl, hydroxyl, sulfhydryl, alkoxy, alkenyloxy, alkynyloxy, alkoxyalkyl, alkoxyalkenyl, aryloxy, acyl, alkylcarbonato, arylcarbonato, carboxy, carboxylato, carbamoyl, alkylcarbamoyl, arylcarbamoyl, thiocarbamoyl, carbamido, cyano, isocyano, cyanato, isocyanato, isothiocyanato, azido, formyl, thioformyl, amino, alkylamino, arylamino, cycloalkylamino, heterocyclylamino, cycloalkylalkylamino, arylalkylamino, heteroarylalkylamino, aminoalkyl, imino, nitro, nitroso, sulfo, sulfonato, alkylsulfanyl, arylsulfanyl, cycloalkylsulfanyl, heterocyclylsulfanyl, heteroarylsulfanyl, amidoalkylsulfanyl, arylalkylsulfanyl, heteroarylalkylsulfanyl, alkylsulfinyl, arylsulfinyl, alkylsulfonyl, arylsulfonyl, phosphono, phosphonato, phosphinato, phospho, phosphino, thioalkyl, or thioaryl; and
$R_2$ is hydrogen or substituted or unsubstituted alkyl, alkenyl, alkynyl, aryl, heteroaryl, cycloalkyl, heterocyclyl, cycloalkylalkyl, heterocyclylalkyl, heteroaralkyl, aralkyl, halo, silyl, hydroxyl, sulfhydryl, alkoxy, alkenyloxy, alkynyloxy, alkoxyalkyl, alkoxyalkenyl, aryloxy, acyl, alkylcarbonato, arylcarbonato, carboxy, carboxylato, carbamoyl, alkylcarbamoyl, arylcarbamoyl, thiocarbamoyl, carbamido, cyano, isocyano, cyanato, isocyanato, isothiocyanato, azido, formyl, thioformyl, amino, alkylamino, arylamino, cycloalkylamino, heterocyclylamino, cycloalkylalkylamino, arylalkylamino, heteroarylalkylamino, aminoalkyl, imino, nitro, nitroso, sulfo, sulfonato, alkylsulfanyl, arylsulfanyl, cycloalkylsulfanyl, heterocyclylsulfanyl, heteroarylsulfanyl, amidoalkylsulfanyl, arylalkylsulfanyl, heteroarylalkylsulfanyl, alkylsulfinyl, arylsulfinyl, alkylsulfonyl, arylsulfonyl, phosphono, phosphonato, phosphinato, phospho, phosphino, thioalkyl, or thioaryl.

In certain embodiments, === represents a double bond

In certain embodiments when x is 1 and === represents a double bond, at least one of $R_1$ or $R_2$ is other than hydrogen.

In certain embodiments x is 1 and === represents a double bond. In certain such embodiments, $R_1$ is other than hydrogen and $R_2$ is hydrogen.

In certain embodiments, x is 0 and === represents a double bond. In certain such embodiments, $R_2$ is alkoxyalkyl.

In certain embodiments, $R_1$ is optionally substituted or unsubstituted alkyl, alkenyl, alkynyl, aryl, heteroaryl, cycloalkyl, heterocyclyl or halogen. In certain such embodiments, === represents a double bond.

In certain embodiments, the compound of Formula (II) is selected from:

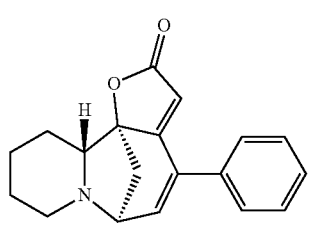

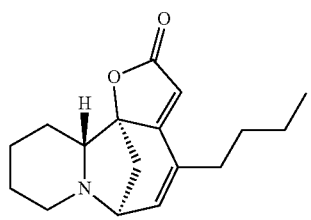

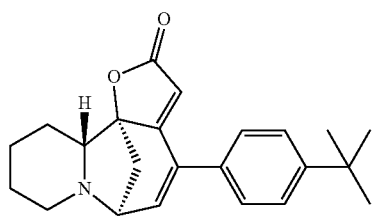

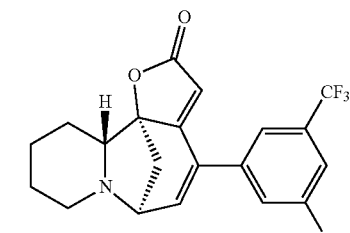

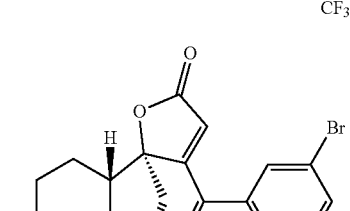

and pharmaceutically acceptable salts thereof.

In some embodiments, the securinine and norsecurinine analogues of Formula (I) and (II) are represented by the general Formula (III):

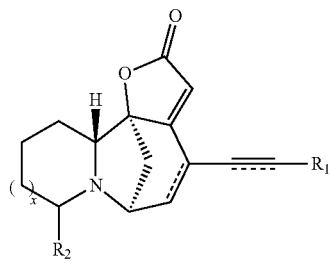

Formula (III)

or pharmaceutically acceptable salts thereof, wherein as valence and stability permit:
=== represents a single or double bond;
≡ represents a double or triple bond;
x is 0 or 1;
$R_1$ is hydrogen or substituted or unsubstituted alkyl, alkenyl, alkynyl, aryl, heteroaryl, cycloalkyl, heterocyclyl, cycloalkylalkyl, heterocyclylalkyl, heteroaralkyl, aralkyl, halo, silyl, hydroxyl, sulfhydryl, alkoxy, alkenyloxy, alkynyloxy, alkoxyalkyl, alkoxyalkenyl, aryloxy, acyl, alkylcarbonato, arylcarbonato, carboxy, carboxylato, carbamoyl, alkylcarbamoyl, arylcarbamoyl, thiocarbamoyl, carbamido, cyano, isocyano, cyanato, isocyanato, isothiocyanato, azido, formyl, thioformyl, amino, alkylamino, arylamino, cycloalkylamino, heterocyclylamino, cycloalkylalkylamino, arylalkylamino, heteroarylalkylamino, aminoalkyl, imino, nitro, nitroso, sulfo, sulfonato, alkylsulfanyl, arylsulfanyl, cycloalkylsulfanyl, heterocyclylsulfanyl, heteroarylsulfanyl, amidoalkylsulfanyl, arylalkysulfanyl, heteroarylalkylsulfanyl, alkylsulfinyl, arylsulfinyl, alkylsulfonyl, arylsulfonyl, phosphono, phosphonato, phosphinato, phospho, phosphino, thioalkyl, or thioaryl; and
$R_2$ is hydrogen or substituted or unsubstituted alkyl, alkenyl, alkynyl, aryl, heteroaryl, cycloalkyl, heterocyclyl, cycloalkylalkyl, heterocyclylalkyl, heteroaralkyl, aralkyl, halo, silyl, hydroxyl, sulfhydryl, alkoxy, alkenyloxy, alkynyloxy, alkoxyalkyl, alkoxyalkenyl, aryloxy, acyl, alkylcarbonato, arylcarbonato, carboxy, carboxylato, carbamoyl, alkylcarbamoyl, arylcarbamoyl, thiocarbamoyl, carbamido, cyano, isocyano, cyanato, isocyanato, isothiocyanato, azido, formyl, thioformyl, amino, alkylamino, arylamino, cycloalkylamino, heterocyclylamino, cycloalkylalkylamino, arylalkylamino, heteroarylalkylamino, aminoalkyl, imino, nitro, nitroso, sulfo, sulfonato, alkylsulfanyl, arylsulfanyl, cycloalkylsulfanyl, heterocyclylsulfanyl, heteroarylsulfanyl, amidoalkylsulfanyl, arylalkysulfanyl, heteroarylalkylsulfanyl, alkylsulfinyl, arylsulfinyl, alkylsulfonyl, arylsulfonyl, phosphono, phosphonato, phosphinato, phospho, phosphino, thioalkyl, or thioaryl.

In certain embodiments, === represents a double bond. In certain such embodiments, ≡ represents a triple bond.

In certain embodiments, ≡ represents a double bond. In certain such embodiments, the double bond has a cis configuration.

In certain embodiments, ≡ represents a double bond. In certain such embodiments, the double bond has a trans configuration.

In certain embodiments, x is 0, === represents a double bond, and ≡ represents a double bond. In certain such embodiments, $R_2$ is alkoxyalkyl.

In certain embodiments, x is 0, === represents a double bond, and represents a triple bond. In certain such embodiments, $R_2$ is alkoxyalkyl.

In certain embodiments, x is 1, === represents a double bond, and represents a double bond. In certain such embodiments, $R_2$ is hydrogen.

In certain embodiments, x is 1, === represents a double bond, and represents a triple bond. In certain such embodiments, $R_2$ is hydrogen.

In certain embodiments, $R_1$ is substituted or unsubstituted alkyl, alkenyl, cycloalkyl, cycloalkylalkyl, heterocyclyl, heterocyclylalkyl, aryl, heteroaryl, alkaryl, aralkyl, heteroaralkyl, hydroxyl, alkoxy, alkoxyalkyl, alkoxyalkylsilyl, alkoxyalkenyl, aryloxyalkyl, or aminoalkyl. In certain such embodiments, === represents a double bond.

In certain embodiments, the compound of Formula (III) is selected from:

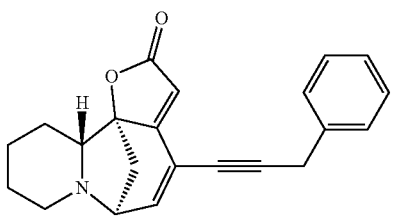

15

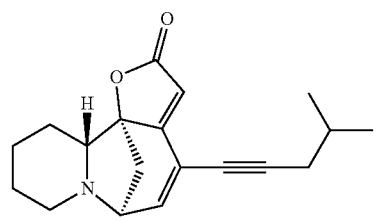

16

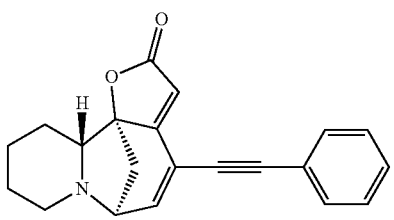

17

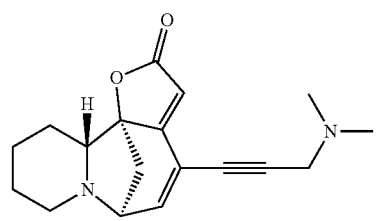

18

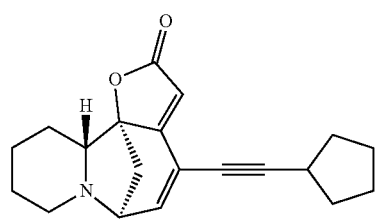

19

27
-continued
20
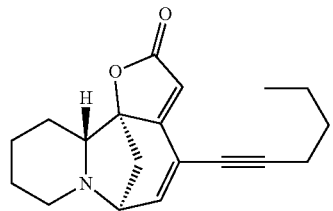
21
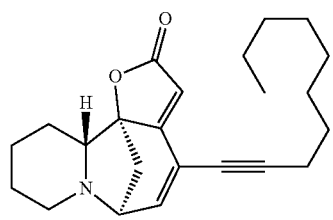
22
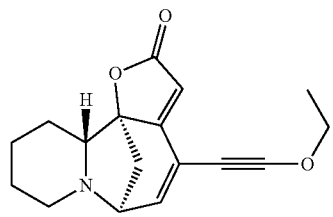
23
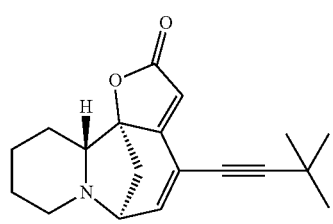
24
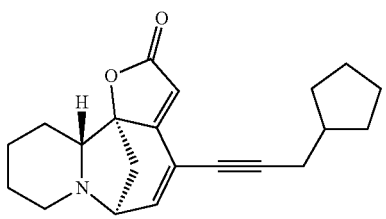
25
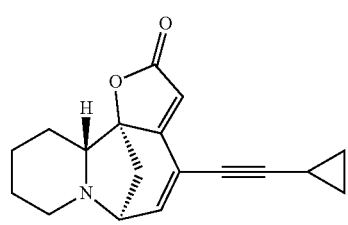
26
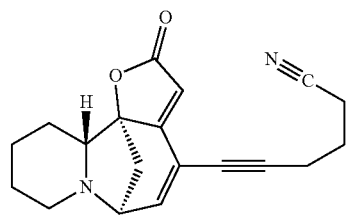
28
-continued
27
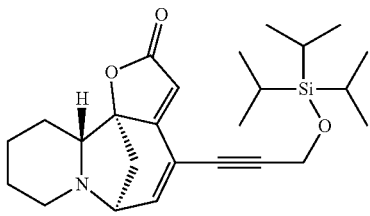
28
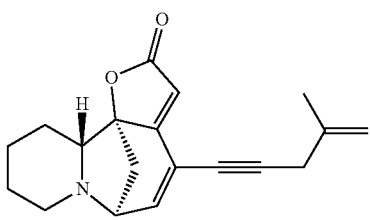
29
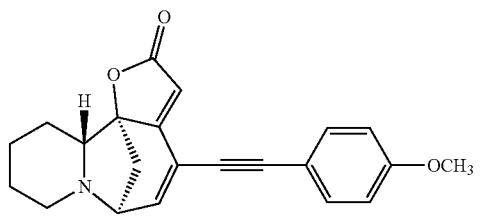
30
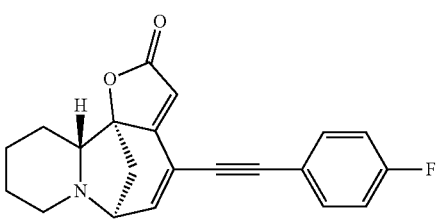
31
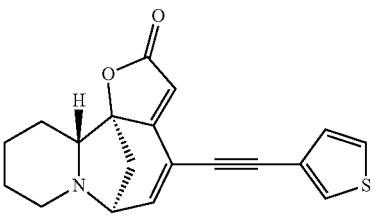
32
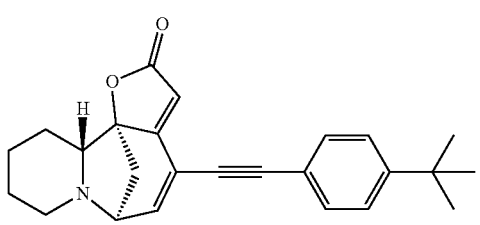
33
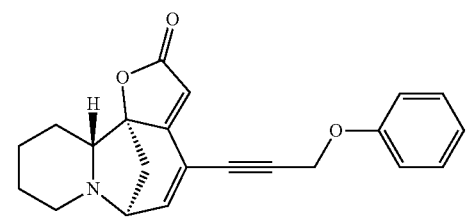

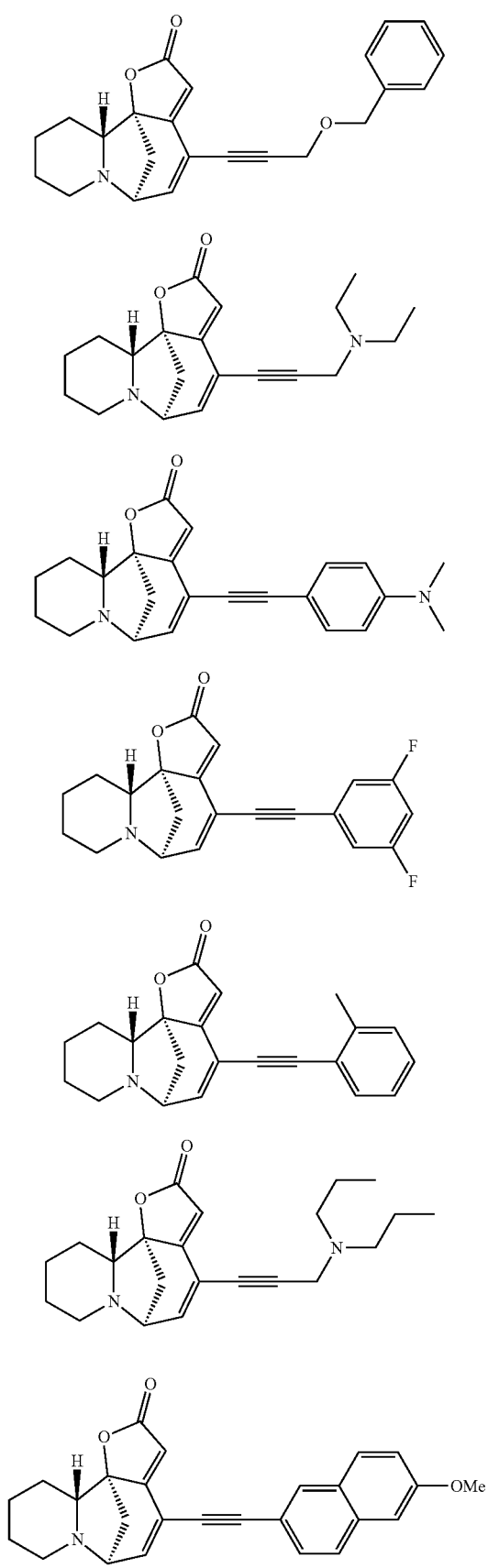
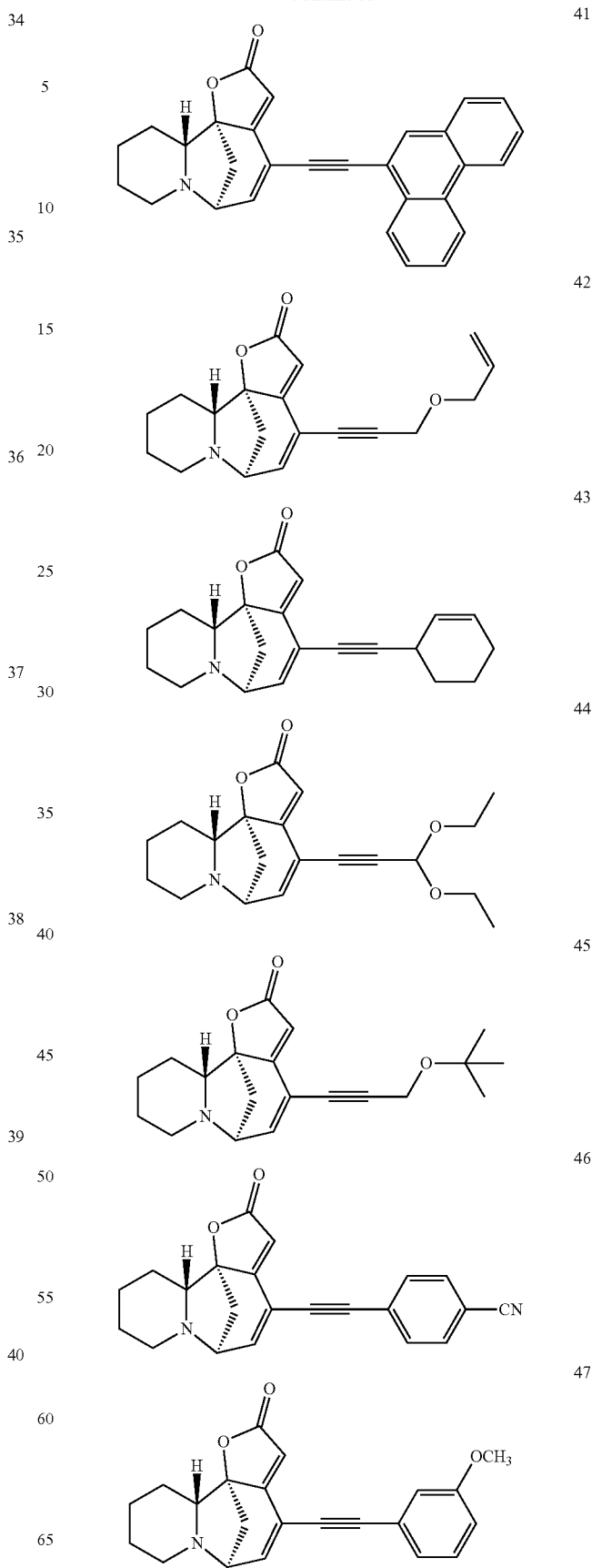

31
-continued
48
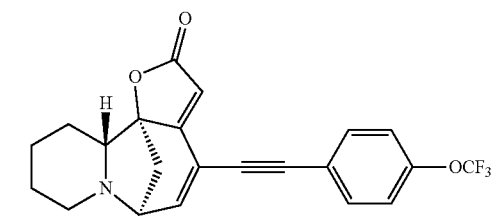
49
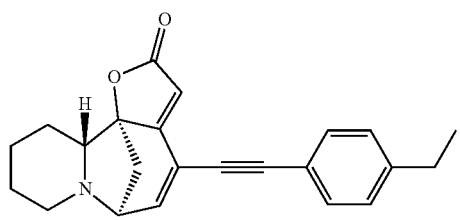
50
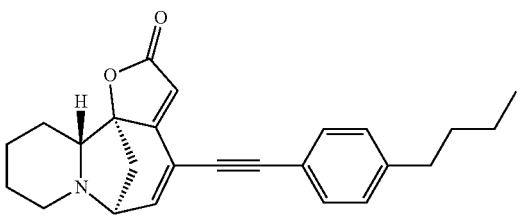
51
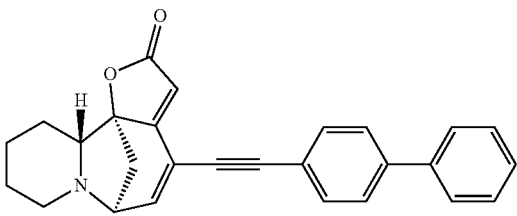
52
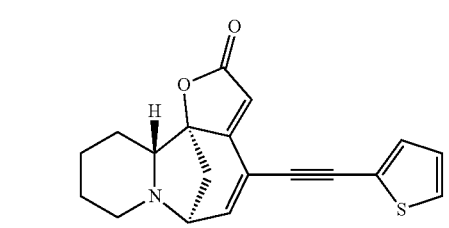
53
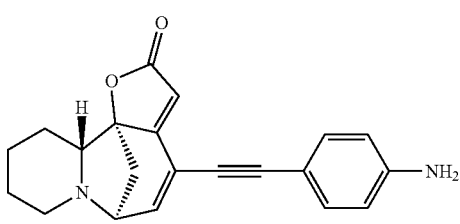
54
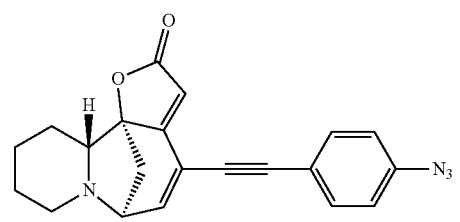
32
-continued
55
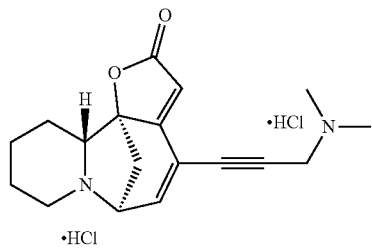
56
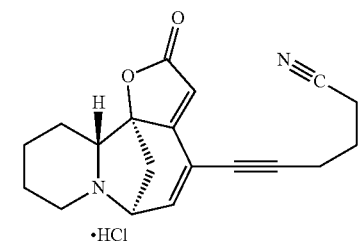
57
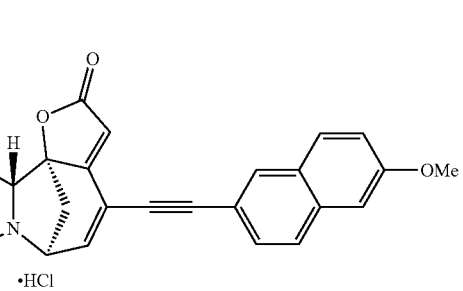
58
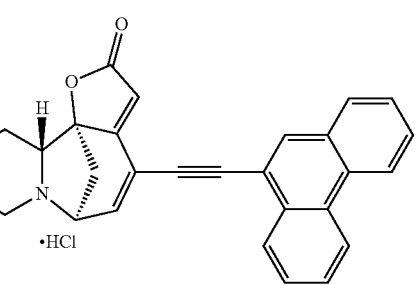
59
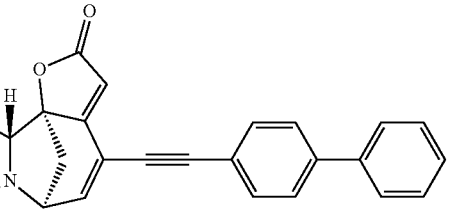
60
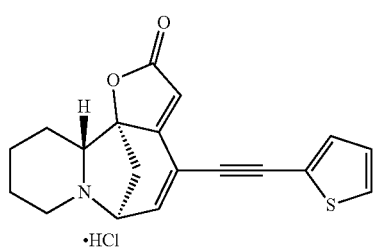

33
-continued
61
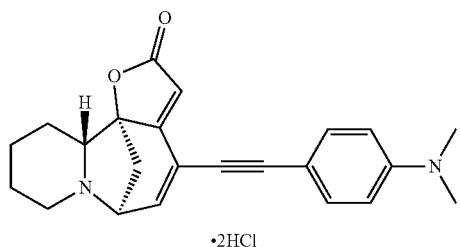
•2HCl
62
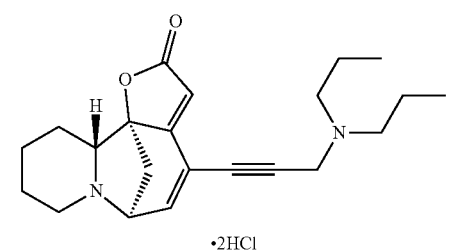
•2HCl
63
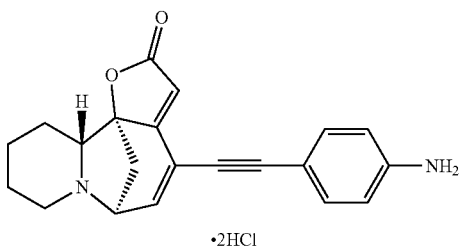
•2HCl
64
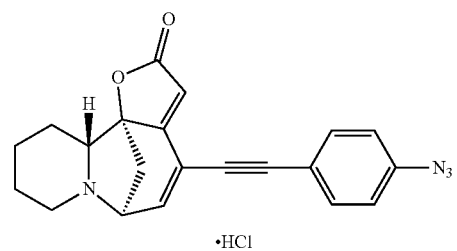
•HCl
101
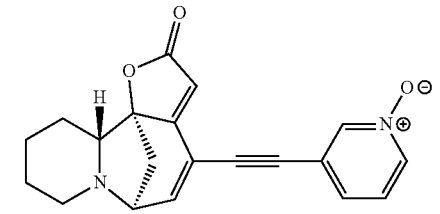
102
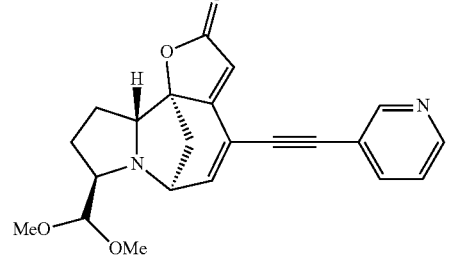
34
-continued
103
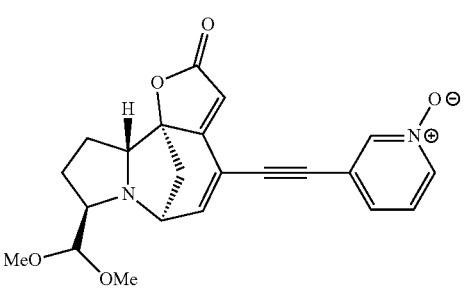
104
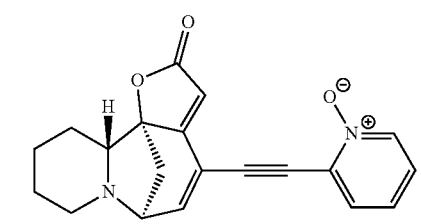
105
106
107
108

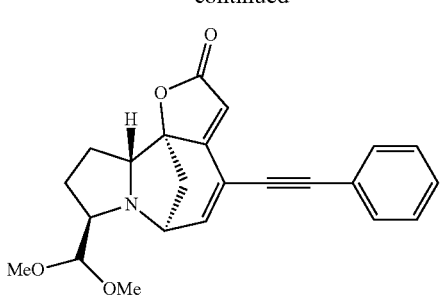

109

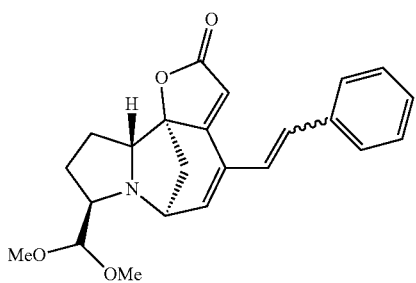

110

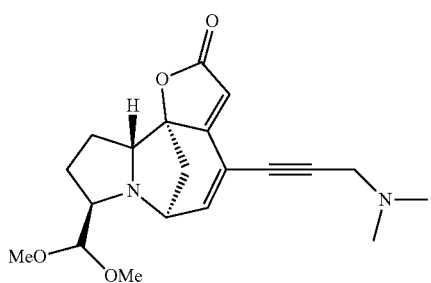

111

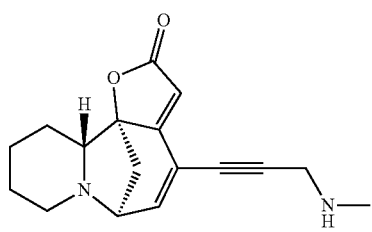

112 or pharmaceutically acceptable salts thereof. For example, the compound is selected from compounds 15-64, 101, 104, 106, or 112 or pharmaceutically acceptable salts thereof. In some embodiments, the compound is selected from compounds 107 or 108 or pharmaceutically acceptable salts thereof. In other embodiments, the compound is selected from compounds 102, 103, 105, 109 or 111 or pharmaceutically acceptable salts thereof. In certain embodiments, the compound is selected from compound 110 or pharmaceutically acceptable salt thereof.

In some embodiments, the securinine analogues are represented by the general Formula (IV):

Formula IV

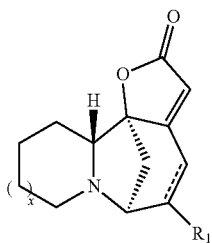

or pharmaceutically acceptable salts thereof, wherein as valence and stability permit:
═══ represents a single or double bond;
x is 0 or 1; and
$R_1$ is hydrogen or substituted or unsubstituted alkyl, alkenyl, alkynyl, aryl, heteroaryl, cycloalkyl, heterocyclyl, cycloalkylalkyl, heterocyclylalkyl, heteroaralkyl, aralkyl, halo, silyl, hydroxyl, sulfhydryl, alkoxy, alkenyloxy, alkynyloxy, alkoxyalkyl, alkoxyalkenyl, aryloxy, acyl, alkylcarbonato, arylcarbonato, carboxy, carboxylato, carbamoyl, alkylcarbamoyl, arylcarbamoyl, thiocarbamoyl, carbamido, cyano, isocyano, cyanato, isocyanato, isothiocyanato, azido, formyl, thioformyl, amino, alkylamino, arylamino, cycloalkylamino, heterocyclylamino, cycloalkylalkylamino, arylalkylamino, heteroarylalkylamino, aminoalkyl, imino, nitro, nitroso, sulfo, sulfonato, alkylsulfanyl, arylsulfanyl, cycloalkylsulfanyl, heterocyclylsulfanyl, heteroarylsulfanyl, amidoalkylsulfanyl, arylalkysulfanyl, heteroarylalkylsulfanyl, alkylsulfinyl, arylsulfinyl, alkylsulfonyl, arylsulfonyl, phosphono, phosphonato, phosphinato, phospho, phosphino, thioalkyl, or thioaryl.

In certain embodiments, ═══ represents a single bond. In certain such embodiments, x is 1.

In certain embodiments wherein $R_1$ is substituted or unsubstituted heterocyclyl, $R_1$ is not fluoro-substituted, such as mono-fluoro substituted pyrrolidine. For example, in certain embodiments wherein $R_1$ is substituted or unsubstituted heterocyclyl, x is 1, and ═══ represents a single bond, $R_1$ is not fluoro-substituted, such as mono-fluoro substituted pyrrolidine. In certain embodiments wherein $R_1$ is substituted or unsubstituted heteroarylalkylamino, $R_1$ is not indolealkylamino. For example, in certain embodiments wherein $R_1$ is substituted or unsubstituted heteroarylalkylamino, x is 1, and ═══ represents a single bond, $R_1$ is not indolealkylamino. In certain embodiments wherein $R_1$ is substituted or unsubstituted arylsulfanyl, $R_1$ is not phenylsulfanyl. For example, in certain embodiments wherein $R_1$ is substituted or unsubstituted arylsulfanyl, x is 1, and ═══ represents a single bond, $R_1$ is not phenylsulfanyl. In certain embodiments wherein $R_1$ is alkylsulfanyl, $R_1$ is not lower alkylsulfanyl, such as propylsulfanyl. For example, in certain embodiments wherein $R_1$ is alkylsulfanyl, x is 1, and ═══ represents a single bond, $R_1$ is not lower alkylsulfanyl, such as propylsulfanyl. In certain embodiments, $R_1$ is hydrogen or substituted or unsubstituted alkyl, alkenyl, alkynyl, aryl, heteroaryl, cycloalkyl, cycloalkylalkyl, heterocyclylalkyl, heteroaralkyl, aralkyl, halo, silyl, hydroxyl, sulfhydryl, alkoxy, alkenyloxy, alkynyloxy, alkoxyalkyl, alkoxyalkenyl, aryloxy, acyl, alkylcarbonato, arylcarbonato, carboxy, carboxylato, carbamoyl, alkylcarbamoyl, arylcarbamoyl, thiocarbamoyl, carbamido, cyano, isocyano, cyanato, isocyanato, isothiocyanato, azido, formyl, thioformyl, amino, alkylamino, arylamino, cycloalkylamino, heterocyclylamino, cycloalkylalkylamino, arylalkylamino, aminoalkyl, imino, nitro, nitroso, sulfo, sulfonato, alkylsulfanyl, cycloalkylsulfanyl, heterocyclylsulfanyl, heteroarylsulfanyl, amidoalkylsulfanyl, arylalkysulfanyl, heteroarylalkylsulfanyl, alkylsulfinyl, arylsulfinyl, arylsulfonyl, phosphono, phosphonato, phosphinato, phospho, phosphino, thioalkyl, or thioaryl. In certain such embodiments, ═══ represents a single bond and x is 1.

In certain embodiments, the compound of Formula (IV) is:
65
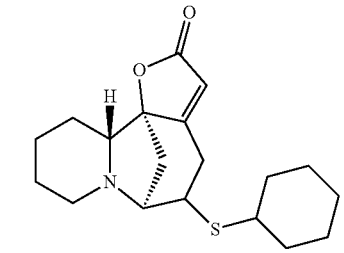
66
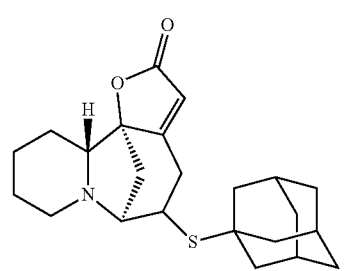
67
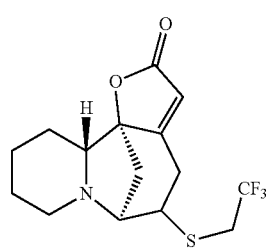
68
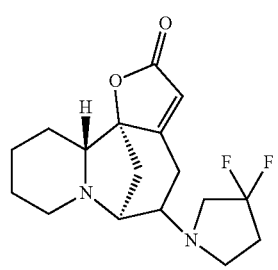
69
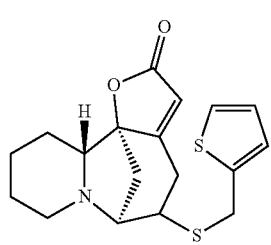
70
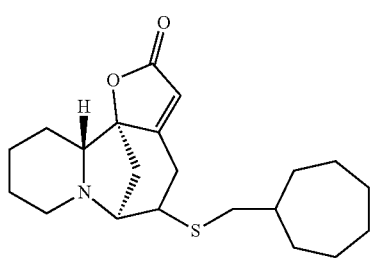
71
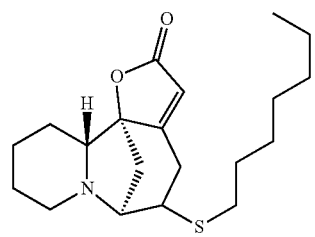
72
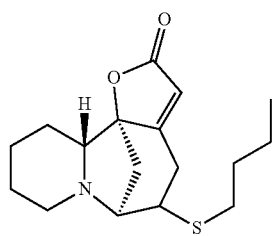
73
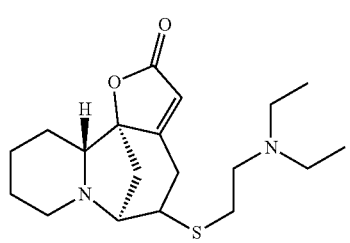
74
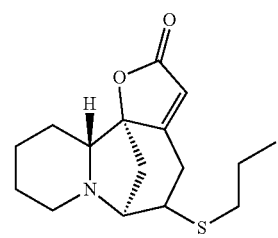
75
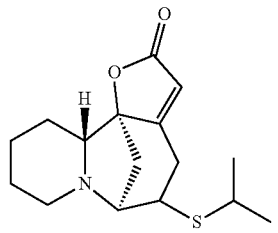
76
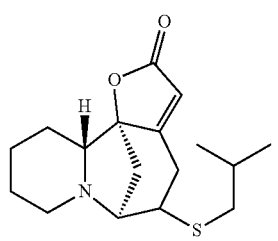

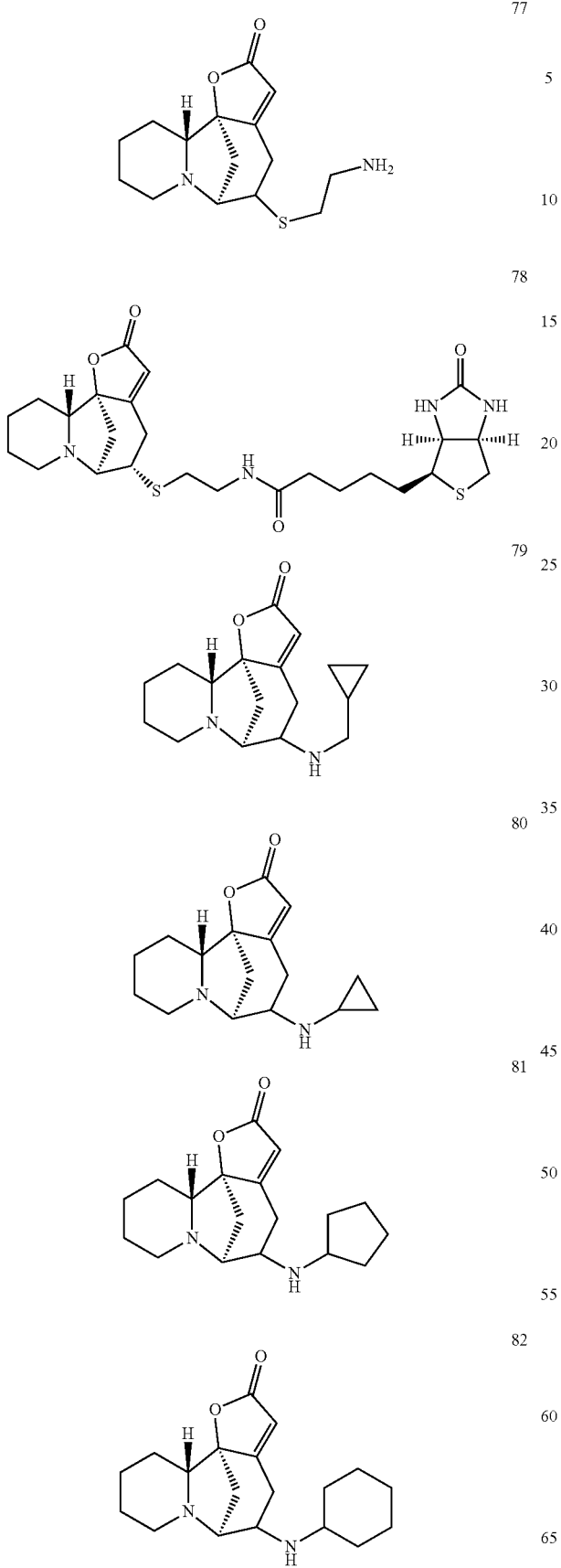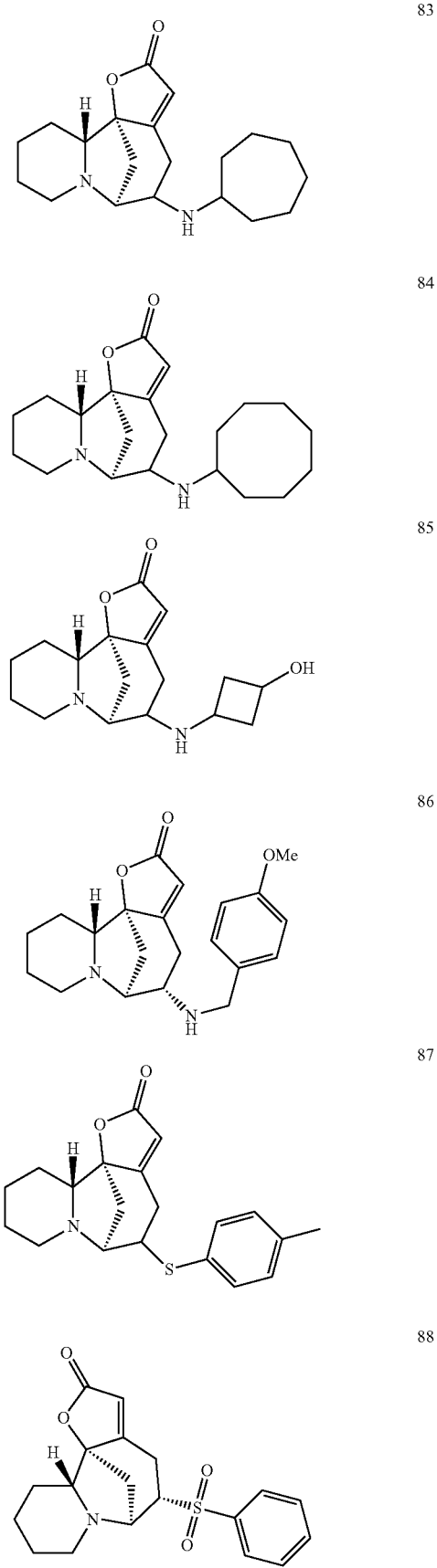 [SMILES: O=C1C=C2CC(NC3CCCCCC3)[C@@H]3C[C@@]2(O1)[C@H]1CCCCN31 ; O=C1C=C2CC(NC3CCCCCCC3)[C@@H]3C[C@@]2(O1)[C@H]1CCCCN31 ; O=C1C=C2CC(NC3CC(O)C3)[C@@H]3C[C@@]2(O1)[C@H]1CCCCN31 ; COc1ccc(CN[C@H]2CC3=CC(=O)O[C@@]34C[C@@H]2N2CCCC[C@@H]24)cc1 ; Cc1ccc(SC2CC3=CC(=O)O[C@@]34C[C@@H]2N2CCCC[C@@H]24)cc1 ; O=C1C=C2C[C@H](S(=O)(=O)c3ccccc3)[C@@H]3C[C@@]2(O1)[C@H]1CCCCN31]

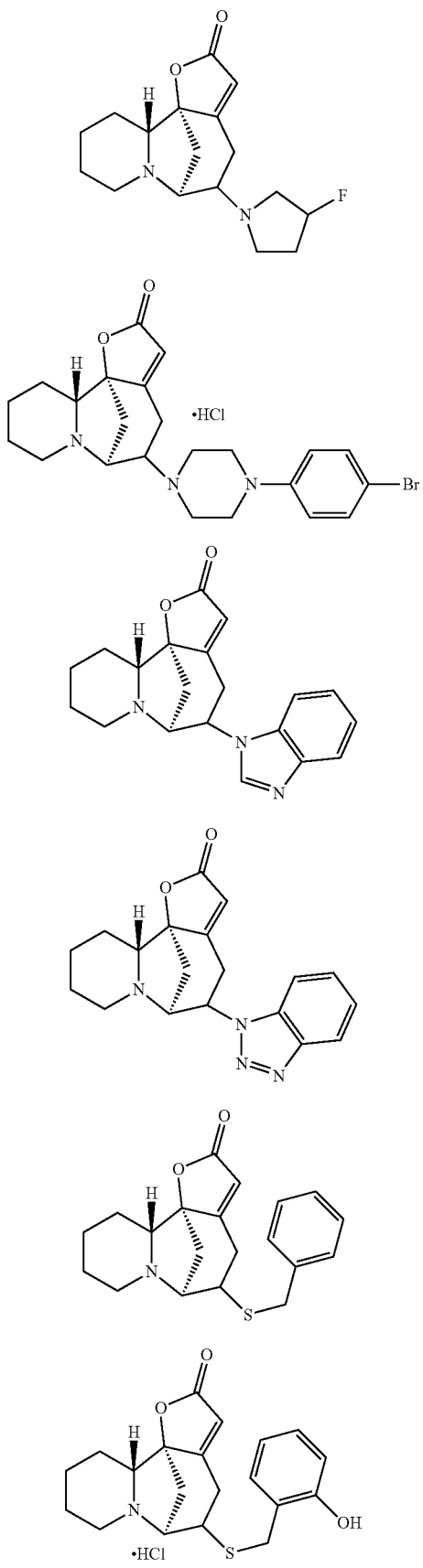
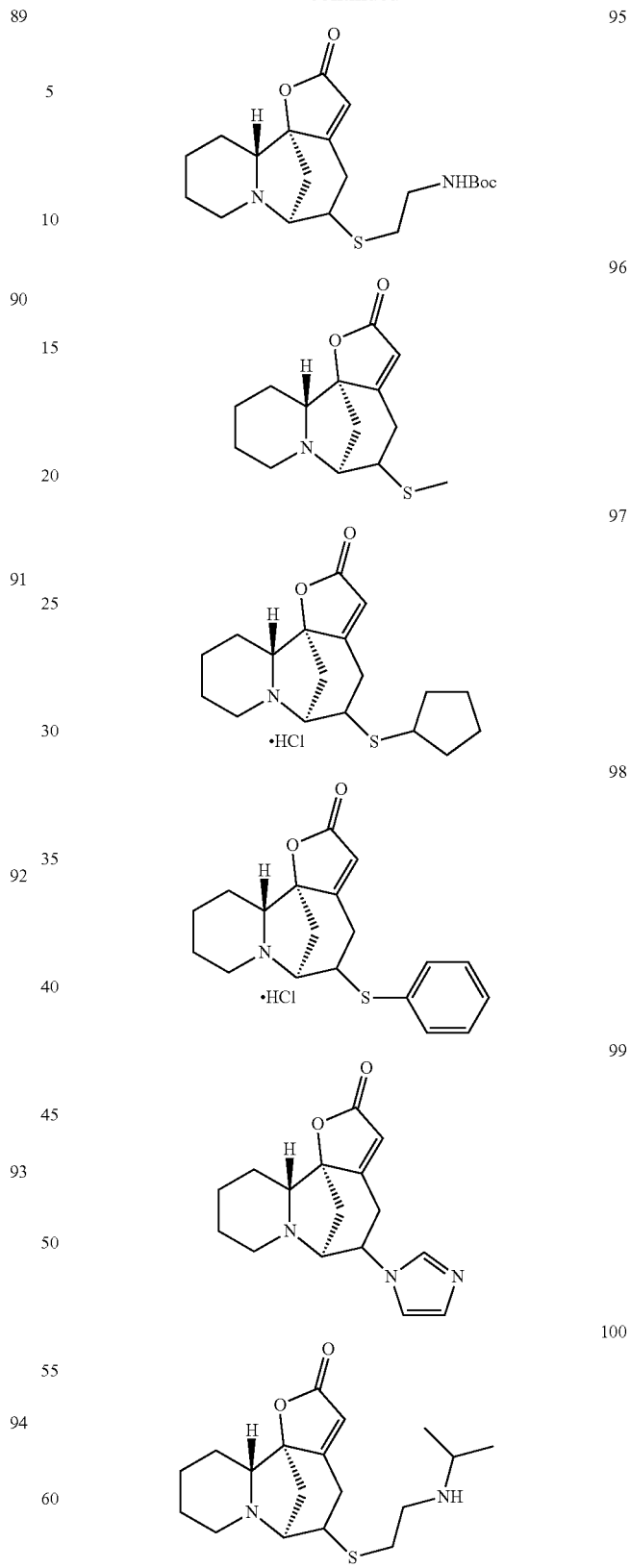
or pharmaceutically acceptable salts thereof. For example, the compound is selected from compounds 65, 66, 67, 68, 69, 70, 71, 72, 73, 75, 76, 77, 78, 79, 80, 81, 82, 83, 84, 85, 86, 87, 88, 89, 90, 91, 92, 93, 94, 95, 96, 97, 99, or 100 or pharmaceutically acceptable salts thereof.

In some embodiments, the securinine analogues are represented by the general Formula (IV'):

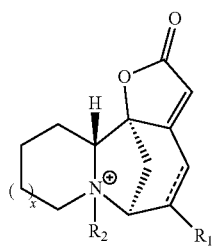

Formula IV' or pharmaceutically acceptable salts thereof, wherein as valence and stability permit:
=== represents a single or double bond;
x is 0 or 1;
$R_1$ is hydrogen or substituted or unsubstituted alkyl, alkenyl, alkynyl, aryl, heteroaryl, cycloalkyl, heterocyclyl, cycloalkylalkyl, heterocyclylalkyl, heteroaralkyl, aralkyl, halo, silyl, hydroxyl, sulfhydryl, alkoxy, alkenyloxy, alkynyloxy, alkoxyalkyl, alkoxyalkenyl, aryloxy, acyl, alkylcarbonato, arylcarbonato, carboxy, carboxylato, carbamoyl, alkylcarbamoyl, arylcarbamoyl, thiocarbamoyl, alkylcarbamido, cyano, isocyano, cyanato, isothiocyanato, azido, formyl, thioformyl, amino, alkylamino, arylamino, cycloalkylamino, heterocyclylamino, cycloalkylalkylamino, arylalkylamino, heteroarylalkylamino, aminoalkyl, imino, nitro, nitroso, sulfo, sulfonato, alkylsulfanyl, arylsulfanyl, cycloalkylsulfanyl, heterocyclylsulfanyl, heteroarylsulfanyl, amidoalkylsulfanyl, arylalkysulfanyl, heteroarylalkylsulfanyl, alkylsulfinyl, arylsulfinyl, alkylsulfonyl, arylsulfonyl, phosphono, phosphonato, phosphinato, phospho, phosphino, thioalkyl, or thioaryl; and wherein $R_2$ is $C_1$-$C_6$ alkyl.

In certain embodiments, === represents a single bond. In certain such embodiments, x is 1.

In certain embodiments wherein $R_1$ is substituted or unsubstituted heterocyclyl, $R_1$ is not fluoro-substituted, such as mono-fluoro substituted pyrrolidine. For example, in certain embodiments wherein $R_1$ is substituted or unsubstituted heterocyclyl, x is 1, and === represents a single bond, $R_1$ is not fluoro-substituted, such as mono-fluoro substituted pyrrolidine. In certain embodiments wherein $R_1$ is substituted or unsubstituted heteroarylalkylamino, $R_1$ is not indolealkylamino. For example, in certain embodiments wherein $R_1$ is substituted or unsubstituted heteroarylalkylamino, x is 1, and === represents a single bond, $R_1$ is not indolealkylamino. In certain embodiments wherein $R_1$ is substituted or unsubstituted arylsulfanyl, $R_1$ is not phenylsulfanyl. For example, in certain embodiments wherein $R_1$ is substituted or unsubstituted arylsulfanyl, x is 1, and === represents a single bond, $R_1$ is not phenylsulfanyl. In certain embodiments wherein $R_1$ is alkylsulfanyl, $R_1$ is not lower alkylsulfanyl, such as propylsulfanyl. For example, in certain embodiments wherein $R_1$ is alkylsulfanyl, x is 1, and === represents a single bond, $R_1$ is not lower alkylsulfanyl, such as propylsulfanyl. In certain embodiments, $R_1$ is hydrogen or substituted or unsubstituted alkyl, alkenyl, alkynyl, aryl, heteroaryl, cycloalkyl, cycloalkylalkyl, heterocyclylalkyl, heteroaralkyl, aralkyl, halo, silyl, hydroxyl, sulfhydryl, alkoxy, alkenyloxy, alkynyloxy, alkoxyalkyl, alkoxyalkenyl, aryloxy, acyl, alkylcarbonato, arylcarbonato, carboxy, carboxylato, carbamoyl, alkylcarbamoyl, arylcarbamoyl, thiocarbamoyl, carbamido, cyano, isocyano, cyanato, isocyanato, isothiocyanato, azido, formyl, thioformyl, amino, alkylamino, arylamino, cycloalkylamino, heterocyclylamino, cycloalkylalkylamino, arylalkylamino, aminoalkyl, imino, nitro, nitroso, sulfo, sulfonato, alkylsulfanyl, cycloalkylsulfanyl, heterocyclylsulfanyl, heteroarylsulfanyl, amidoalkylsulfanyl, arylalkysulfanyl, heteroarylalkylsulfanyl, alkylsulfinyl, arylsulfinyl, arylsulfonyl, phosphono, phosphonato, phosphinato, phospho, phosphino, thioalkyl, or thioaryl. In certain such embodiments, === represents a single bond and x is 1.

Methods of Treatment and Other Methods of Use

For any of the methods described herein, the disclosure contemplates the use of any of the securinine or norsecurinine analogue compounds and/or compositions described throughout the application. In addition, for any of the methods described herein, the disclosure contemplates the combination of any step or steps of one method with any step or steps from another method.

In some embodiments, the disclosure provides for a method of inducing differentiation of a stem cell. In some embodiments, the stem cell is a bone marrow stem cell. In some embodiments, the stem cell is a multipotent hematopoietic stem cell (hemocytoblast). In some embodiments, the disclosure provides for a method of inducing differentiation of a cell of the myeloid lineage, the method comprising: administering to the cell an effective amount of one or more of any of the compounds disclosed herein. In some embodiments, the cell is in a subject. In some embodiments, the subject is a mammal. In some embodiments, the mammal is a human. In some embodiments, the subject has any of the myeloid disorders disclosed herein. In some embodiments, the any of the compounds disclosed herein induces differentiation of the cell into a differentiated myeloid cell. In some embodiments, the differentiated myeloid cell is a thrombocyte, reticulocyte, erythrocyte, mast cell, basophil, neutrophil, eosinophil, macrophage or a myeloid dendritic cell.

In some embodiments, the methods of the disclosure contemplate using any of the securinine or norsecurinine analogue compounds described herein as myeloablative agent in conjunction with bone marrow transplantation and/or stem cell therapies.

In some embodiments, the securinine or norsecurinine analogue compounds described herein can be administered in a therapeutically effective amount to a patient or subject with a disorder characterized by arrest of differentiation of immature myeloid cells. These disorders can include, for example, myeloproliferative disorders, such as leukemia, and immunity related diseases.

In other embodiments, treatment of a patient by administration of a securinine or norsecurinine analogue compound of the present invention encompasses chemoprevention in a patient susceptible to developing myeloid leukemia (e.g., at a higher risk, as a result of genetic predisposition, environmental factors, or the like) and/or in cancer survivors at risk of cancer recurrence, as well as treatment of a myeloid leukemia patient by inhibiting or causing regression of a disorder or disease.

In some embodiments, effective amounts are amounts of the securinine or norsecurinine analogue compound effective to induce or promote differentiation of the immature or cancerous myeloid cells in the subject being treated without being cytotoxic to the subject.

In certain embodiments, the present disclosure provides for methods of treating myeloid disorders in a subject in need thereof by administering any of the securinine or norsecurinine analogue compounds or compositions described herein to the subject. In some embodiments, the subject comprises a cell that is a leukemic or cancer cell. In certain embodiments, the subject in need of treatment has a malignant tumor. In some embodiments, the subject is a human.

In some embodiments, the subject is newly diagnosed with a myeloid disorder. In other embodiments, the subject has had a myeloid disorder for a period of time, and has had one or more prior surgeries or rounds of radiation therapy and/or chemotherapy. In other embodiments, the subject having a myeloid disorder is treatment naïve to a prior cancer therapeutic. In some embodiments, the subject has a malignant tumor, and the subject is treated for the malignant tumor. In certain embodiments, the malignancy is a primary malignancy. In other embodiments, the patient has a secondary malignancy, and the treatment may comprise treating either or both of the primary or secondary malignancy.

In some embodiments, the present disclosure provides for methods of increasing and/or modulating myeloid cell differentiation activity and/or function in a diseased cell, comprising contacting the diseased cell with any of the securinine or norsecurinine analogue compounds or pharmaceutical compositions described herein. In some embodiments, the present disclosure provides for methods of promoting differentiation of an immature myeloid cell. In some embodiments, the diseased cell is a tumor cell. In some embodiments, the diseased cell is a leukemic cell. In some embodiments, the cell is in a subject. In some embodiments, the subject is a human.

In certain embodiments, the present disclosure provides methods of delivering any of the compounds and compositions described herein to cells of the myeloid lineage, including cells in culture (in vitro or ex vivo) and cells in a subject. Delivery to cells in culture, such as healthy cells or cells from a model of disease, has numerous uses. These uses include studies of cell differentiation, elucidation of downstream signaling pathways such as the MAPK pathway, and assessment of gene expression under a variety of conditions (e.g., pH) and the like in healthy or disease contexts. These uses also include studies of securinine and norsecurinine analogue activities and interactions with other molecules, such as proteins, nucleic acids, carbohydrates, ions, lipids, or amino acids. Such interactions can happen within or superficially to the cell and alter the molecule's function. For example, the securinine and norsecurinine analogues may improve catalytic activity of a protein by blocking suppressing molecules or improving access to a catalytic domain or the analogues may inhibit an active site on a protein, such as a catalytic domain or a binding site.

Delivery to subjects, such as to cells in a subject, has numerous uses. Exemplary therapeutic uses are described below. Moreover, the compounds and compositions described herein may be used for diagnostic or research purposes. For example, a compound of the disclosure may be detectably labeled and administered to a subject, such as an animal model of disease or a patient, and used to image the compound in the subject's cells and/or tissues. Additionally exemplary uses include delivery to cells in a subject, such as to an animal model of disease. By way of example, compounds and compositions of the disclosure may be used as reagents and delivered to animals to understand bioactivity, enzymatic activity, interactions with other molecules, gene expression, and impacts on animal physiology in healthy or diseased subjects (e.g., a human having a myeloid disorder).

In certain embodiments, the present disclosure provides methods of treating conditions associated with myeloid disorders. Such conditions include, but are not limited to, abnormal red blood cells or platelets, abnormal white blood cells, an increase in myeloblasts, anemia, fever, shortness of breath, easy bruising or bleeding, petechiae, weakness or fatigue, bone or joint pain, swelling in the abdomen, and weight loss or loss of appetite.

These methods involve, in certain embodiments, administering to the individual a therapeutically effective amount of any of the compounds or compositions described herein. These methods are particularly aimed at therapeutic treatment of animals, and more particularly, humans. With respect to methods for treating myeloid disorders, the disclosure contemplates all combinations of any of the foregoing aspects and embodiments, as well as combinations with any of the embodiments set forth in the detailed description and examples.

In certain embodiments, the method comprises contacting a cell with any of the compounds described herein. In certain embodiments, the cell is a normal human lymphocyte, normal human bone marrow, a mouse embryonic fibroblast, a human umbilical vein endothelial cell, a cancer cell or a tumor cell. In some embodiments, the cancer or tumor cell is a leukemic cell. In some embodiments, the cancer or tumor cell is a sarcoma cell. In certain embodiments, the method is in a subject in need thereof, such as a patient having a myeloid disorder.

A myeloid disorder is any disease, disorder or condition associated with aberrant proliferation, differentiation and/or survival of a cell of the myeloid lineage (e.g., a common myeloid progenitor cell). In some embodiments, the myeloid disorder is associated with increased proliferation of a cell of the myeloid lineage (e.g., myeloid leukemia). In some embodiments, the myeloid disorder is associated with reduced differentiation and/or survival of a myeloid cell or a cell of myeloid lineage. In some embodiments, the myeloid disorder is associated with reduced hematopoiesis of cells of the myeloid lineage. In some embodiments, the myeloid disorder is an autoimmune disease. Examples of myeloid disorders include, but are not limited to, any one of: acute myeloid leukemia (AML), chronic myeloid leukemia (CML), myelodysplastic syndromes (MDS), myelodysplasia, Myelodysplastic Syndrome (e.g., refractory anemia (RA), refractory anemia with ring sideroblasts (RARS), refractory anemia with excess blasts (RAEB), refractory anemia with excess blasts in transformation (RAEBT), and/or chronic myelomonocytic leukemia (CMMoL)), myeloid sarcoma, chloroma, chronic myeloproliferative diseases (CMPD), essential thrombocythemia, polycythemia vera, chronic myelogenous leukemia, myelofibrosis, myelofibrosis with myeloid metaplasia (MMM—also known as agnogenic myeloid metaplasia or idiopathic myelofibrosis), atypical CMD, chronic neutrophilic leukemia, chronic eosinophilic leukemia, systemic mastocytosis, mast cell disease, chronic neutrophilic leukemia (CNL), chronic eosinophilic leukemia (CEL), hypereosinophilic syndrome (HES), unclassified MPD (UMPD), chronic myelomonocytic leukemia (CMML), juvenile myelomonocytic leukemia (JMML), Down Syndrome related myeloid disorders, and myeloid processes that display overlapping features of MDS and CMPD (hybrid CMD). In some embodiments, a subject having a myeloid disorder has a mutation in one or more of the following genes: JAK2, NPM1, MPL, RAS, RUNX1, ASXL1, BCORL1, CBL, DNMT3A, EZH2, IDH1/IDH2, TET2, UTX, SF3B1, SRSF2, U2AF35/U2AF1, ZRSR2, PTPN11, SH3KBP1, CDKN2A/B, TRIM33, CTNNA1, SOCS1 and/or SF3B1. In some embodiments, a myeloid disorder is any of the myeloid disorders described in Murati et al., 2012, BMC Cancer, 12:304. In some embodiments, a myeloid disorder is associated with any one of more of the following symptoms: reduced lifespan, aberrant (e.g., increased) proliferation of a cell of the myeloid lineage, tumor formation, abnormal red blood cells or platelets, abnormal white blood cells, an increase in myeloblasts, anemia, fever, shortness of breath, easy bruising or bleeding, petechiae, weakness or fatigue, bone or joint pain, swelling in the abdomen, and weight loss or loss of appetite.

In some embodiments, any of the securinine or norsecurinine analogue compounds or compositions described herein is administered to a myeloid disorder disease cell (e.g., in vitro or in vivo, such as to a patient in need thereof). In some embodiments, administering a compound or composition to a myeloid disorder disease cell comprises systemically administering the compounds or compositions to a subject in need thereof. Moreover, in certain embodiments, administering to a patient refers to systemic administration.

In certain embodiments, more than one of the compounds described herein can be administered to a myeloid disorder disease cell, together (simultaneously) or at different times (sequentially). In some embodiments, the myeloid disorder disease cell is in a subject. In addition, securinine or norsecurinine analogue compounds of the present disclosure can be administered alone or in combination with one or more additional agents or treatment modalities.

Any of the compounds or pharmaceutical compositions of the disclosure have numerous uses, including in vitro and in vivo uses. In vivo uses include not only therapeutic uses but also diagnostic and research uses in, for example, any of the foregoing animal models. By way of example, any of the compounds or pharmaceutical compositions of the disclosure may be used as research reagents and delivered to animals to understand bioactivity, enzymatic activity, gene expression, interactions with other molecules, and impacts on animal physiology in healthy or diseases animals.

The terms "treatment", "treating", and the like are used herein to generally mean obtaining a desired pharmacologic and/or physiologic effect. "Treating" a condition or disease refers to curing as well as ameliorating at least one symptom of the condition or disease, and includes administration of a composition which reduces the frequency of, or delays the onset of, symptoms of a medical condition in a subject in need relative to a subject which does not receive the composition. "Treatment" as used herein covers any treatment of a disease or condition of a mammal, particularly a human, and includes: (a) preventing or delaying onset of symptoms of the disease or condition from occurring in a subject which may be predisposed to the disease or condition but has not yet begun experiencing symptoms; (b) inhibiting the disease or condition (e.g., arresting its development); or (c) relieving the disease or condition (e.g., causing regression of the disease or condition, providing improvement in one or more symptoms). For example, "treatment" of a myeloid disorder encompasses a complete reversal or cure of the disease, or any range of improvement in symptoms and/or adverse effects attributable to the myeloid disorders. Merely to illustrate, "treatment" of a myeloid disorder may include or improvement in any of the following symptoms or conditions associated with myeloid disorders (or combination thereof): aberrant cell proliferation, tumor cell formation, abnormal red blood cells or platelets, abnormal white blood cells, an increase in myeloblasts, anemia, fever, shortness of breath, easy bruising or bleeding, petechiae, blood clotting, deep venous thrombosis, pulmonary embolism, weakness or fatigue, frequent infections, unusual paleness, failure to thrive, reduced lifespan, night sweats, headaches, dizziness, confusion, slurred speech, bone or joint pain, swelling in the abdomen, enlargement of the spleen and/or liver, and weight loss or loss of appetite. Improvements in any of these symptoms can be readily assessed according to standard methods and techniques known in the art. Other symptoms not listed above may also be monitored in order to determine the effectiveness of treating myeloid disorders. The population of subjects treated by the method of the disclosure includes subjects suffering from the undesirable condition or disease, as well as subjects at risk for development of the condition or disease. Without wishing to be bound by theory, in certain embodiments, administering any of the compounds or compositions described herein may have any one or more of the following effects: decrease in the numbers of abnormal red and white bloods cells and platelets, increase in the differentiation of immature myeloid cells, decrease in proliferation of a cell of the myeloid lineage, decrease in the number of tumor and/or cancer cells (e.g., leukemic cells), decrease in the number of petechiae, improvement of anemia, lessening of bone or joint pain, increase in lifespan, improved mental function, and/or reduction in weight loss. It should be noted that any of the compounds or compositions described above or herein may be used in any of the methods described herein.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The terms "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized terms and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

By the term "therapeutically effective dose" is meant a dose that produces the desired effect for which it is administered. The exact dose will depend on the purpose of the treatment, and will be ascertainable by one skilled in the art using known techniques (see, e.g., Lloyd (1999) The Art, Science and Technology of Pharmaceutical Compounding).

Combination Therapies

In some embodiments, the securinine or norsecurinine analogue compounds can be used in combination and adjunctive therapies for treating proliferative disorders.

In other embodiments, the phrase "combination therapy" embraces the administration of the any of the compounds described herein and an additional therapeutic agent as part of a specific treatment regimen intended to provide a beneficial effect from the co-action of these therapeutic agents. Administration of these therapeutic agents in combination typically is carried out over a defined time period (usually minutes, hours, days or weeks depending upon the combination selected). "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also can embrace the administration of the therapeutic agents as described above in further combination with other biologically active ingredients (such as, but not limited to, a second and different therapeutic agent) and non-drug therapies (such as, but not limited to, surgery or radiation treatment). Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

In another example of combination therapy, one or more securinine or norsecurinine analogue compounds of the disclosure can be used as part of a therapeutic regimen combined with one or more additional treatment modalities. By way of example, such other treatment modalities include, but are not limited to, dietary therapy, occupational therapy, physical therapy, ventilator supportive therapy, massage, acupuncture, acupressure, mobility aids, assistance animals, speech therapy, language therapy, educational therapy, psychological therapy, occupational therapy and the like.

In some embodiments the phrase "adjunctive therapy" encompasses treatment of a subject with agents that reduce or avoid side effects associated with the combination therapy of the present invention, including, but not limited to, those agents, for example, that reduce the toxic effect of anticancer drugs, e.g., bone resorption inhibitors, cardioprotective agents; prevent or reduce the incidence of nausea and vomiting associated with chemotherapy, radiotherapy or operation; or reduce the incidence of infection associated with the administration of myelosuppressive anticancer drugs.

In some embodiments, the mammalian disease treated by the combination therapy can include any of the myeloid disorders described herein. Besides being useful for human treatment, the combination therapy is also useful for veterinary treatment of companion animals, exotic and farm animals, including rodents, horses, dogs, and cats.

In other embodiments, the therapeutic agents administered in combination therapy with the securinine or norsecurinine analogue compounds can comprise at least one anti-proliferative agent selected from the group consisting of a chemotherapeutic agent, an antimetabolite, an antitumorgenic agent, an antimitotic agent, an antiviral agent, an antineoplastic agent, an immunotherapeutic agent, and a radiotherapeutic agent.

In some embodiments, the phrase "anti-proliferative agent" can include agents that exert antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agent agents available in commercial use, in clinical evaluation and in pre-clinical development, which could be included in the present invention by combination drug chemotherapy. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endothelial cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

In some embodiments a first family of anti-proliferative agents, which may be used in combination therapy with any of the compounds described herein, consists of antimetabolite-type anti-proliferative agents. Antimetabolites are typically reversible or irreversible enzyme inhibitors, or compounds that otherwise interfere with the replication, translation or transcription of nucleic acids. Examples of antimetabolite antineoplastic agents that may be used in the present invention include, but are not limited to acanthifolic acid, aminothiadiazole, anastrozole, bicalutamide, brequinar sodium, capecitabine, carmofur, Ciba-Geigy CGP-30694, cladribine, cyclopentyl cytosine, cytarabine phosphate stearate, cytarabine conjugates, cytarabine ocfosfate, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, finasteride, floxuridine, fludarabine phosphate, N-(2'-furanidyl)-5-fluorouracil, Daiichi Seiyaku FO-152, fluorouracil (5-FU), 5-FU-fibrinogen, isopropyl pyrrolizine, Lilly LY-188011, Lilly LY-264618, methobenzaprim, methotrexate, Wellcome MZPES, nafarelin, norspermidine, nolvadex, NCI NSC-127716, NCI NSC-264880, NCI NSC-39661, NCI NSC-612567, Warner-Lambert PALA, pentostatin, piritrexim, plicamycin, Asahi Chemical PL-AC, stearate; Takeda TAC-788, thioguanine, tiazofurin, Erbamont TIF, trimetrexate, tyrosine kinase inhibitors, tyrosine protein kinase inhibitors, Taiho UFT, toremifene, and uricytin, all of which are disclosed in U.S. Pat. No. 6,916,800, which is herein incorporated by reference in its entirety.

In some embodiments, a second family of anti-proliferative agents, which may be used in combination therapy with any of the compounds described herein, consists of alkylating-type anti-proliferative agents. The alkylating agents are believed to act by alkylating and cross-linking guanine and possibly other bases in DNA, arresting cell division. Typical alkylating agents include nitrogen mustards, ethyleneimine compounds, alkyl sulfates, cisplatin, and various nitrosoureas. A disadvantage with these compounds is that they not only attack malignant cells, but also other cells which are naturally dividing, such as those of bone marrow, skin, gastro-intestinal mucosa, and fetal tissue. Examples of alkylating-type anti-proliferative agents that may be used in the present invention include, but are not limited to, Shionogi 254-S, aldo-phosphamide analogues, altretamine, anaxirone, Boehringer Mannheim BBR-2207, bestrabucil, budotitane, Wakunaga CA-102, carboplatin, carmustine (BiCNU), Chinoin-139, Chinoin-153, chlorambucil, cisplatin, cyclophosphamide, American Cyanamid CL-286558, Sanofi CY-233, cyplatate, dacarbazine, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, etoposide phosphate, fotemustine, Unimed G-6-M, Chinoin GYKI-17230, hepsulfam, ifosfamide, iproplatin, lomustine, mafosfamide, mitolactol, mycophenolate, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, thiotepa, Yakult Honsha SN-22, spiromustine, Tanabe Seiyaku TA-077, tauromustine, temozolomide, teroxirone, tetraplatin and trimelamol.

In some embodiments, a third family of anti-proliferative agents that may be used in combination therapy with the securinine or norsecurinine analogue compounds of the present invention consists of antibiotic-type anti-proliferative agents. Examples of antibiotic-type anti-proliferative agents that may be used in the present invention include, but are not limited to Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

In some embodiments, a fourth family of anti-proliferative agents that may be used in combination therapy with any of the compounds described herein consists of synthetic nucleosides. Several synthetic nucleosides have been identified that exhibit anticancer activity. A well known nucleoside derivative with strong anticancer activity is 5-fluorouracil (5-FU). 5-Fluorouracil has been used clinically in the treatment of malignant tumors, including, for example, carcinomas, sarcomas, skin cancer, cancer of the digestive organs, and breast cancer. 5-Fluorouracil, however, causes serious adverse reactions such as nausea, alopecia, diarrhea, stomatitis, leukocytic thrombocytopenia, anorexia, pigmentation, and edema. Derivatives of 5-fluorouracil with anticancer activity have been described in U.S. Pat. No. 4,336,381, which is herein incorporated by reference in its entirety.

In some embodiments, a fifth family of anti-proliferative agents that may be used in combination therapy with any of the compounds described herein consists of hormonal agents. Examples of hormonal-type anti-proliferative agents that may be used in the present invention include, but are not limited to Abarelix; Abbott A-84861; Abiraterone acetate; Aminoglutethimide; anastrozole; Asta Medica AN-207; Antide; Chugai AG-041R; Avorelin; aseranox; Sensus B2036-PEG; Bicalutamide; buserelin; BTG CB-7598; BTG CB-7630; Casodex; cetrolix; clastroban; clodronate disodium; Cosudex; Rotta Research CR-1505; cytadren; crinone; deslorelin; droloxifene; dutasteride; Elimina; Laval University EM-800; Laval University EM-652; epitiostanol; epristeride; Mediolanum EP-23904; EntreMed 2-ME; exemestane; fadrozole; finasteride; flutamide; formestane; Pharmacia & Upjohn FCE-24304; ganirelix; goserelin; Shire gonadorelin agonist; Glaxo Wellcome GW-5638; Hoechst Marion Roussel Hoe-766; NCI hCG; idoxifene; isocordoin; Zeneca ICI-182780; Zeneca ICI-118630; Tulane University J015X; Schering Ag J96; ketanserin; lanreotide; Milkhaus LDI-200; letrozol; leuprolide; leuprorelin; liarozole; lisuride hydrogen maleate; loxiglumide; mepitiostane; Leuprorelin; Ligand Pharmaceuticals LG-1127; LG-1447; LG-2293; LG-2527; LG-2716; Bone Care International LR-103; Lilly LY-326315; Lilly LY-353381-HCl; Lilly LY-326391; Lilly LY-353381; Lilly LY-357489; miproxifene phosphate; Orion Pharma MPV-2213ad; Tulane University MZ-4-71; nafarelin; nilutamide; Snow Brand NKS01; octreotide; Azko Nobel ORG-31710; Azko Nobel ORG-31806; orimeten; orimetene; orimetine; ormeloxifene; osaterone; Smithkline Beecham SKB-105657; Tokyo University OSW-1; Peptech PTL-03001; Pharmacia & Upjohn PNU-156765; quinagolide; ramorelix; Raloxifene; statin; sandostatin LAR; Shionogi S-10364; Novartis SMT-487; somavert; somatostatin; tamoxifen; tamoxifen methiodide; teverelix; toremifene; triptorelin; TT-232; vapreotide; vorozole; Yamanouchi YM-116; Yamanouchi YM-511; Yamanouchi YM-55208; Yamanouchi YM-53789; Schering AG ZK-1911703; Schering AG ZK-230211; and Zeneca ZD-182780.

In some embodiments, a sixth family of anti-proliferative agents that may be used in combination therapy with any of the compounds described herein consists of a miscellaneous family of antineoplastic agents including, but not limited to alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristo-Myers BMY-40481, Vestar boron-10, bromofosfamide, Wellcome BW-502, Wellcome BW-773, calcium carbonate, Calcet, Calci-Chew, Calci-Mix, Roxane calcium carbonate tablets, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Cell Pathways CP-461, Yakult Honsha CPT-11, crisnatol, curaderm, cytochalasin B, cytarabine, cytocytin, Merz D-609, DABIS maleate, dacarbazine, datelliptinium, DFMO, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel, Encore Pharmaceuticals E7869, elliprabin, elliptinium acetate, Tsumura EPMTC, ergotamine, etoposide, etretinate, Eulexin®, Cell Pathways Exisulind® (sulindac sulphone or CP-246), fenretinide, Merck Research Labs Finasteride, Florical, Fujisawa FR-57704, gallium nitrate, gemcitabine, genkwadaphnin, Gerimed, Chugai GLA-43, Glaxo GR-63178, grifolan NMF-5N, hexadecylphosphocholine, Green Cross HO-221, homoharringtonine, hydroxyurea, BTG ICRF-187, ilmofosine, irinotecan, isoglutamine, isotretinoin, Otsuka JI-36, Ramot K-477, ketoconazole, Otsuak K-76COONa, Kureha Chemical K-AM, MECT Corp KI-8110, American Cyanamid L-623, leucovorin, levamisole, leukoregulin, lonidamine, Lundbeck LU-23-112, Lilly LY-186641, Materna, NCI (US) MAP, marycin, Merrel Dow MDL-27048, Medco MEDR-340, megestrol, merbarone, merocyanine derivatives, methylanilinoacridine, Molecular Genetics MGI-136, minactivin, mitonafide, mitoquidone, Monocal, mopidamol, motretinide, Zenyaku Kogyo MST-16, Mylanta, N-(retinoyl)amino acids, Nilandron; Nisshin Flour Milling N-021, N-acylated-dehydroalanines, nafazatrom, Taisho NCU-190, Nephro-Calci tablets, nocodazole derivative, Normosang, NCI NSC-145813, NCI NSC-361456, NCI NSC-604782, NCI NSC-95580, octreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, retinoids, Encore Pharmaceuticals R-flurbiprofen, Sandostatin; Sapporo Breweries RBS, restrictin-P, retelliptine, retinoic acid, Rhone-Poulenc RP-49532, Rhone-Poulenc RP-56976, Scherring-Plough SC-57050, Scherring-Plough SC-57068, seienium(selenite and selenomethionine), SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, Sugen SU-101, Sugen SU-5416, Sugen SU-6668, sulindac, sulindac sulfone; superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, Yamanouchi YM-534, Zileuton, ursodeoxycholic acid, and Zanosar.

In some embodiments, any of the compounds described herein can allow the combination therapeutic agents and/or compounds described herein to be administered at a low dose, that is, at a dose lower than has been conventionally used in clinical situations.

A benefit of lowering the dose of the combination therapeutic agents and any of the securinine or norsecurinine analogue compounds described herein administered to a mammal includes a decrease in the incidence of adverse effects associated with higher dosages. For example, by the lowering the dosage of a chemotherapeutic agent such as methotrexate, a reduction in the frequency and the severity of nausea and vomiting will result when compared to that observed at higher dosages. Similar benefits are contemplated for the compounds, compositions, agents and therapies in combination with the inhibitors of the present invention.

In some embodiments, by lowering the incidence of adverse effects, an improvement in the quality of life of a patient undergoing treatment for cancer is contemplated. Further benefits of lowering the incidence of adverse effects include an improvement in patient compliance, a reduction in the number of hospitalizations needed for the treatment of adverse effects, and a reduction in the administration of analgesic agents needed to treat pain associated with the adverse effects.

Alternatively, the methods and combination of the present invention can also maximize the therapeutic effect at higher doses.

In some embodiments, when administered as a combination, the therapeutic agents can be formulated as separate compositions which are given at the same time or different times, or the therapeutic agents can be given as a single composition.

Methods of Administration

Various delivery systems are known and can be used to administer the pharmaceutical compositions of the disclosure to a subject. Any such methods may be used to administer to a subject any of the pharmaceutical compositions described herein. The disclosure contemplates that any of the methods of administration described herein may be combined with any of the methods disclosure herein. In some embodiments the pharmaceutical compositions of the present invention can be administered by any means that achieve their intended purpose. For example, administration can be by parenteral, subcutaneous, intravenous, intraarticular, intrathecal, intramuscular, intraperitoneal, or intradermal injections, or by transdermal, buccal, oromucosal, ocular routes or via inhalation. The pharmaceutical compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local.

Alternatively or concurrently, administration can be by the oral route. The dosage administered will be dependent upon the age, health, and weight of the patient, kind of concurrent treatment, if any, frequency of treatment, and the nature of the effect desired.

In certain embodiments, it may be desirable to administer the pharmaceutical compositions of the disclosure locally to the area in need of treatment; this may be achieved, for example, and not by way of limitation, by local infusion during surgery, by means of a catheter, or by means of an implant, the implant being of a porous, non-porous, or gelatinous material, including membranes, such as sialastic membranes, fibers, or commercial skin substitutes.

Note that the disclosure contemplates methods in which pharmaceutical compositions are administered, at the same or different times, via one than one route of administration. For example, the disclosure contemplates a regimen in which the pharmaceutical compositions are administered systemically, such as by intravenous infusion, in combination with local administration via the hepatic portal vein.

In other embodiments, any of the pharmaceutical compositions described herein can be delivered in a vesicle, in particular, a liposome (see Langer, 1990, Science 249:1527-1533). In yet another embodiment, the pharmaceutical compositions of the disclosure can be delivered in a controlled release system. In another embodiment, a pump may be used (see Langer, 1990, supra). In another embodiment, polymeric materials can be used (see Howard et al., 1989, J. Neurosurg. 71:105). In certain specific embodiments, the pharmaceutical compositions of the disclosure can be delivered intravenously.

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical Compositions

In some embodiments, any of the compounds described herein can be provided in the form of pharmaceutical compositions. The pharmaceutical compositions can be administered to any mammal that can experience the beneficial effects of the securinine or norsecurinine analogue compounds of the present invention. Foremost among such animals are humans, although the present invention is not intended to be so limited.

In some embodiments, in addition to the pharmacologically active compounds, the pharmaceutical preparations of the securinine or norsecurinine analogue compounds can contain suitable pharmaceutically acceptable carriers comprising excipients and auxiliaries that facilitate processing of the active agents into preparations that can be used pharmaceutically. The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active agents with solid excipients, optionally grinding the resulting mixture and processing the mixture of granules, after adding suitable auxiliaries, if desired or necessary, to obtain tablets or dragee cores.

In other embodiments, suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as acetylcellulose phthalate or hydroxypropylmethylcellulose phthalate, are used. Slow-release and prolonged-release formulations may be used with particular excipients such as methacrylic acid-ethylacrylate copolymers, methacrylic acid-ethyl acrylate copolymers, methacrylic acid-methyl methacrylate copolymers and methacrylic acid-methyl methylacrylate copolymers. Dye stuffs or pigments can be added to the tablets or dragee coatings, for example, for identification or in order to characterize combinations of active compound doses.

In some embodiments, other pharmaceutical preparations that can be used orally include push-fit capsules made of gelatin, as well as soft, sealed capsules made of gelatin and a plasticizer such as glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds may be dissolved or suspended in suitable liquids such as fatty oils or liquid paraffin. In addition, stabilizers may be added.

In some embodiments, formulations for parenteral administration include aqueous solutions of the active compounds in water-soluble form, for example, water-soluble salts and alkaline solutions. In some embodiments, salts are maleate, fumarate, succinate, S,S tartrate, or R,R tartrate. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example sodium carboxymethyl cellulose, sorbitol, and/or dextran. Optionally, the suspension may also contain stabilizers.

The term "pharmaceutical composition" refers to a formulation containing the disclosed compounds in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In one embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Animal/Cell Models

Myeloid disorders been modeled in animals such as mice. For example, mice expressing NuMA-RARa carry a genetic myeloproliferation characterized by increased granulopoiesis, impaired neutrophil differentiation, abnormal cytokine response, and responsiveness to ATRA. The disease observed in these mice is progressive and contains many characteristics of acute promyelocytic leukemia (APL) (Sukhai et al., 2004, Oncogene, 23, 665-678).

To generate a murine xenograft model of acute myeloid leukemia, HL-60 or MV4-11 leukemic cells may be implanted into athymic nude mice (Charles River Laboratories) by subcutaneous injection.

Further mice models of myeloid disorders include any of the mouse models described in Beachy et al., 2010, Hematol. Oncol. Clin. North Amer., 24(2): 361-375 (which is incorporated herein in its entirety), including mice carrying $Pten^{+/-}$; $Ship^{-/-}$ mutations, mice overexpressing Evi1, mice having $Npm^{+/-}$ mutations, mice having $Dido^{-/-}$ mutations, NUP98-HOXD13 mice, mice overexpressing Sall4B, mice overexpressing Bcl-2 and expressing NRASD12 mutations, mice engrafted with immortalized cell lines from MDS patients, mice having the $Poly^{4/4}$ mutation, mice having the $Arid4a^{-/-}$ mutation, mice having the RUNX1 D171N mutation, and/or mice having the AML-S291fsX300 mutation.

In addition, cell models for assessing myeloid disorders are available. For example, HL-60 cells are a cell line model for acute myeloid leukemia (AML)(ATCC). Other leukemic cell lines include KASUMI-1, THP-1, K-562, MOLT-4, MOLT-3, OCI-AML3, and MV4-11 (ATCC).

In some embodiments, the compounds and pharmaceutical compositions disclosed herein will be tested on normal human lymphocytes, normal human bone marrow, mouse embryonic fibroblasts, human umbilical vein endothelial cells, and cancer cell lines. The effects of the compounds and pharmaceutical compositions on cell proliferation, cell cycle kinetics, differentiation, and cell death/toxicity can be assessed. For example, securinine potently inhibits the proliferation of HL-60 cells; leads to the accumulation of cells in G0/G1; can differentiate a variety of leukemic cell lines; and exhibits low toxicity across 60 cancer cell lines, normal human lymphocytes, normal human bone marrow, mouse embryonic fibroblasts, and human umbilical vein endothelial cells. Any of the compounds disclosed herein can be similarly tested for similar effects on cells, such as HL-60 cells. Soft agar colony assays can be utilized to study inhibition of colony formation and assess the compounds and pharmaceutical compositions abilities to induce terminal differentiation (U.S. patent application Ser. No. 14/029,066).

In an aspect of the present disclosure, the compounds of the disclosure can be identified using a novel high-throughput screen that is biased to identify agents that have both a high potency and low toxicity in a myeloid disorder disease model, such as an animal or cell model. In some embodiments, the high-throughput screen measures the differentiation of HL-60 leukemic cells using a quantitative nitroblue tetrazolium (NBT) reduction assay. Screening HL-60 cells, human promyelocytic cells, is advantageous as they have been used extensively as a cell line to study myeloid differentiation. Though promyelocytic cells, HL-60 cells were derived from a patient with acute myeloblastic leukemia with maturation, FAB-M2. This cell line has been shown to be an appropriate model to study myeloid differentiation as it undergoes terminal differentiation to either granulocytic or monocytic pathways with numerous known compounds. The differentiated cells demonstrate all of the expected functional properties such as chemotaxis, bacterial killing, ingestion, and respiratory burst activity.

Nitroblue Tetrazolium (NBT) reduction has been widely demonstrated to provide a very accurate correlation to the extent of myeloid differentiation to both granulocytic and monocytic pathways. This technique has also been widely exploited in HL-60 cells to analyze myelomonocytic differentiation. In fact, it has been routinely demonstrated for over 20 years that the NBT test provides an extremely close correlation with the morphology of the differentiated cells.

The NBT screen works due to changes in the oxidoreductases during differentiation that lead to increases in rates of NBT reduction. NBT is reduced due to the production of superoxide that is catalyzed by an NADPH oxidase. This enzyme is inactive in resting cells, therefore, it is necessary to treat the cells with PMA to generate an oxidative burst. NBT is reduced by superoxide from a soluble yellow compound to insoluble blue formazan granules whose formation can be monitored spectrophotometrically at 560 nm as the unreduced dye has minimal absorbance at this wavelength. A quantitative NBT reduction assay is ideal for this type of screen as it is simple, sensitive, quantitative, requires minimal cells, has been proven to have low well to well variability, and the amount of reduced NBT is proportional to the number of cells reducing the dye as well as the amount reduced by each cell.

The above models are exemplary of suitable animal and cell model systems for assessing the activity and effectiveness of the compounds and pharmaceutical compositions and/or formulations. These models have correlations with symptoms of myeloid disorders, and thus provide appropriate models. Activity of the subject compounds and pharmaceutical compositions and/or formulations are assessed in any one or more of these models, and the results compared to that observed in wildtype control animals and/or cells, and animals and/or cells not treated with the compounds and pharmaceutical compositions. In some embodiments, the subject compounds and pharmaceutical compositions are evaluated using cells prepared from any of the foregoing mutant mice or other animals, as well as wild type cells, such as fibroblasts and lymphocytes. These assays have been described in U.S. patent application Ser. No. 14/029,066, hereby incorporated by reference.

Moreover, in vitro systems may be used to evaluate the ability of any of the compounds or pharmaceutical compositions to mediate gene expression. For example, in some embodiments, gene expression of cells treated with any of the compounds or pharmaceutical compositions of interest is assessed at 16 and 72 hours after treatment using gene microarrays. Results are compared to that observed in control cells or cells not treated with the compounds and pharmaceutical compositions (U.S. patent application Ser. No. 14/029,066).

In vitro systems can be utilized to demonstrate the capability of these compounds and pharmaceutical compositions to induce differentiation as measured by morphologic changes, up-regulation of the cell surface markers, and NBT reduction. For example, securinine induces clear morphologic changes suggestive of monocytic differentiation, as evidenced by indented and condensed nuclei that lack prominent nucleoli and more abundant and vacuolated cytoplasm. Flow cytometric analysis supports that securinine leads to monocytic differentiation. While the cell surface marker CD11b is induced during both granulocytic and monocytic differentiation, the marker CD14 is specific to monocytic differentiation. Securinine and the known monocytic differentiation-inducing agent vitamin D3 induce CD14 and CD11b, while ATRA, a granulocytic differentiation-inducing agent, primarily induces CD11b. From the NBT reduction assay, securinine has similar activity to ATRA in HL-60 cells as ~95% of cells are differentiated by these compounds (U.S. patent application Ser. No. 14/029, 066). Any of the compounds disclosed herein can be tested in similar assays.

Additionally, in vitro systems can be used to compare the activity of the compounds or pharmaceutical compositions disclosed with the activity of known differentiation-inducing agents such as ATRA and vitamin D3. For example, the expression of the transcription factor CEBPβ is known to be critical for monocytic differentiation, and securinine was found to induce a time-dependent upregulation of CEBPβ. Similarly, the transcription factor c-myc, important in regulating cell proliferation and known to be downregulated during terminal differentiation, was potently downregulated by securinine Securinine was found to cause cells to accumulate in the G0/G1 phase of the cell cycle. The protein p21 is known to block the G1 to S phase transition by repressing the cyclin D/CDK4/6 complex, and as is common with other differentiation-inducing compounds such as ATRA, the p21 protein was upregulated by securinine Finally, several other characterized differentiation-inducers activate MAPK signaling pathways, and securinine induces rapid phosphorylation of p44/p42 and p38 (U.S. patent application Ser. No. 14/029,066). Any of the compounds disclosed herein can be tested in similar assays.

In some embodiments, in vitro systems can be used to study the interactions of securinine and norsecurinine analogues with other molecules, such as proteins, nucleic acids, carbohydrates, ions, lipids, or amino acids. Such interactions can happen within or superficially to the cell and alter the molecule's function. For example, the securinine and norsecurinine analogues may improve catalytic activity of a protein by blocking suppressing molecules or improving access to a catalytic domain or the analogues may inhibit an active site on a protein, such as a catalytic domain or a binding site.

The effects of any of the pharmaceutical compositions and compounds disclosed herein may be tested in any of the cells or animal models disclosed herein.

The pharmaceutical compositions and compounds of the disclosure have numerous uses, including in vitro and in vivo uses. In vivo uses include not only therapeutic uses but also diagnostic and research uses in, for example, any of the foregoing animal models. By way of example, pharmaceutical compositions and compounds of the disclosure may be used as research reagents and delivered to animals to understand bioactivity, enzymatic activity, gene expression, interactions with other molecules, and impacts on animal physiology in healthy or diseased animals or cells.

Kits

In certain embodiments, the disclosure also provides a pharmaceutical package or kit comprising one or more containers filled with at least one compound or composition of the disclosure. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both. In certain embodiments, the kit comprises at least two containers, at least one of which contains at least one compound or composition of the disclosures. In certain embodiments, the kit contains at least two containers, and each of at least two containers contains a compound or composition of the disclosure.

In certain embodiments, the kit includes additional materials to facilitate delivery of the subject compounds or compositions. For example, the kit may include one or more of a catheter, tubing, infusion bag, syringe, and the like. In certain embodiments, the compounds or compositions are packaged in a lyophilized form, and the kit includes at least two containers: a container comprising the lyophilized compounds or compositions and a container comprising a suitable amount of water, buffer, or other liquid suitable for reconstituting the lyophilized material.

The foregoing applies to any of the compounds, compositions, and methods described herein. The disclosure specifically contemplates any combination of the features of such compounds, compositions, and methods (alone or in combination) with the features described for the various kits described in this section.

Preparation of the Compounds of the Invention

In some embodiments, one or more of the compounds, or components to make the compounds, of Formula (I), Formula (II), Formula (III), Formula (IV) or Formula (IV') are commercially available, for example from commercial sources such as Sigma-Aldrich® of St. Louis, Mo., USA; TCI America, Portland, Oreg., USA; and Acros Organics, Geel, Belgium; among others. They may be natural (e.g. extracted from biomass or naturally synthesized by microbes or enzymatically) or synthetic.

In some embodiments, one or more of the compounds of Formula (I), Formula (I'), Formula (II), Formula (III), Formula (IV) or Formula (IV') are prepared from commercially available reagents by routine methods in synthetic organic chemistry.

Compounds of Formula (I), Formula (I'), and Formula (II)

In one embodiment, one or more compounds of Formula (I), Formula (I'), and Formula (II) were prepared by the multi-step synthetic sequence described below. One of skill in the art would be able to readily adapt the described conditions for the synthesis of compounds of Formula (I), Formula (I'), and Formula (II).

The γ-iodo derivatives of securinine and norsecurinine (1 and 14) were prepared from securinine using N-iodosuccinimide in MeOH (J.-Y. Li, et al., Tetrahedron, 2012, 68, 21, 3972-3979, which is hereby incorporated by reference). During the product isolation from the reaction mixture, side products 1 and 2 were also isolated. Using the intermediates 1 and 14, further analogues of securinine and norsecurinine were prepared.

In one embodiment, the C-14 alkyl/aryl analogues of securinine were prepared using 14 and the corresponding boronic acids/esters. Bis(triphenylphosphine)palladium(II) dichloride (7 mg, 0.01 mmol) was added to a stirred solution of 14 (34.3 mg, 0.1 mmol) in anhydrous toluene or tetrahydrofuran (0.75 mL) followed by the corresponding boronic acid (0.2 mmol) and then potassium carbonate/water (20 mg, 0.15 mmol/75 uL). The reaction mixture was degassed under nitrogen atmosphere for 15 minutes and then gradually heated to 80° C. to 100° C. The reaction progress was monitored by thin layer chromatography (TLC) and the reaction mixture was stirred at that temperature for 1 to 2 hours until the starting material was completely consumed. The reaction mixture was poured in water (2 mL) and extracted with ethyl acetate (2×3 mL) and the combined organic layers were washed with brine (5 mL), dried over sodium sulfate and concentrated on a rotary evaporator. The crude product was dried under high vacuum and purified by silica gel chromatography using an appropriate solvent system to afford the desired C-14 alkyl/aryl analogue of securinine in 40-70% yield (Scheme 1):

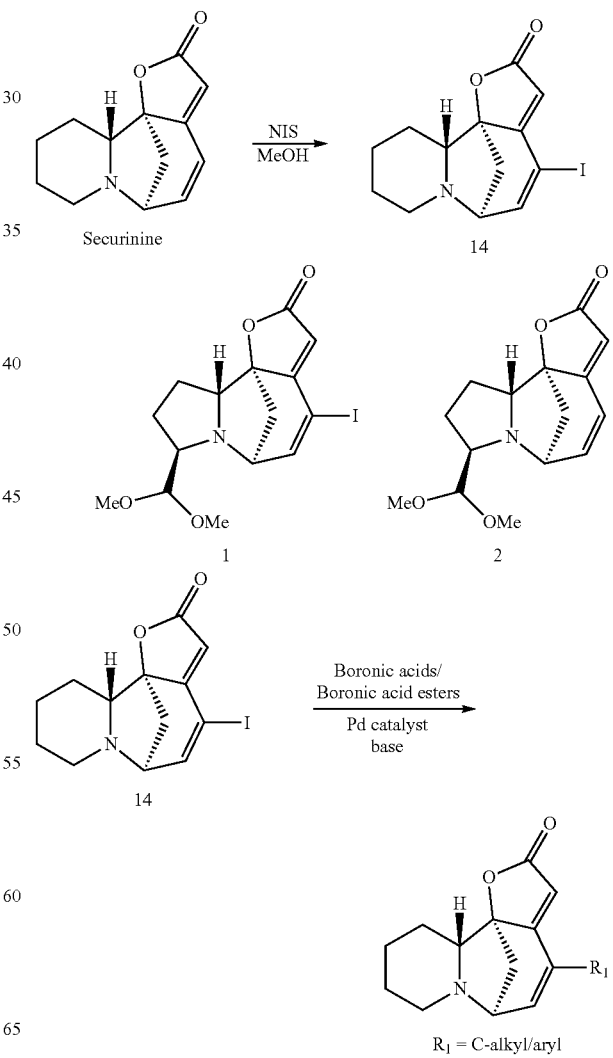

Scheme 1

Compounds of Formula (III)

In one embodiment, one or more compounds of Formula (III) were prepared by the synthetic sequence described below. One of skill in the art would be able to readily adapt the described conditions for the synthesis of compounds of Formula (III).

To a solution of 14 (26 mg, 0.075 mmol) in anhydrous 1,4-dioxane/tetrahydrofuran (0.75 mL) was added bis(triphenylphosphine)palladium(II)dichloride (2.6 mg, 0.00375 mmol), CuI (1.5 mg, 0.0075 mmol) and triethylamine (52 uL, 0.375 mmol). The reaction mixture was degassed under nitrogen atmosphere for 10 minutes and then gradually heated to 80° C. At this point, the reaction mixture turned into homogeneous, clear, dark brown solution. The reaction was brought to room temperature and the corresponding alkyne (0.1125 mmol) was added. The reaction progress was monitored by thin layer chromatography (TLC) and the reaction mixture was stirred at room temperature for 1 to 2 hours until the starting material was completely consumed. The reaction mixture was poured into water (2 mL) and extracted with ethyl acetate (2×3 mL) and the combined organic layers were washed with brine (5 mL), dried over sodium sulfate and concentrated on a rotary evaporator. The crude product was dried under high vacuum and purified by silica gel chromatography using an appropriate solvent system to afford the corresponding C-14 alkynyl analogue of securinine Alkynyl analogues of securinine and norsecurinine have been synthesized employing the above procedure in 50-90% yield (Scheme 2):

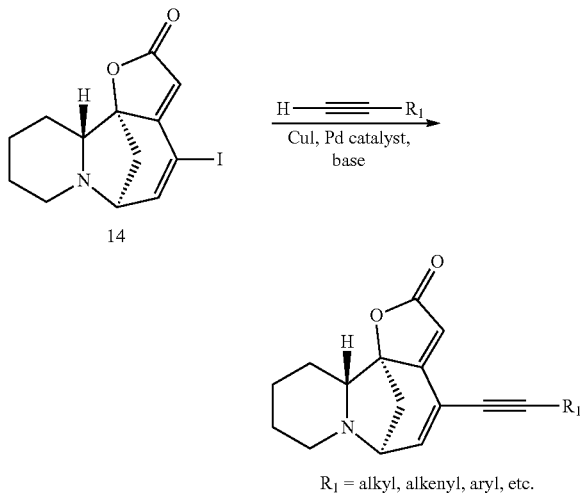

Compounds of Formula (IV) and Formula (IV')

In one embodiment, one or more compounds of Formula (IV) and Formula (IV') were prepared by the synthetic sequence described below. One of skill in the art would be able to readily adapt the described conditions for the synthesis of compounds of Formula (IV) and Formula (IV').

In one variation, C-15 analogues of securinine were prepared by 1,6-conjugate addition of thials/amines following the general procedure outlined below.

54.3 mg of securinine (0.25 mmol) and 0.3-0.4 mmol of the corresponding amine/thial were weighed in an oven dried reaction flask equipped with a septa or a 4 mL vial with a Teflon cap. 1 mL of acetonitrile followed by triethylamine (139 uL, 1 mmol) was added and the reaction mixture was stirred under nitrogen atmosphere at room temperature. The reaction mixture was monitored by thin layer chromatography (TLC). The reaction mixture was allowed to stir from 8 hours to 2 days at room temperature until the starting material was completely consumed or maximum product formation was observed. All the volatiles in the reaction mixture were evaporated under reduced pressure and the crude product was purified by flash column chromatography on silica gel, using an appropriate hexanes/acetone solvent system. C-15 analogues of securinine have been synthesized employing the above procedure in 55-95% yield (Scheme 3):

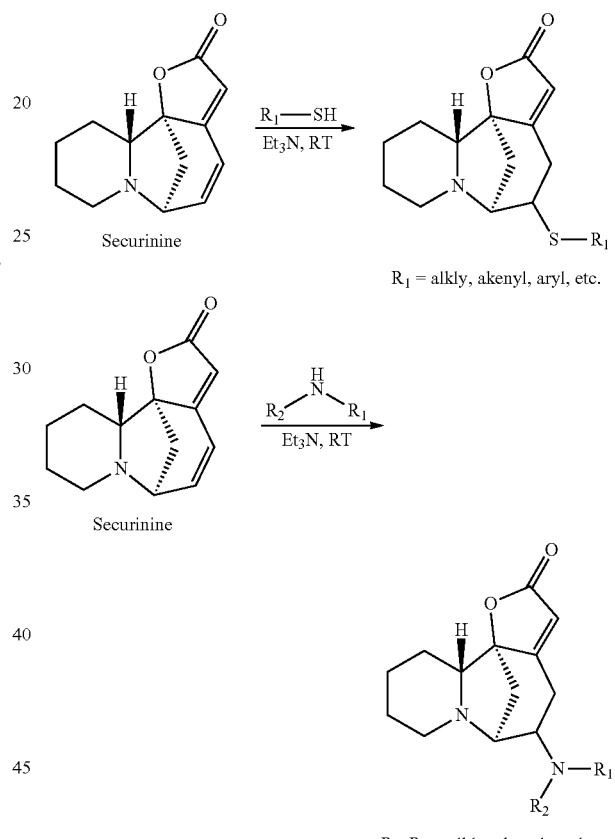

Salts of Securinine and Norsecurinine Analogues

In one embodiment, one or more salts of securinine or norsecurinine analogues were prepared by the method described below. One of skill in the art would be able to readily adapt the described conditions to generate salts of securinine and norsecurinine analogues disclosed in the invention.

Securinine or norsecurinine analogues were dissolved in 1,4-dioxane and added to a 2N HCl/1,4-dioxane solution mixture at 0° C. The reaction mixture was stirred as the product slowly precipitates. Hexanes or ether were then added and the solids filtered and washed to obtain the corresponding HCl salts.

Similarly, a securinine or norsecurinine analogue was dissolved in methanol and to this mixture, tartaric acid was added. The reaction mixture was gradually heated to 80° C.

as the product slowly precipitates. Ether was then added and the solids filtered and washed to obtain the corresponding tartarate salts.

EXEMPLIFICATION

The disclosure now being generally described, it will be more readily understood by reference to the following examples, which are included merely for purposes of illustration of certain aspects and embodiments of the present disclosure, and are not intended to limit the disclosure. For example, the particular constructs and experimental design disclosed herein represent exemplary tools and methods for validating proper function. As such, it will be readily apparent that any of the disclosed specific constructs and experimental plan can be substituted within the scope of the present disclosure.

Example 1 Identification of Novel Differentiation-Inducing Compounds

To discover novel AML differentiation-inducing compounds a rapid high-throughput screen (HTS) was developed and optimized. The screen was designed to be biased to identify compounds that, unlike the majority of known differentiation-inducing agents, have both high potency and low toxicity. The screen measured the differentiation of HL-60 leukemic cells using a quantitative Nitroblue Tetrazolium (NBT) reduction assay, a test that is used extensively as a measure of functional myelomonocytic differentiation. The basis for the screen is unreduced NBT exists as a yellow soluble dye. Differentiated leukemic cells are capable of producing a respiratory burst that can reduce NBT into a blue insoluble compound that can be measured spectrophotometrically. This forward chemical genetics approach allowed the discovery of novel compounds that can act on targets not previously known to be "drugable." As only live cells can reduce NBT, the screen is biased in identifying relatively nontoxic compounds.

To perform the screen, duplicate plates of HL-60 cells were cultured at a density of 5×10⁴ cells/mL with 10 µM of each compound in 96 well plates for 5 days. To determine the relative capability for a compound to induce differentiation compared to known potent inducers, each plate destined for the NBT reduction assay included wells with 0.1% DMSO (vehicle control) and 1 µM ATRA. This approach eliminates any slight day to day variation in NBT reduction values and allows the discovery of compounds with similar or greater efficacy to ATRA. Differentiation was determined in the 96 well plates by incubating the cells with 1 mg/mL of NBT and 200 ng/mL of PMA as the stimulant for the respiratory burst for 35 minutes at 37° C. The reaction was then stopped with HCl and the formazan solubilized with DMSO. Finally, the reaction mixture was read spectrophotometrically at 560 nm in a plate reader.

The securinine and norsecurinine analogues were tested and evaluated on their abilities to affect differentiation and growth of HL-60 cells (Table 1).

TABLE 1

| Analogue | HL-60, $Dif_{50}/IC_{50}$ |
| --- | --- |
| Securinine | $10 < Dif_{50} < 15$ |
| 74 | $15 < Dif_{50} < 20$ |
| 75 | $15 < Dif_{50} < 20$ |
| INVS-MG-3B-I & 3B-II | $15 < Dif_{50} < 20$ |

TABLE 1-continued

| Analogue | HL-60, $Dif_{50}/IC_{50}$ |
| --- | --- |
| 66 | $30 < Dif_{50} <$ not tested |
| INVS-MG-5B | $30 < Dif_{50} <$ not tested |
| 67 | $20 < Dif_{50} < 30$ |
| 68 | $30 < Dif_{50} <$ not tested |
| INVS-MG-12A | $0.5 < Dif_{50} < 0.75$ |
| 69 | $20 < Dif \leq 30$ |
| 70 | $10 < Dif_{50} < 15$ |
| 71 | $20 < Dif_{50} < 30$ |
| 72 | $20 < Dif_{50} < 30$ |
| 73 | $10 < Dif < 15$ |
| 79 | $10 < Dif_{50} < 15$ |
| 80 | $20 < Dif_{50} < 30$ |
| 81 | $10 < Dif_{50} < 15$ |
| 82 | $15 < Dif_{50} < 20$ |
| 83 | $30 < Dif_{50} <$ not tested |
| 84 | $30 < Dif_{50} <$ not tested |
| Sec-1 | $30 < Dif_{50} <$ not tested |
| 93 | $30 < Dif_{50} <$ not tested |
| Sec-3 | $10 < Dif_{50} < 15$ |
| 94 | $15 < Dif_{50} < 20$ |
| 95 | $15 < Dif_{50} < 20$ |
| 97 | $15 < Dif_{50} < 20$ |
| Sec-7 | $15 < Dif_{50} < 20$ |
| 96 | $10 < Dif_{50} < 15$ |
| 98 | $20 < Dif_{50} < 30$ |
| 90 | $15 < Dif_{50} < 20$ |
| 91 | $30 < Dif_{50} <$ not tested |
| 92 | $20 < Dif_{50} < 30$ |
| 99 | $15 < Dif_{50} < 20$ |
| Sec-16 | $20 < Dif_{50} < 30$ |
| 100 | $15 < Dif_{50} < 20$ |
| Sec-18 & Sec-20 | $20 < Dif_{50} < 30$ |
| Sec-19 | $20 < Dif_{50} < 30$ |
| Sec-21 | $20 < Dif_{50} < 30$ |
| Sec-22 | $15 < Dif_{50} < 20$ |
| Sec-23 | NT |
| 85 | $10 < Dif_{50} < 15$ |
| 14 | $0.5 < Dif_{50} < 0.75$ |
| 1 | 100% Death $<2.5$ |
| 2 | $3.25 < Dif_{50} < 5$ |
| INVS-MG-56B | $30 < Dif_{50} <$ not tested |
| 4 | $3 < IC_{50} < 4$ |
| INVS-MG-57A | $20 < Dif_{50} < 30$ |
| INVS-MG-58C = 34B | $15 < Dif_{50} < 20$ |
| 5 | $20 < IC_{50} < 30$ |
| 6 | $15 < IC_{50} < 20$ |
| 7 | $15 < IC_{50} < 20$ |
| 8 | $30 < Dif_{50} <$ not tested |
| 9 | $5 < IC_{50} < 7.5$ |
| 10 | $15 < Dif_{50} < 20$ |
| 11 | $0.25 < IC_{50} < 0.375$ |
| INVS-MG-44 | $15 < Dif_{50} < 20$ |
| INVS-MG-59 | $15 < Dif_{50} < 20$ |
| INVS-MG-60 | $15 < Dif_{50} < 20$ |
| INVS-MG-66B | $10 < IC_{50} < 7.5$ |
| 12 | $10 < Dif_{50} < 15$ |
| 13 | not tested $< IC_{50} < 2.5$ |
| 77 | $10 < Dif_{50} < 15$ |
| 86 | $15 < Dif_{50} < 20$ |
| INVS-MG-86C | $30 < Dif_{50} <$ not tested |
| INVS-MG-94-aq | $30 < Dif_{50} <$ not tested |
| INVS-MG-97-IIB | $30 < Dif_{50} <$ not tested |
| INVS-MG-98B | $10 < Dif_{50} < 15$ |
| 78 | $10 < Dif_{50} < 15$ |
| INVS-MG-82-II | $0.156 < IC_{50} < 0.31$ |
| INVS-MG-99A = 12A | $0.156 < IC_{50} < 0.31$ |
| INVS-MG-99B = 52B | $0.156 < IC_{50} < 0.31$ |
| INVS-MG-99D = 52D | $0.31 < IC_{50} < 0.625$ |
| INVS-MG-108-IIB | $0.31 < IC_{50} < 0.625$ |
| 16 | $1.25 < IC_{50} < 2.5$ |
| 17 | $0.07 < IC_{50} < 0.156$ |
| 18 | $0.07 < IC_{50} < 0.156$ |
| 19 | $0.31 < IC_{50} < 0.625$ |
| INVS-MG-110-IIB = 110B | $IC_{50} = 1.25$ |
| INVS-MG-111-IIB = 111B | $0.07 < IC_{50} < 0.156$ |

TABLE 1-continued

| Analogue | HL-60, Dif$_{50}$/IC$_{50}$ |
|---|---|
| INVS-MG-111-III = 111B HCl salt | 0.07 < IC$_{50}$ < 0.156 |
| 20 | IC$_{50}$ = 2.5 |
| 22 | 0.31 < IC$_{50}$ < 0.625 |
| 23 | 1.25 < IC$_{50}$ < 2.5 |
| 24 | 1.25 < IC$_{50}$ < 2.5 |
| 25 | 1.25 < IC$_{50}$ < 2.5 |
| 26 | 0.31 < IC$_{50}$ < 0.625 |
| INVS-MG-111-IVB = 111B | 0.07 < IC$_{50}$ < 0.156 |
| INVS-MG-111-V = 111B HCl salt | 0.07 < IC$_{50}$ < 0.156 |
| INVS-MG-125-IIA = 125A | 1.25 < IC$_{50}$ < 2.5 |
| 56 | 0.625 < IC$_{50}$ < 1.25 |
| INVS-MG-118-IIB | 2.5 < IC$_{50}$ < 5 |
| 27 | 0.625 < IC$_{50}$ < 1.25 |
| 28 | 0.156 < IC$_{50}$ < 0.31 |
| 29 | 0.039 < IC$_{50}$ < 0.078 |
| 30 | 0.31 < IC$_{50}$ < 0.625 |
| 31 | 0.156 < IC$_{50}$ < 0.31 |
| 32 | IC$_{50}$ = 1.25 |
| INVS-MG-133-II | 1.25 < IC$_{50}$ < 2.5 |
| 33 | 0.625 < IC$_{50}$ < 1.25 |
| 34 | 1.25 < IC$_{50}$ < 2.5 |
| 35 | 0.07 < IC$_{50}$ < 0.156 |
| INVS-MG-145-II | 0.625 < IC$_{50}$ < 1.25 |
| 36 | 0.156 < IC$_{50}$ < 0.31 |
| INVS-MG-146-II | 0.31 < IC$_{50}$ < 0.625 |
| 37 | 5 < IC$_{50}$ < 10 |
| 38 | 1.25 < IC$_{50}$ < 2.5 |
| 39 | 0.07 < IC$_{50}$ < 0.156 |
| INVS-MG-119A | 0.625 < IC$_{50}$ < 1.25 |
| INVS-MG-144B | 0.31 < IC$_{50}$ < 0.625 |
| INVS-MG-147B | 0.625 < IC$_{50}$ < 1.25 |
| INVS-MG-149B' | 1.25 < IC$_{50}$ < 2.5 |
| 57 | 0.07 < IC$_{50}$ < 0.156 |
| 58 | 0.07 < IC$_{50}$ < 0.156 |
| 42 | 20/20 at 10uM |
| 43 | 50/40 at 1.25uM |
| 44 | 2.5 < IC$_{50}$ < 5 |
| 45 | 1.25 < IC$_{50}$ < 2.5 |
| 46 | 0.31 < IC$_{50}$ < 0.625 |
| 47 | 0.31 < IC$_{50}$ < 0.625 |
| 48 | 0.31 < IC$_{50}$ < 0.625 |
| INVS-MG-136-IIB | 0.156 < IC$_{50}$ < 0.31 |
| INVS-MG-136-III | NT < IC$_{50}$ < 0.07 |
| 49 | 0.31 < IC$_{50}$ < 0.625 |
| 50 | 0.625 < IC$_{50}$ < 1.25 |
| 51 | NT < IC$_{50}$ < 0.07 |
| 52 | 0.07 < IC$_{50}$ < 0.156 |
| 53 | 0.156 < Dif$_{50}$ < 0.31 |
| 87 | 15 < Dif$_{50}$ < 10 |
| 88 | 5 < Dif$_{50}$ < 7.5 |
| INVS-MG-146-IIIB | 0.07 < IC$_{50}$ < 0.156 |
| INVS-MG-146-IV | 0.07 < IC$_{50}$ < 0.156 |
| INVS-MG-152-IIB | NT < IC$_{50}$ < 0.03 |
| 62 | NT < IC$_{50}$ < 0.03 |
| INVS-MG-157-IIB | 0.07 < IC$_{50}$ < 0.156 |
| 57 | 0.07 < IC$_{50}$ < 0.156 |
| INVS-MG-158-IIB | 0.03 < IC$_{50}$ < 0.07 |
| 58 | 0.07 < IC$_{50}$ < 0.156 |
| INVS-MG-169-IIB | 0.156 < IC$_{50}$ < 0.31 |
| 59 | 0.07 < IC$_{50}$ < 0.156 |
| INVS-MG-170-IIB | 0.03 < IC$_{50}$ < 0.07 |
| 60 | 0.07 < IC$_{50}$ < 0.156 |
| 63 | IC$_{50}$ = 0.156 |
| 54 | IC$_{50}$ = 0.31 |
| 64 | 0.156 < IC$_{50}$ < 0.31 |
| 101 | 0.5 ± 0.05 |
| 102 | 0.25 ± 0.04 |
| 103 | 0.25 ± 0.8 |
| 104 | 4.5 ± 0.05 |
| 105 | 0.07 ± 0.04 |
| 106 | 0.350 ± 0.07 |
| 107 | 0.42 ± 0.6 |
| 108 | 0.42 ± 0.03 |
| 109 | 0.42 ± 0.04 |

TABLE 1-continued

| Analogue | HL-60, Dif$_{50}$/IC$_{50}$ |
|---|---|
| 110 | 1.2 ± 0.07 |
| 111 | 0.15 ± 0.03 |
| 112 | 1.15 ± 0.04 |

Example 2 Identification of Novel Compounds for Inhibiting Cancer Cell Growth

In certain embodiments, securinine and norsecurinine analogues were administered to cancerous cells, such as acute myeloblastic leukemia cells (e.g., MOLT3 and OCI-AML3) and growth inhibition was analyzed. The analogues were effective in inhibiting myeloid growth in addition to promoting differentiation, and provide for reduced proliferation of acute myeloblastic leukemia cells (Table 2).

TABLE 2

| Analogue | MOLT3 IC$_{50}$ (nM) | OCI-AML3 IC$_{50}$ (nM) |
|---|---|---|
| INVS-MG-82-II | 90 | 100 |
| INVS-MG-99B | 80 | 110 |
| INVS-MG-99D | 150 | 168 |
| 17 | 70 | 80 |
| 18 | 70 | 90 |
| 22 | 196 | 220 |
| 26 | 160 | 195 |
| 28 | 165 | 200 |
| 29 | 60 | 80 |
| 31 | 60 | 75 |
| 35 | 130 | 110 |
| 36 | 115 | 105 |
| 39 | 80 | 70 |
| 40 | 90 | 105 |
| 41 | 150 | 180 |
| 46 | 145 | 205 |
| 47 | 150 | 215 |
| 48 | >300 | >300 |
| INVS-MG-136-III | 100 | 115 |

We claim:

1. A method of treating acute myeloid leukemia in a subject, comprising: administering to the subject having acute myeloid leukemia a therapeutically effective amount of at least one securinine or norsecurinine analogue compound, wherein the compound has a formula selected from the group consisting of the following formula:

a. Formula (I):

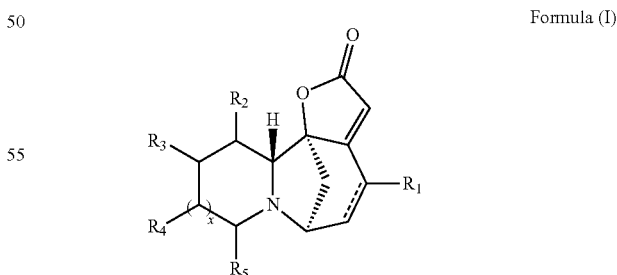

Formula (I)

or pharmaceutically acceptable salts thereof, wherein as valence and stability permit:
═══ represents a single or double bond;
x is 0 or 1;
R$_1$ is hydrogen or substituted or unsubstituted alkyl, alkenyl, alkynyl, aryl, heteroaryl, cycloalkyl, heterocyclyl, cycloalkylalkyl, heterocyclylalkyl, heteroaralkyl, aralkyl, halo, silyl, hydroxyl, sulfhydryl, alkoxy, alkenyloxy, alkynyloxy, alkoxyalkyl, alkoxyalkenyl, aryloxy, acyl, alkylcarbonato, arylcarbonato, carboxy, carboxylato, carbamoyl, alkylcarbamoyl, arylcarbamoyl, thiocarbamoyl, carbamido, cyano, isocyano, cyanato, isocyanato, isothiocyanato, azido, formyl, thioformyl, amino, alkylamino, arylamino, cycloalkylamino, heterocyclylamino, cycloalkylalkylamino, arylalkylamino, heteroarylalkylamino, aminoalkyl, imino, nitro, nitroso, sulfo, sulfonato, alkylsulfanyl, arylsulfanyl, cycloalkylsulfanyl, heterocyclylsulfanyl, heteroarylsulfanyl, amidoalkylsulfanyl, arylalkysulfanyl, heteroarylalkylsulfanyl, alkylsulfinyl, arylsulfinyl, alkylsulfonyl, arylsulfonyl, phosphono, phosphonato, phosphinato, phospho, phosphino, thioalkyl, or thioaryl;

$R_2$, $R_3$, $R_4$, and $R_5$ are each independently hydrogen or substituted or unsubstituted alkyl, alkenyl, alkynyl, aryl, heteroaryl, cycloalkyl, heterocyclyl, cycloalkylalkyl, heterocyclylalkyl, heteroaralkyl, aralkyl, halo, silyl, hydroxyl, sulfhydryl, alkoxy, alkenyloxy, alkynyloxy, alkoxyalkyl, alkoxyalkenyl, aryloxy, acyl, alkylcarbonato, arylcarbonato, carboxy, carboxylato, carbamoyl, alkylcarbamoyl, arylcarbamoyl, thiocarbamoyl, carbamido, cyano, isocyano, cyanato, isocyanato, isothiocyanato, azido, formyl, thioformyl, amino, alkylamino, arylamino, cycloalkylamino, heterocyclylamino, cycloalkylalkylamino, arylalkylamino, heteroarylalkylamino, aminoalkyl, imino, nitro, nitroso, sulfo, sulfonato, alkylsulfanyl, arylsulfanyl, cycloalkylsulfanyl, heterocyclylsulfanyl, heteroarylsulfanyl, amidoalkylsulfanyl, arylalkysulfanyl, heteroarylalkylsulfanyl, alkylsulfinyl, arylsulfinyl, alkylsulfonyl, arylsulfonyl, phosphono, phosphonato, phosphinato, phospho, phosphino, thioalkyl, or thioaryl; and wherein adjacent R groups may be linked to form a cyclic or polycyclic ring, wherein the ring is a substituted or unsubstituted aryl, a substituted or unsubstituted heteroaryl, a substituted or unsubstituted cycloalkyl, or a substituted or unsubstituted heterocyclyl;

provided that when x is 1, at least one of $R_1$, $R_2$, $R_3$, $R_4$, and $R_5$ is other than hydrogen provided that when x is 0, === represents a double bond and $R_5$ is alkoxyalkyl;

b. Formula I':

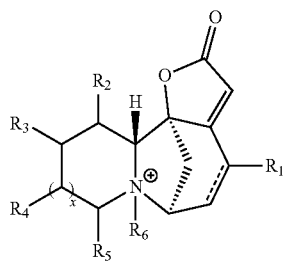

Formula (I')

or pharmaceutically acceptable salts thereof, wherein as valence and stability permit:
=== represents a single or double bond;
x is 0 or 1;
$R_1$ is hydrogen or substituted or unsubstituted alkyl, alkenyl, alkynyl, aryl, heteroaryl, cycloalkyl, heterocyclyl, cycloalkylalkyl, heterocyclylalkyl, heteroaralkyl, aralkyl, halo, silyl, hydroxyl, sulfhydryl, alkoxy, alkenyloxy, alkynyloxy, alkoxyalkyl, alkoxyalkenyl, aryloxy, acyl, alkylcarbonato, arylcarbonato, carboxy, carboxylato, carbamoyl, alkylcarbamoyl, arylcarbamoyl, thiocarbamoyl, carbamido, cyano, isocyano, cyanato, isocyanato, isothiocyanato, azido, formyl, thioformyl, amino, alkylamino, arylamino, cycloalkylamino, heterocyclylamino, cycloalkylalkylamino, arylalkylamino, heteroarylalkylamino, aminoalkyl, imino, nitro, nitroso, sulfo, sulfonato, alkylsulfanyl, arylsulfanyl, cycloalkylsulfanyl, heterocyclylsulfanyl, heteroarylsulfanyl, amidoalkylsulfanyl, arylalkysulfanyl, heteroarylalkylsulfanyl, alkylsulfinyl, arylsulfinyl, alkylsulfonyl, arylsulfonyl, phosphono, phosphonato, phosphinato, phospho, phosphino, thioalkyl, or thioaryl;

$R_2$, $R_3$, $R_4$, and $R_5$ are each independently hydrogen or substituted or unsubstituted alkyl, alkenyl, alkynyl, aryl, heteroaryl, cycloalkyl, heterocyclyl, cycloalkyl alkyl, heterocyclylalkyl, heteroaralkyl, aralkyl, halo, silyl, hydroxyl, sulfhydryl, alkoxy, alkenyloxy, alkynyloxy, alkoxyalkyl, alkoxyalkenyl, aryloxy, acyl, alkylcarbonato, arylcarbonato, carboxy, carboxylato, carbamoyl, alkylcarbamoyl, arylcarbamoyl, thiocarbamoyl, carbamido, cyano, isocyano, cyanato, isocyanato, isothiocyanato, azido, formyl, thioformyl, amino, alkylamino, arylamino, cycloalkylamino, heterocyclylamino, cycloalkylalkylamino, arylalkylamino, heteroarylalkylamino, aminoalkyl, imino, nitro, nitroso, sulfo, sulfonato, alkylsulfanyl, arylsulfanyl, cycloalkylsulfanyl, heterocyclylsulfanyl, heteroarylsulfanyl, amidoalkylsulfanyl, arylalkysulfanyl, heteroarylalkylsulfanyl, alkylsulfinyl, arylsulfinyl, alkylsulfonyl, arylsulfonyl, phosphono, phosphonato, phosphinato, phospho, phosphino, thioalkyl, or thioaryl;

wherein adjacent R groups may be linked to form a cyclic or polycyclic ring, wherein the ring is a substituted or unsubstituted aryl, a substituted or unsubstituted heteroaryl, a substituted or unsubstituted cycloalkyl, or a substituted or unsubstituted heterocyclyl; and wherein $R_6$ is $C_1$-$C_6$ alkyl;

provided that when x is 1, at least one of $R_1$, $R_2$, $R_3$, $R_4$, and $R_5$ is other than hydrogen;

c. Formula (II):

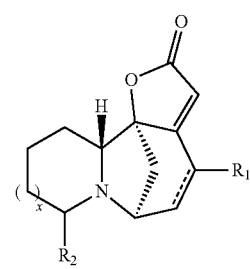

Formula (II)

or pharmaceutically acceptable salts thereof, wherein as valence and stability permit:
=== represents a single or double bond;
x is 0 or 1;
$R_1$ is hydrogen or substituted or unsubstituted alkyl, alkenyl, alkynyl, aryl, heteroaryl, cycloalkyl, heterocyclyl, cycloalkylalkyl, heterocyclylalkyl, heteroaralkyl, aralkyl, halo, silyl, hydroxyl, sulfhydryl, alkoxy, alkenyloxy, alkynyloxy, alkoxyalkyl, alkoxyalkenyl, aryloxy, acyl, alkylcarbonato, arylcarbonato, carboxy, carboxylato, carbamoyl, alkylcarbamoyl, arylcarbamoyl, thiocarbamoyl, carbamido, cyano, isocyano, cyanato, isocyanato, isothiocyanato, azido, formyl, thioformyl, amino, alkylamino, arylamino, cycloalkylamino, heterocyclylamino, cycloalkylalkylamino, arylalkylamino, heteroarylalkylamino, aminoalkyl, imino, nitro, nitroso, sulfo, sulfonato, alkylsulfanyl, arylsulfanyl, cycloalkylsulfanyl, heterocyclylsulfanyl, heteroarylsulfanyl, amidoalkylsulfanyl, arylalkysulfanyl, heteroarylalkylsulfanyl, alkylsulfinyl, arylsulfinyl, alkylsulfonyl, arylsulfonyl, phosphono, phosphonato, phosphinato, phospho, phosphino, thioalkyl, or thioaryl; and $R_2$ is hydrogen or substituted or unsubstituted alkyl, alkenyl, alkynyl, aryl, heteroaryl, cycloalkyl, heterocyclyl, cycloalkylalkyl, heterocyclylalkyl, heteroaralkyl, aralkyl, halo, silyl, hydroxyl, sulfhydryl, alkoxy, alkenyloxy, alkynyloxy, alkoxyalkyl, alkoxyalkenyl, aryloxy, acyl, alkylcarbonato, arylcarbonato, carboxy, carboxylato, carbamoyl, alkylcarbamoyl, arylcarbamoyl, thiocarbamoyl, carbamido, cyano, isocyano, cyanato, isocyanato, isothiocyanato, azido, formyl, thioformyl, amino, alkylamino, arylamino, cycloalkylamino, heterocyclylamino, cycloalkylalkylamino, arylalkylamino, heteroarylalkylamino, aminoalkyl, imino, nitro, nitroso, sulfo, sulfonato, alkylsulfanyl, arylsulfanyl, cycloalkylsulfanyl, heterocyclylsulfanyl, heteroarylsulfanyl, amidoalkylsulfanyl, arylalkysulfanyl, heteroarylalkylsulfanyl, alkylsulfinyl, arylsulfinyl, alkylsulfonyl, arylsulfonyl, phosphono, phosphonato, phosphinato, phospho, phosphino, thioalkyl, or thioaryl;

provided that when x is 1, at least one of $R_1$ or $R_2$ is other than hydrogen provided that when x is 0, === represents a double bond and $R_2$ is alkoxyalkyl;

d. Formula III:

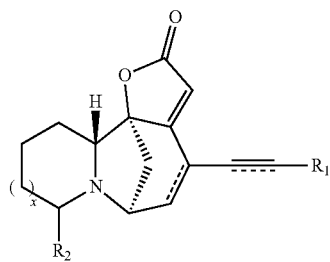

Formula (III)

or pharmaceutically acceptable salts thereof, wherein as valence and stability permit:
=== represents a single or double bond;
≡≡ represents a double or triple bond;
x is 0 or 1;
$R_1$ is hydrogen or substituted or unsubstituted alkyl, alkenyl, alkynyl, aryl, heteroaryl, cycloalkyl, heterocyclyl, cycloalkylalkyl, heterocyclylalkyl, heteroaralkyl, aralkyl, halo, silyl, hydroxyl, sulfhydryl, alkoxy, alkenyloxy, alkynyloxy, alkoxyalkyl, alkoxyalkenyl, aryloxy, acyl, alkylcarbonato, arylcarbonato, carboxy, carboxylato, carbamoyl, alkylcarbamoyl, arylcarbamoyl, thiocarbamoyl, carbamido, cyano, isocyano, cyanato, isocyanato, isothiocyanato, azido, formyl, thioformyl, amino, alkylamino, arylamino, cycloalkylamino, heterocyclylamino, cycloalkylalkylamino, arylalkylamino, heteroarylalkylamino, aminoalkyl, imino, nitro, nitroso, sulfo, sulfonato, alkylsulfanyl, arylsulfanyl, cycloalkylsulfanyl, heterocyclylsulfanyl, heteroarylsulfanyl, amidoalkylsulfanyl, arylalkysulfanyl, heteroarylalkylsulfanyl, alkylsulfinyl, arylsulfinyl, alkylsulfonyl, arylsulfonyl, phosphono, phosphonato, phosphinato, phospho, phosphino, thioalkyl, or thioaryl; and $R_2$ is hydrogen or substituted or unsubstituted alkyl, alkenyl, alkynyl, aryl, heteroaryl, cycloalkyl, heterocyclyl, cycloalkylalkyl, heterocyclylalkyl, heteroaralkyl, aralkyl, halo, silyl, hydroxyl, sulfhydryl, alkoxy, alkenyloxy, alkynyloxy, alkoxyalkyl, alkoxyalkenyl, aryloxy, acyl, alkylcarbonato, arylcarbonato, carboxy, carboxylato, carbamoyl, alkylcarbamoyl, arylcarbamoyl, thiocarbamoyl, carbamido, cyano, isocyano, cyanato, isocyanato, isothiocyanato, azido, formyl, thioformyl, amino, alkylamino, arylamino, cycloalkylamino, heterocyclylamino, cycloalkylalkylamino, arylalkylamino, heteroarylalkylamino, aminoalkyl, imino, nitro, nitroso, sulfo, sulfonato, alkylsulfanyl, arylsulfanyl, cycloalkylsulfanyl, heterocyclylsulfanyl, heteroarylsulfanyl, amidoalkylsulfanyl, arylalkysulfanyl, heteroarylalkylsulfanyl, alkylsulfinyl, arylsulfinyl, alkylsulfonyl, arylsulfonyl, phosphono, phosphonato, phosphinato, phospho, phosphino, thioalkyl, or thioaryl;

e. Formula IV:

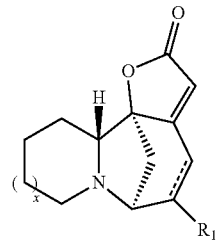

Formula IV or pharmaceutically acceptable salts thereof, wherein as valence and stability permit:
=== represents a single or double bond;
x is 0 or 1; and
$R_1$ is substituted or unsubstituted alkyl, alkenyl, alkynyl, aryl, heteroaryl, cycloalkyl, heterocyclyl, cycloalkylalkyl, heterocyclylalkyl, heteroaralkyl, aralkyl, halo, silyl, hydroxyl, sulfhydryl, alkoxy, alkenyloxy, alkynyloxy, alkoxyalkyl, alkoxyalkenyl, aryloxy, acyl, alkylcarbonato, arylcarbonato, carboxy, carboxylato, carbamoyl, alkylcarbamoyl, arylcarbamoyl, thiocarbamoyl, carbamido, cyano, isocyano, cyanato, isocyanato, isothiocyanato, azido, formyl, thioformyl, amino, alkylamino, arylamino, cycloalkylamino, heterocyclylamino, cycloalkylalkylamino, arylalkylamino, heteroarylalkylamino, aminoalkyl, imino, nitro, nitroso, sulfo, sulfonato, alkylsulfanyl, arylsulfanyl, cycloalkylsulfanyl, heterocyclylsulfanyl, heteroarylsulfanyl, amidoalkylsulfanyl, arylalkysulfanyl, heteroarylalkylsulfanyl, alkylsulfinyl, arylsulfinyl, alkylsulfonyl, arylsulfonyl, phosphono, phosphonato, phosphinato, phospho, phosphino, thioalkyl, or thioaryl;

provided that wherein R₁ is substituted or unsubstituted heterocyclyl, x is 1, and === represents a single bond, R₁ is not mono-fluoro substituted pyrrolidine;

provided that wherein R₁ is substituted or unsubstituted heteroarylalkylamino, x is 1, and === represents a single bond, R₁ is not indolealkylamino;

provided that wherein R₁ is substituted or unsubstituted arylsulfanyl, x is 1, and === represents a single bond, R₁ is not phenylsulfanyl; and provided that wherein R₁ is alkylsulfanyl, x is 1, and === represents a single bond R₁ is not propylsulfanyl, and f. Formula IV':

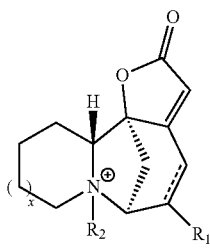

Formula IV' or pharmaceutically acceptable salts thereof, wherein as valence and stability permit:

=== represents a single or double bond;

x is 0 or 1;

R₁ is hydrogen or substituted or unsubstituted alkyl, alkenyl, alkynyl, aryl, heteroaryl, cycloalkyl, heterocyclyl, cycloalkylalkyl, heterocyclylalkyl, heteroaralkyl, aralkyl, halo, silyl, hydroxyl, sulfhydryl, alkoxy, alkenyloxy, alkynyloxy, alkoxyalkyl, alkoxyalkenyl, aryloxy, acyl, alkylcarbonato, arylcarbonato, carboxy, carboxylato, carbamoyl, alkylcarbamoyl, arylcarbamoyl, thiocarbamoyl, carbamido, cyano, isocyano, cyanato, isocyanato, isothiocyanato, azido, formyl, thioformyl, amino, alkylamino, arylamino, cycloalkylamino, heterocyclylamino, cycloalkylalkylamino, arylalkylamino, heteroarylalkylamino, aminoalkyl, imino, nitro, nitroso, sulfo, sulfonato, alkylsulfanyl, arylsulfanyl, cycloalkylsulfanyl, heterocyclylsulfanyl, heteroarylsulfanyl, amidoalkylsulfanyl, arylalkysulfanyl, heteroarylalkylsulfanyl, alkylsulfinyl, arylsulfinyl, alkylsulfonyl, arylsulfonyl, phosphono, phosphonato, phosphinato, phospho, phosphino, thioalkyl, or thioaryl; and wherein R₂ is C₁-C₆ alkyl;

provided that wherein R₁ is substituted or unsubstituted heterocyclyl, R₁ is not mono-fluoro substituted pyrrolidine, x is 1, and === represents a single bond;

provided that wherein R₁ is substituted or unsubstituted heteroarylalkylamino, R₁ is not indolealkylamino, x is 1, and === represents a single bond;

provided that wherein R₁ is substituted or unsubstituted arylsulfanyl, R₁ is not phenylsulfanyl, x is 1, and === represents a single bond; and provided that wherein R₁ is alkylsulfanyl, R₁ is not propylsulfanyl, x is 1, and === represents a single bond.

2. The method of claim 1, wherein the securinine or norsecurinine analogue is selected from:

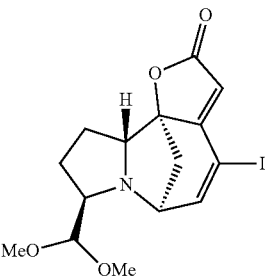

1

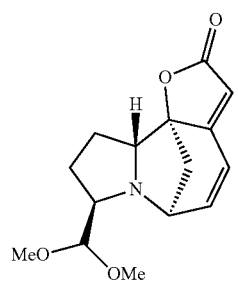

2

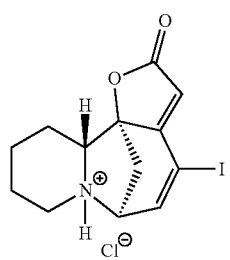

11

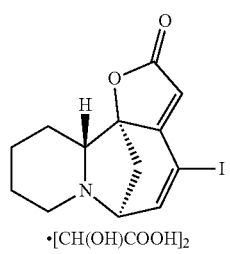

13

·[CH(OH)COOH]₂

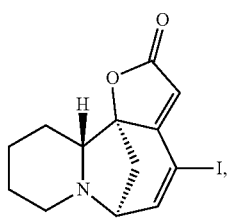

14 or pharmaceutically acceptable salts thereof.

3. The method of claim 1, wherein the securinine or norsecurinine analogue is selected from:

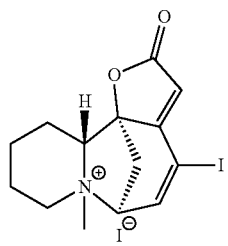

9 and pharmaceutically acceptable salts thereof.

4. The method of claim 1, wherein the securinine or norsecurinine analogue is selected from:

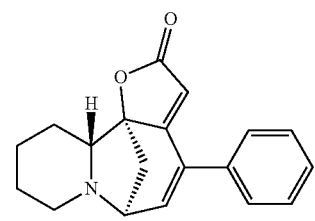

3

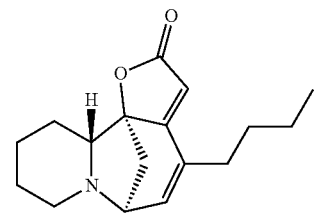

4

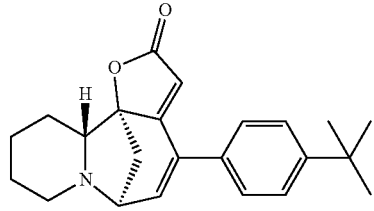

5

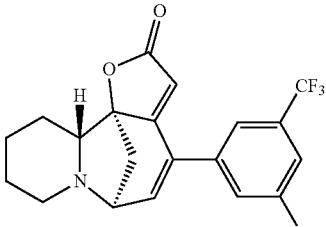

6

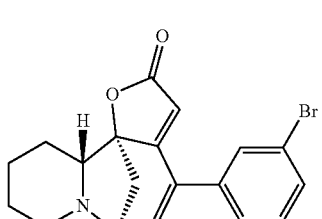

7 and pharmaceutically acceptable salts thereof.

5. The method of claim 1, wherein the securinine or norsecurinine analogue is selected from:

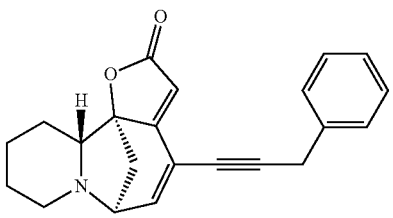

15

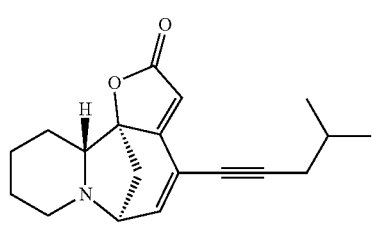

16

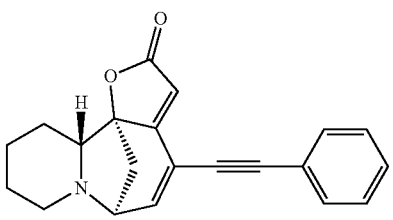

17

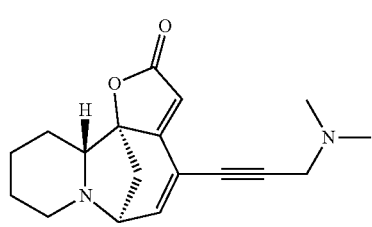

18

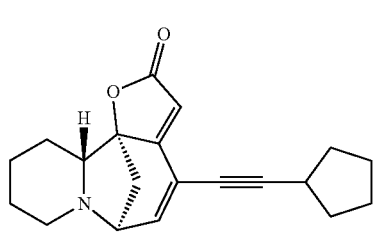

19

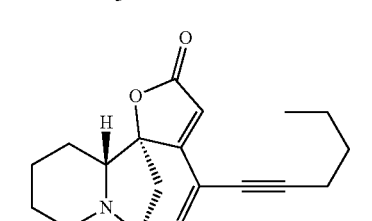

20

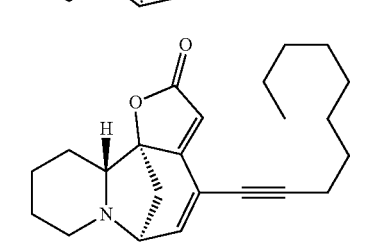

21

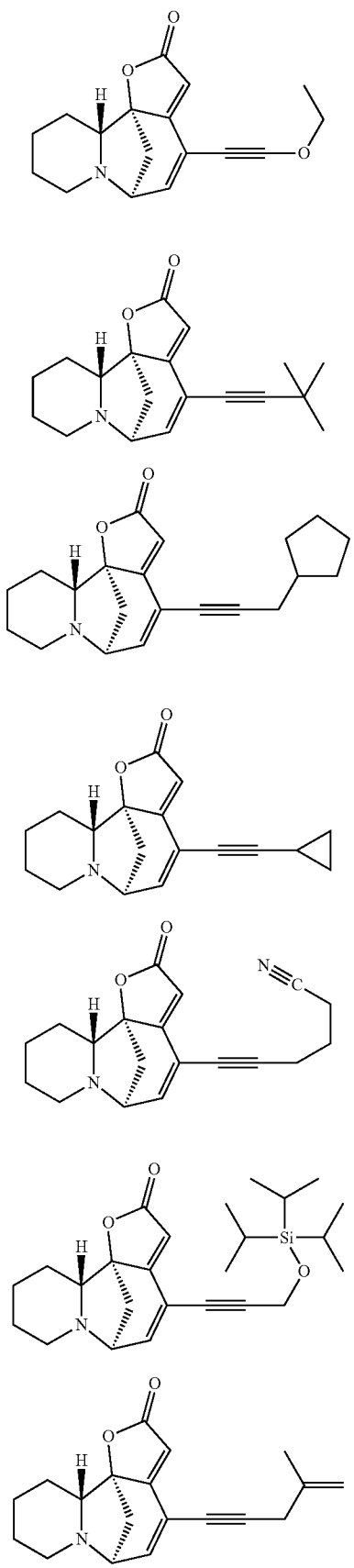
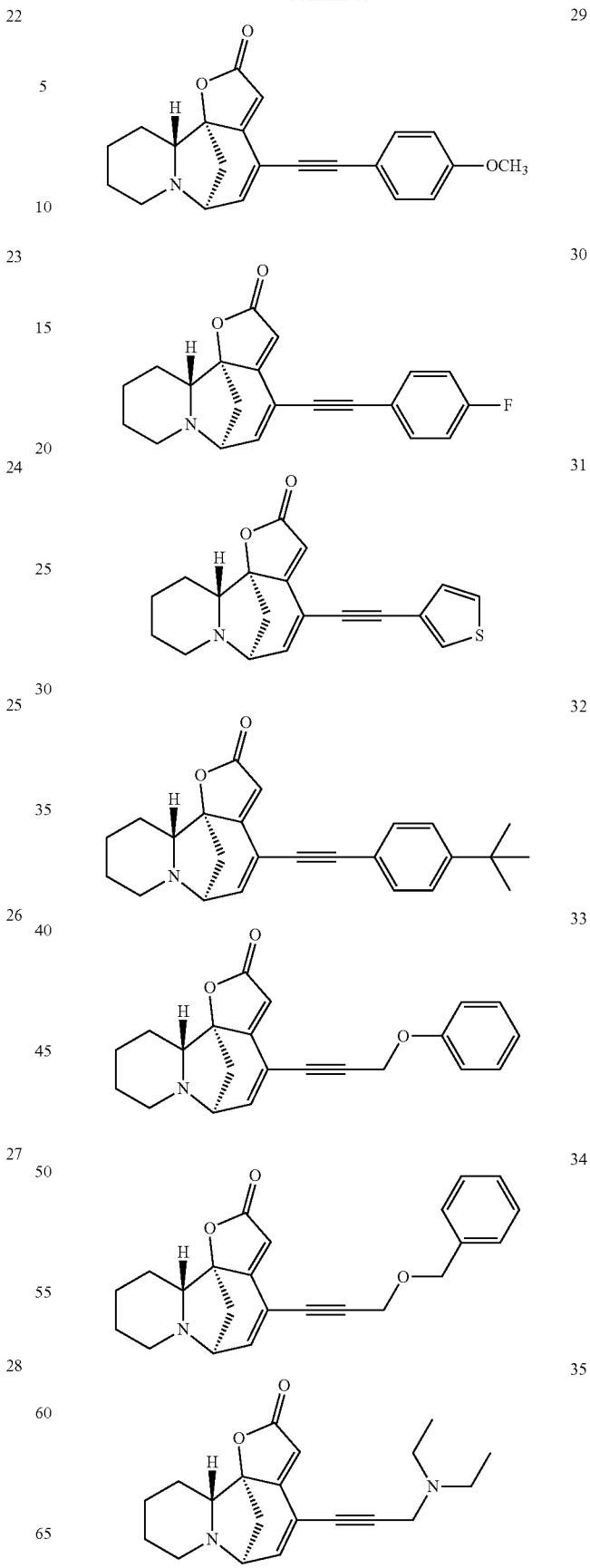

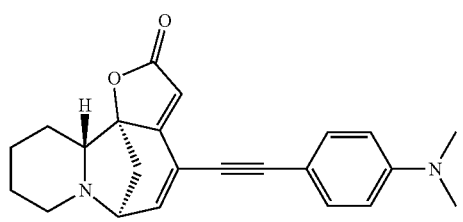
36
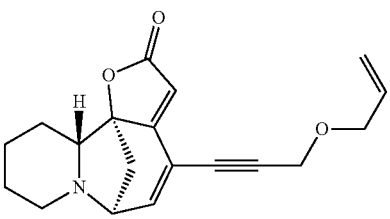
42
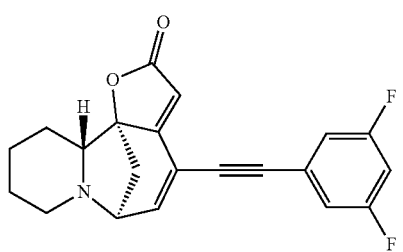
37
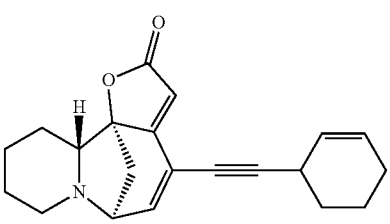
43
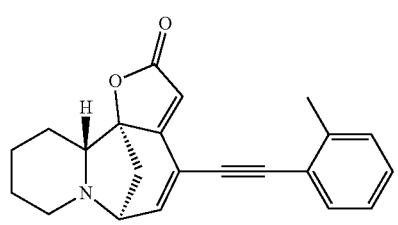
38
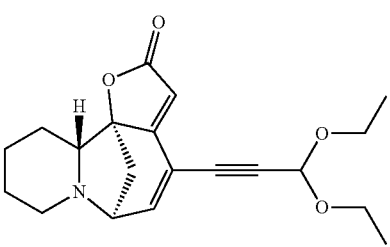
44
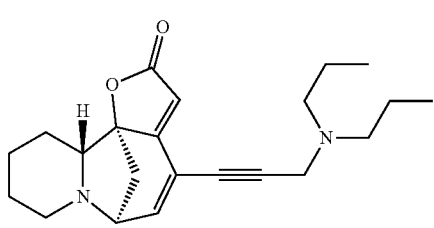
39
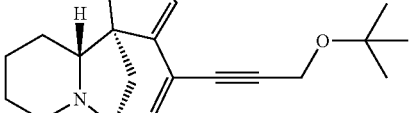
45
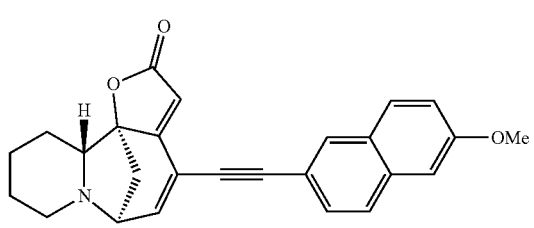
40
46
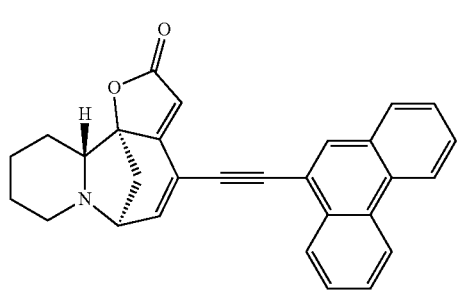
41
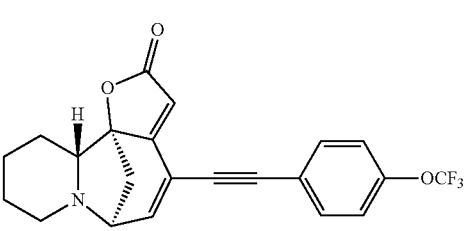
47
48

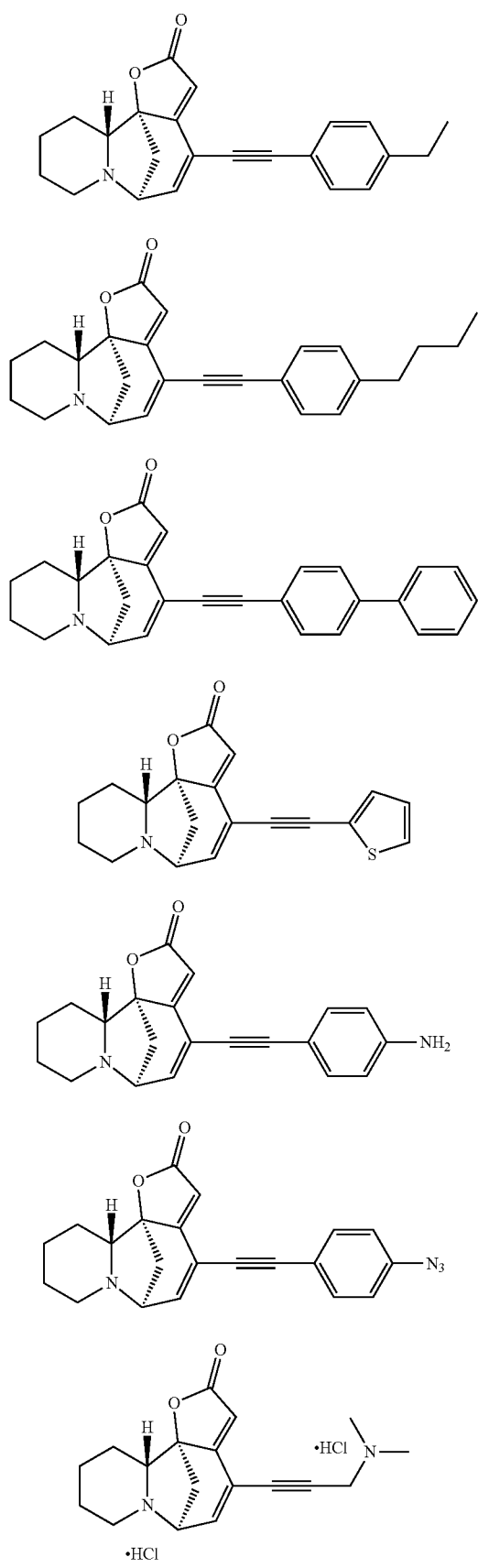
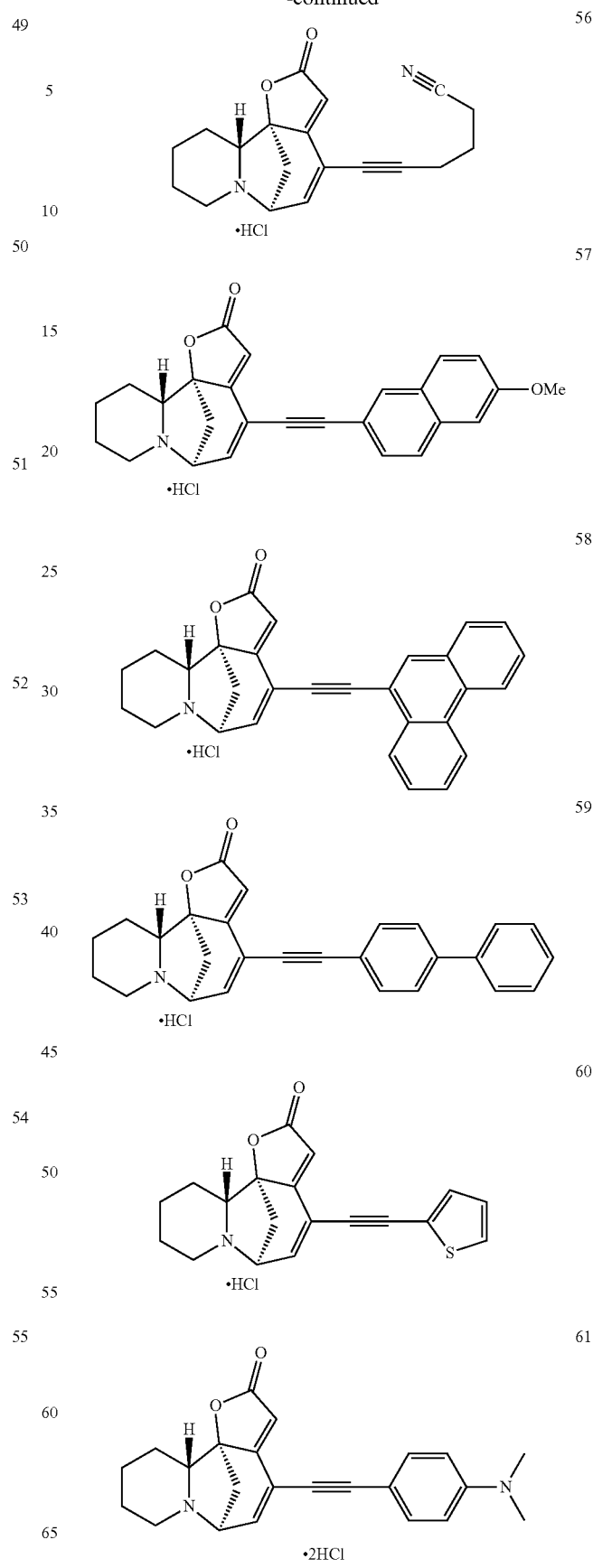

83 84
-continued   -continued
62   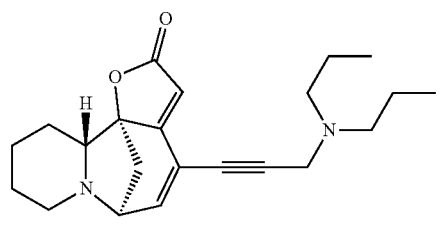
·2HCl
63   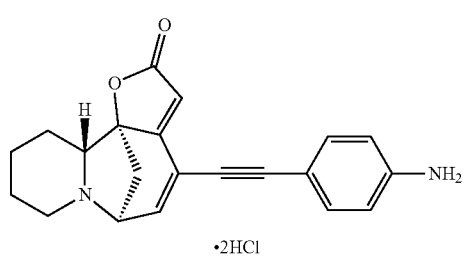
·2HCl
64   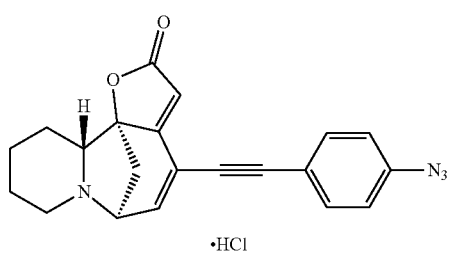
·HCl
101   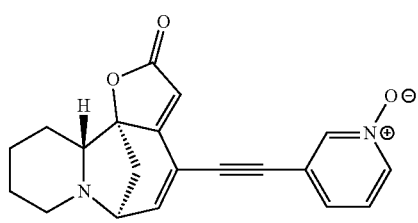
102   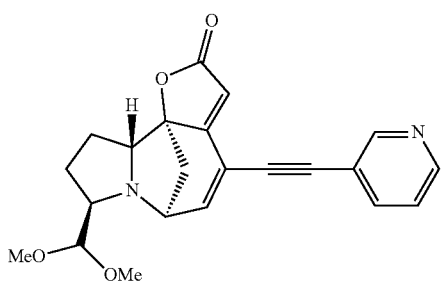
103   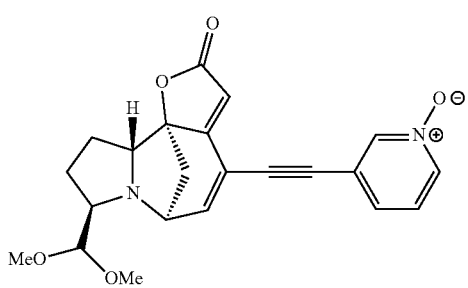
104   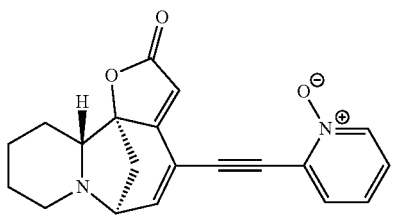
105   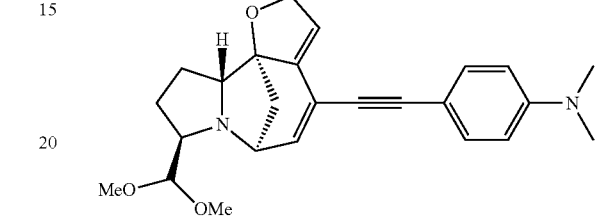
106   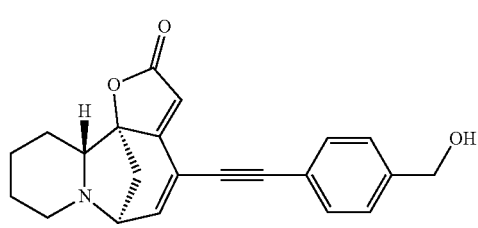
107   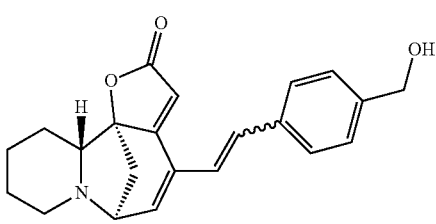
108   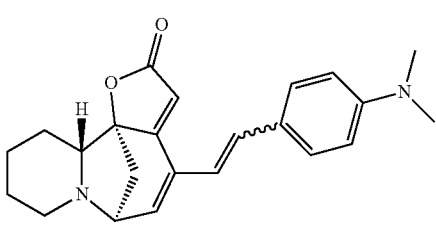
109   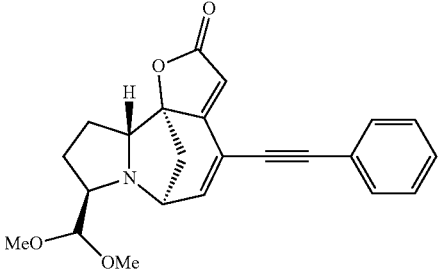

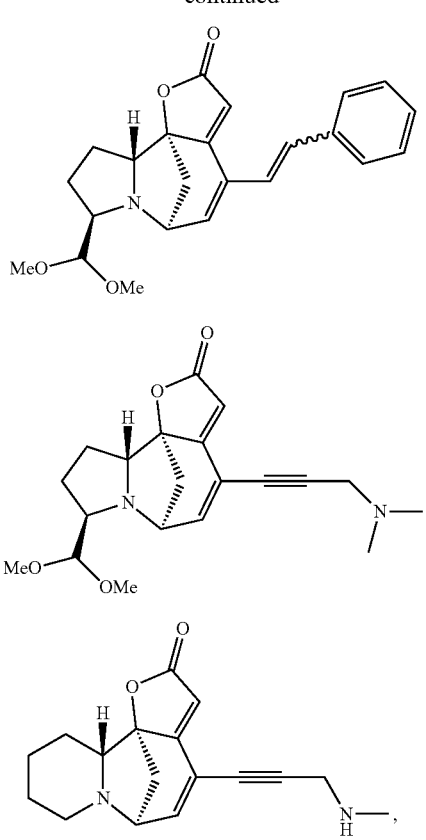

or pharmaceutically acceptable salts thereof.

6. The method of claim 1 further comprising: administering an anti-proliferative agent in combination with the securinine or norsecurinine analogue.

7. The method of claim 6, wherein the anti-proliferative agent is an anti-metabolite and/or a nucleoside analogue.

8. A method of inducing differentiation of a leukemia cell, comprising: administering to the leukemia cell an amount of at least one securinine or norsecurinine analogue compound selected from the group consisting of the following formula:

a. Formula I:

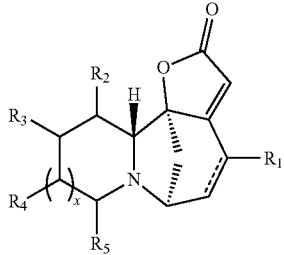

Formula (I)

or pharmaceutically acceptable salts thereof, wherein as valence and stability permit:
=== represents a single or double bond;
x is 0 or 1;
$R_1$ is hydrogen or substituted or unsubstituted alkyl, alkenyl, alkynyl, aryl, heteroaryl, cycloalkyl, heterocyclyl, cycloalkylalkyl, heterocyclylalkyl, heteroaralkyl, aralkyl, halo, silyl, hydroxyl, sulfhydryl, alkoxy, alkenyloxy, alkynyloxy, alkoxyalkyl, alkoxyalkenyl, aryloxy, acyl, alkylcarbonato, arylcarbonato, carboxy, carboxylato, carbamoyl, alkylcarbamoyl, arylcarbamoyl, thiocarbamoyl, carbamido, cyano, isocyano, cyanato, isocyanato, isothiocyanato, azido, formyl, thioformyl, amino, alkylamino, arylamino, cycloalkylamino, heterocyclylamino, cycloalkylalkylamino, arylalkylamino, heteroarylalkylamino, aminoalkyl, imino, nitro, nitroso, sulfo, sulfonato, alkylsulfanyl, arylsulfanyl, cycloalkylsulfanyl, heterocyclylsulfanyl, heteroarylsulfanyl, amidoalkylsulfanyl, arylalkysulfanyl, heteroarylalkylsulfanyl, alkylsulfinyl, arylsulfinyl, alkylsulfonyl, arylsulfonyl, phosphono, phosphonato, phosphinato, phospho, phosphino, thioalkyl, or thioaryl;

$R_2$, $R_3$, $R_4$, and $R_5$ are each independently hydrogen or substituted or unsubstituted alkyl, alkenyl, alkynyl, aryl, heteroaryl, cycloalkyl, heterocyclyl, cycloalkylalkyl, heterocyclylalkyl, heteroaralkyl, aralkyl, halo, silyl, hydroxyl, sulfhydryl, alkoxy, alkenyloxy, alkynyloxy, alkoxyalkyl, alkoxyalkenyl, aryloxy, acyl, alkylcarbonato, arylcarbonato, carboxy, carboxylato, carbamoyl, alkylcarbamoyl, arylcarbamoyl, thiocarbamoyl, carbamido, cyano, isocyano, cyanato, isocyanato, isothiocyanato, azido, formyl, thioformyl, amino, alkylamino, arylamino, cycloalkylamino, heterocyclylamino, cycloalkylalkylamino, arylalkylamino, heteroarylalkylamino, aminoalkyl, imino, nitro, nitroso, sulfo, sulfonato, alkylsulfanyl, arylsulfanyl, cycloalkylsulfanyl, heterocyclylsulfanyl, heteroarylsulfanyl, amidoalkylsulfanyl, arylalkysulfanyl, heteroarylalkylsulfanyl, alkylsulfinyl, arylsulfinyl, alkylsulfonyl, arylsulfonyl, phosphono, phosphonato, phosphinato, phospho, phosphino, thioalkyl, or thioaryl; and wherein adjacent R groups may be linked to form a cyclic or polycyclic ring, wherein the ring is a substituted or unsubstituted aryl, a substituted or unsubstituted heteroaryl, a substituted or unsubstituted cycloalkyl, or a substituted or unsubstituted heterocyclyl;

provided that when x is 1, at least one of $R_1$, $R_2$, $R_3$, $R_4$, and $R_5$ is other than hydrogen;

provided that when x is 0, === represents a double bond and $R_5$ is alkoxyalkyl;

b. Formula I':

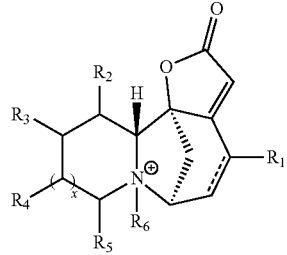

Formula (I')

or pharmaceutically acceptable salts thereof, wherein as valence and stability permit:
=== represents a single or double bond;
x is 0 or 1;
$R_1$ is hydrogen or substituted or unsubstituted alkyl, alkenyl, alkynyl, aryl, heteroaryl, cycloalkyl, heterocyclyl, cycloalkylalkyl, heterocyclylalkyl, heteroaralkyl, aralkyl, halo, silyl, hydroxyl, sulfhydryl, alkoxy, alkenyloxy, alkynyloxy, alkoxyalkyl, alkoxyalkenyl, aryloxy, acyl, alkylcarbonato, arylcarbonato, carboxy, carboxylato, carbamoyl, alkylcarbamoyl, arylcarbamoyl, thiocarbamoyl, carbamido, cyano, isocyano, cyanato, isocyanato, isothiocyanato, azido, formyl, thioformyl, amino, alkylamino, arylamino, cycloalkylamino, heterocyclylamino, cycloalkylalkylamino, arylalkylamino, heteroarylalkylamino, aminoalkyl, imino, nitro, nitroso, sulfo, sulfonato, alkylsulfanyl, arylsulfanyl, cycloalkylsulfanyl, heterocyclylsulfanyl, heteroarylsulfanyl, amidoalkylsulfanyl, arylalkysulfanyl, heteroarylalkylsulfanyl, alkylsulfinyl, arylsulfinyl, alkylsulfonyl, arylsulfonyl, phosphono, phosphonato, phosphinato, phospho, phosphino, thioalkyl, or thioaryl;

$R_2$, $R_3$, $R_4$, and $R_5$ are each independently hydrogen or substituted or unsubstituted alkyl, alkenyl, alkynyl, aryl, heteroaryl, cycloalkyl, heterocyclyl, cycloalkyl alkyl, heterocyclylalkyl, heteroaralkyl, aralkyl, halo, silyl, hydroxyl, sulfhydryl, alkoxy, alkenyloxy, alkynyloxy, alkoxyalkyl, alkoxyalkenyl, aryloxy, acyl, alkylcarbonato, arylcarbonato, carboxy, carboxylato, carbamoyl, alkylcarbamoyl, arylcarbamoyl, thiocarbamoyl, carbamido, cyano, isocyano, cyanato, isocyanato, isothiocyanato, azido, formyl, thioformyl, amino, alkylamino, arylamino, cycloalkylamino, heterocyclylamino, cycloalkylalkylamino, arylalkylamino, heteroarylalkylamino, aminoalkyl, imino, nitro, nitroso, sulfo, sulfonato, alkylsulfanyl, arylsulfanyl, cycloalkylsulfanyl, heterocyclylsulfanyl, heteroarylsulfanyl, amidoalkylsulfanyl, arylalkysulfanyl, heteroarylalkylsulfanyl, alkylsulfinyl, arylsulfinyl, alkylsulfonyl, arylsulfonyl, phosphono, phosphonato, phosphinato, phospho, phosphino, thioalkyl, or thioaryl;

wherein adjacent R groups may be linked to form a cyclic or polycyclic ring, wherein the ring is a substituted or unsubstituted aryl, a substituted or unsubstituted heteroaryl, a substituted or unsubstituted cycloalkyl, or a substituted or unsubstituted heterocyclyl; and wherein $R_6$ is $C_1$-$C_6$ alkyl;

provided that when x is 1, at least one of $R_1$, $R_2$, $R_3$, $R_4$, and $R_5$ is other than hydrogen;

c. Formula (II):

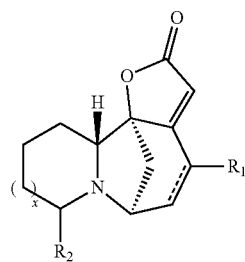

Formula (II)

or pharmaceutically acceptable salts thereof, wherein as valence and stability permit:
=== represents a single or double bond;
x is 0 or 1;
$R_1$ is hydrogen or substituted or unsubstituted alkyl, alkenyl, alkynyl, aryl, heteroaryl, cycloalkyl, heterocyclyl, cycloalkylalkyl, heterocyclylalkyl, heteroaralkyl, aralkyl, halo, silyl, hydroxyl, sulfhydryl, alkoxy, alkenyloxy, alkynyloxy, alkoxyalkyl, alkoxyalkenyl, aryloxy, acyl, alkylcarbonato, arylcarbonato, carboxy, carboxylato, carbamoyl, alkylcarbamoyl, arylcarbamoyl, thiocarbamoyl, carbamido, cyano, isocyano, cyanato, isocyanato, isothiocyanato, azido, formyl, thioformyl, amino, alkylamino, arylamino, cycloalkylamino, heterocyclylamino, cycloalkylalkylamino, arylalkylamino, heteroarylalkylamino, aminoalkyl, imino, nitro, nitroso, sulfo, sulfonato, alkylsulfanyl, arylsulfanyl, cycloalkylsulfanyl, heterocyclylsulfanyl, heteroarylsulfanyl, amidoalkylsulfanyl, arylalkysulfanyl, heteroarylalkylsulfanyl, alkylsulfinyl, arylsulfinyl, alkylsulfonyl, arylsulfonyl, phosphono, phosphonato, phosphinato, phospho, phosphino, thioalkyl, or thioaryl; and $R_2$ is hydrogen or substituted or unsubstituted alkyl, alkenyl, alkynyl, aryl, heteroaryl, cycloalkyl, heterocyclyl, cycloalkylalkyl, heterocyclylalkyl, heteroaralkyl, aralkyl, halo, silyl, hydroxyl, sulfhydryl, alkoxy, alkenyloxy, alkynyloxy, alkoxyalkyl, alkoxyalkenyl, aryloxy, acyl, alkylcarbonato, arylcarbonato, carboxy, carboxylato, carbamoyl, alkylcarbamoyl, arylcarbamoyl, thiocarbamoyl, carbamido, cyano, isocyano, cyanato, isocyanato, isothiocyanato, azido, formyl, thioformyl, amino, alkylamino, arylamino, cycloalkylamino, heterocyclylamino, cycloalkylalkylamino, arylalkylamino, heteroarylalkylamino, aminoalkyl, imino, nitro, nitroso, sulfo, sulfonato, alkylsulfanyl, arylsulfanyl, cycloalkylsulfanyl, heterocyclylsulfanyl, heteroarylsulfanyl, amidoalkylsulfanyl, arylalkysulfanyl, heteroarylalkylsulfanyl, alkylsulfinyl, arylsulfinyl, alkylsulfonyl, arylsulfonyl, phosphono, phosphonato, phosphinato, phospho, phosphino, thioalkyl, or thioaryl;

provided that when x is 1, at least one of $R_1$ or $R_2$ is other than hydrogen;

provided that when x is 0, === represents a double bond and $R_2$ is alkoxyalkyl;

d. Formula (III):

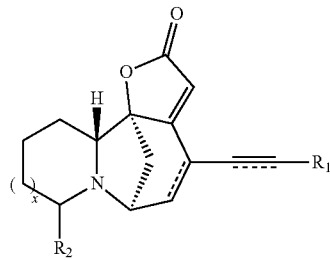

Formula (III)

or pharmaceutically acceptable salts thereof, wherein as valence and stability permit:
=== represents a single or double bond;
≡≡≡ represents a double or triple bond;
x is 0 or 1;
$R_1$ is hydrogen or substituted or unsubstituted alkyl, alkenyl, alkynyl, aryl, heteroaryl, cycloalkyl, heterocyclyl, cycloalkylalkyl, heterocyclylalkyl, heteroaralkyl, aralkyl, halo, silyl, hydroxyl, sulfhydryl, alkoxy, alkenyloxy, alkynyloxy, alkoxyalkyl, alkoxyalkenyl, aryloxy, acyl, alkylcarbonato, arylcarbonato, carboxy, carboxylato, carbamoyl, alkylcarbamoyl, arylcarbamoyl, thiocarbamoyl, carbamido, cyano, isocyano, cyanato, isocyanato, isothiocyanato, azido, formyl, thioformyl, amino, alkylamino, arylamino, cycloalkylamino, heterocyclylamino, cycloalkylalkylamino, arylalkylamino, heteroarylalkylamino, aminoalkyl, imino, nitro, nitroso, sulfo, sulfonato, alkylsulfanyl, arylsulfanyl, cycloalkylsulfanyl, heterocyclylsulfanyl, heteroarylsulfanyl, amidoalkylsulfanyl, arylalkysulfanyl, heteroarylalkylsulfanyl, alkylsulfinyl, arylsulfinyl, alkylsulfonyl, arylsulfonyl, phosphono, phosphonato, phosphinato, phospho, phosphino, thioalkyl, or thioaryl; and $R_2$ is hydrogen or substituted or unsubstituted alkyl, alkenyl, alkynyl, aryl, heteroaryl, cycloalkyl, heterocyclyl, cycloalkylalkyl, heterocyclylalkyl, heteroaralkyl, aralkyl, halo, silyl, hydroxyl, sulfhydryl, alkoxy, alkenyloxy, alkynyloxy, alkoxyalkyl, alkoxyalkenyl, aryloxy, acyl, alkylcarbonato, arylcarbonato, carboxy, carboxylato, carbamoyl, alkylcarbamoyl, arylcarbamoyl, thiocarbamoyl, carbamido, cyano, isocyano, cyanato, isocyanato, isothiocyanato, azido, formyl, thioformyl, amino, alkylamino, arylamino, cycloalkylamino, heterocyclylamino, cycloalkylalkylamino, arylalkylamino, heteroarylalkylamino, aminoalkyl, imino, nitro, nitroso, sulfo, sulfonato, alkylsulfanyl, arylsulfanyl, cycloalkylsulfanyl, heterocyclylsulfanyl, heteroarylsulfanyl, amidoalkylsulfanyl, arylalkysulfanyl, heteroarylalkylsulfanyl, alkylsulfinyl, arylsulfinyl, alkylsulfonyl, arylsulfonyl, phosphono, phosphonato, phosphinato, phospho, phosphino, thioalkyl, or thioaryl;

e. formula (IV):

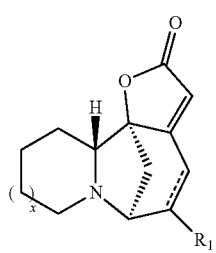

Formula IV or pharmaceutically acceptable salts thereof, wherein as valence and stability permit:
=== represents a single or double bond;
x is 0 or 1; and
$R_1$ is substituted or unsubstituted alkyl, alkenyl, alkynyl, aryl, heteroaryl, cycloalkyl, heterocyclyl, cycloalkylalkyl, heterocyclylalkyl, heteroaralkyl, aralkyl, halo, silyl, hydroxyl, sulfhydryl, alkoxy, alkenyloxy, alkynyloxy, alkoxyalkyl, alkoxyalkenyl, aryloxy, acyl, alkylcarbonato, arylcarbonato, carboxy, carboxylato, carbamoyl, alkylcarbamoyl, arylcarbamoyl, thiocarbamoyl, carbamido, cyano, isocyano, cyanato, isocyanato, isothiocyanato, azido, formyl, thioformyl, amino, alkylamino, arylamino, cycloalkylamino, heterocyclylamino, cycloalkylalkylamino, arylalkylamino, heteroarylalkylamino, aminoalkyl, imino, nitro, nitroso, sulfo, sulfonato, alkylsulfanyl, arylsulfanyl, cycloalkylsulfanyl, heterocyclylsulfanyl, heteroarylsulfanyl, amidoalkylsulfanyl, arylalkysulfanyl, heteroarylalkylsulfanyl, alkylsulfinyl, arylsulfinyl, alkylsulfonyl, arylsulfonyl, phosphono, phosphonato, phosphinato, phospho, phosphino, thioalkyl, or thioaryl;

provided that wherein $R_1$ is substituted or unsubstituted heterocyclyl, $R_1$ is not mono-fluoro substituted pyrrolidine, x is 1, and === represents a single bond;

provided that wherein $R_1$ is substituted or unsubstituted heteroarylalkylamino, $R_1$ is not indolealkylamino, x is 1, and === represents a single bond;

provided that wherein $R_1$ is substituted or unsubstituted arylsulfanyl, $R_1$ is not phenylsulfanyl, x is 1, and === represents a single bond; and provided that wherein $R_1$ is alkylsulfanyl, $R_1$ is not propylsulfanyl, x is 1, and === represents a single bond; and f. formula (IV'):

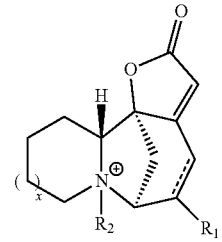

Formula IV' or pharmaceutically acceptable salts thereof, wherein as valence and stability permit:
=== represents a single or double bond;
x is 0 or 1;
$R_1$ is hydrogen or substituted or unsubstituted alkyl, alkenyl, alkynyl, aryl, heteroaryl, cycloalkyl, heterocyclyl, cycloalkylalkyl, heterocyclylalkyl, heteroaralkyl, aralkyl, halo, silyl, hydroxyl, sulfhydryl, alkoxy, alkenyloxy, alkynyloxy, alkoxyalkyl, alkoxyalkenyl, aryloxy, acyl, alkylcarbonato, arylcarbonato, carboxy, carboxylato, carbamoyl, alkylcarbamoyl, arylcarbamoyl, thiocarbamoyl, carbamido, cyano, isocyano, cyanato, isocyanato, isothiocyanato, azido, formyl, thioformyl, amino, alkylamino, arylamino, cycloalkylamino, heterocyclylamino, cycloalkylalkylamino, arylalkylamino, heteroarylalkylamino, aminoalkyl, imino, nitro, nitroso, sulfo, sulfonato, alkylsulfanyl, arylsulfanyl, cycloalkylsulfanyl, heterocyclylsulfanyl, heteroarylsulfanyl, amidoalkylsulfanyl, arylalkysulfanyl, heteroarylalkylsulfanyl, alkylsulfinyl, arylsulfinyl, alkylsulfonyl, arylsulfonyl, phosphono, phosphonato, phosphinato, phospho, phosphino, thioalkyl, or thioaryl; and wherein $R_2$ is $C_1$-$C_6$ alkyl;

provided that wherein $R_1$ is substituted or unsubstituted heterocyclyl, $R_1$ is not mono-fluoro substituted pyrrolidine, x is 1, and === represents a single bond;

provided that wherein $R_1$ is substituted or unsubstituted heteroarylalkylamino, $R_1$ is not indolealkylamino, x is 1, and === represents a single bond;

provided that wherein $R_1$ is substituted or unsubstituted arylsulfanyl, $R_1$ is not phenylsulfanyl, x is 1, and === represents a single bond; and provided that wherein $R_1$ is alkylsulfanyl, $R_1$ is not propylsulfanyl, x is 1, and === represents a single bond.

9. The method of claim 8, wherein the securinine or norsecurinine analogue is selected from:

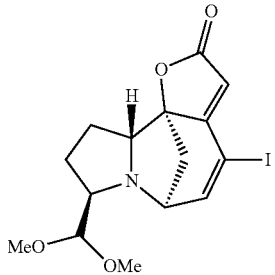

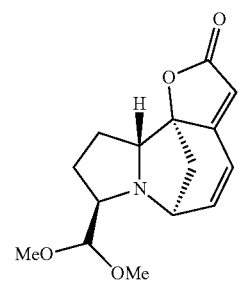

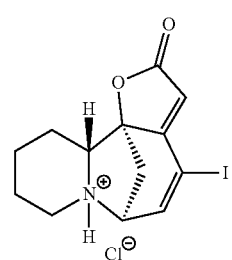

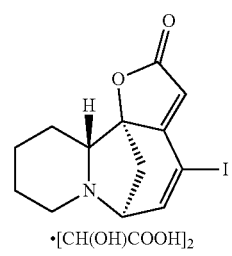

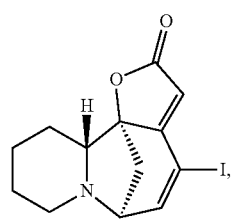

or pharmaceutically acceptable salts thereof.

10. The method of claim 8, wherein the securinine or norsecurinine analogue is selected from:

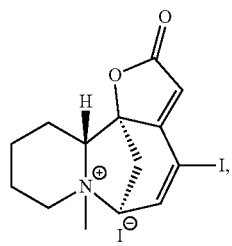

and pharmaceutically acceptable salts thereof.

11. The method of claim 8, wherein the securinine or norsecurinine analogue is selected from:

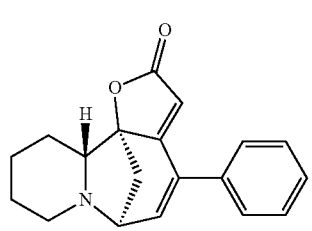

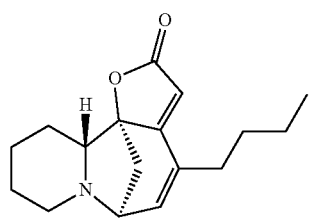

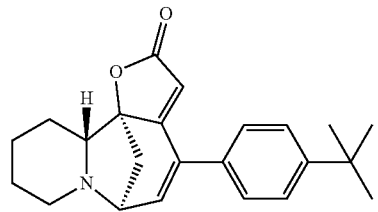

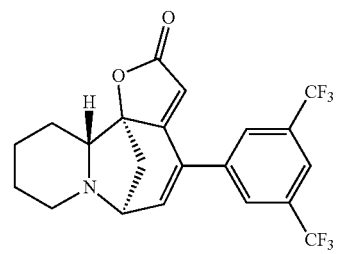

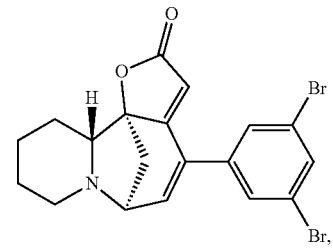

and pharmaceutically acceptable salts thereof.

12. The method of claim 8, wherein the securinine or norsecurinine analogue is selected from:
15
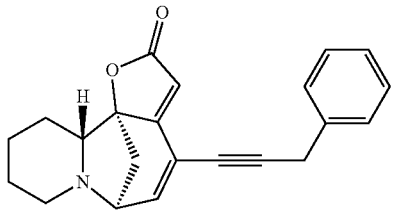
16
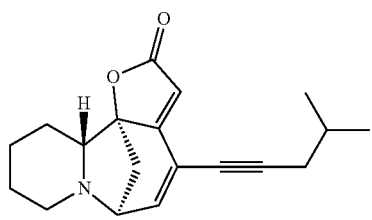
17
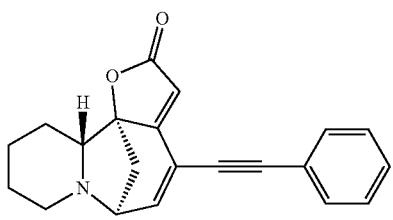
18
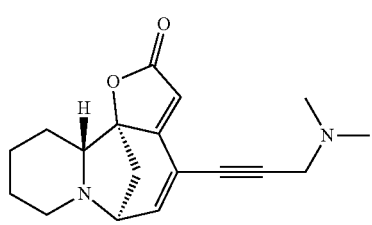
19
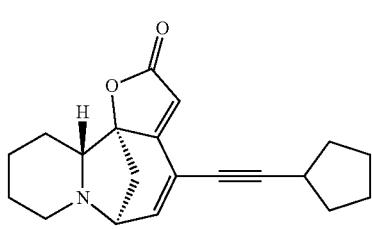
20
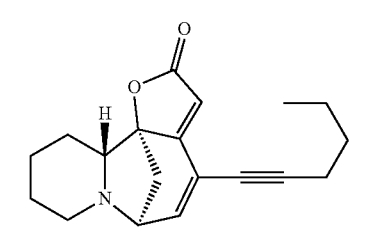
21
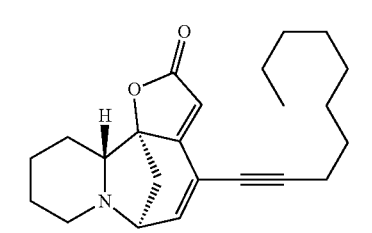
22
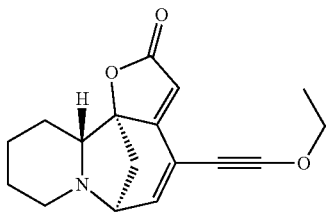
23
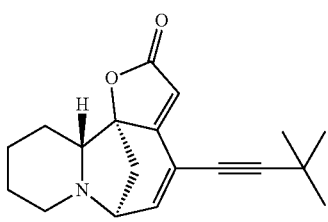
24
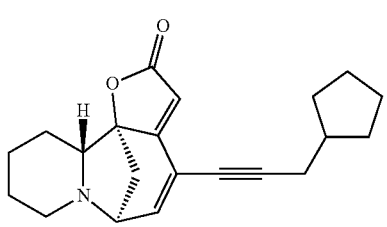
25
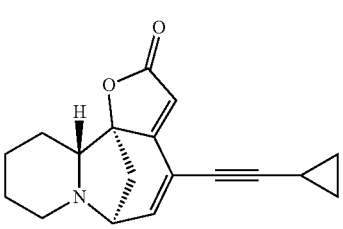
26
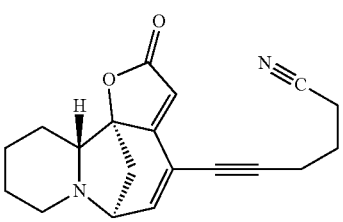
27
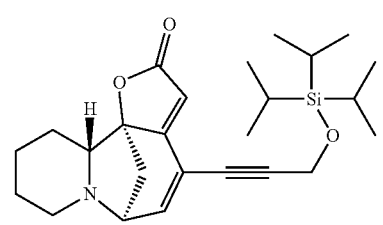
28
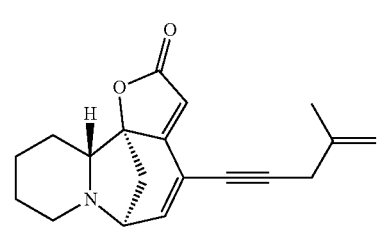

29
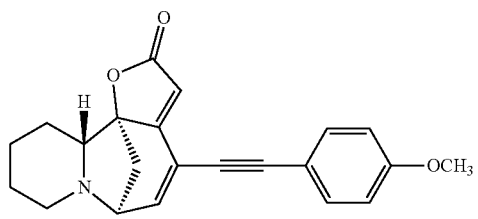
30
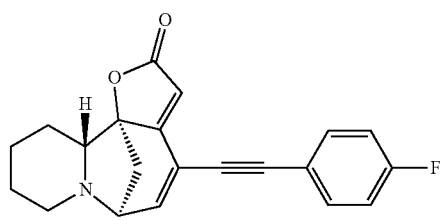
31
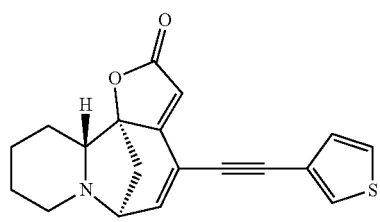
32
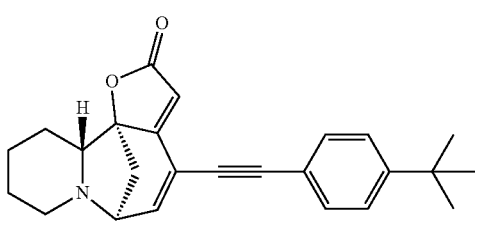
33
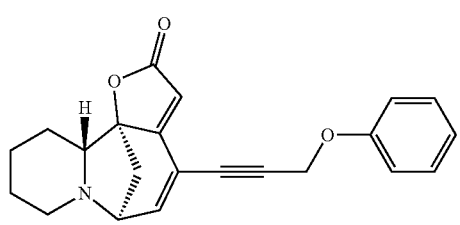
34
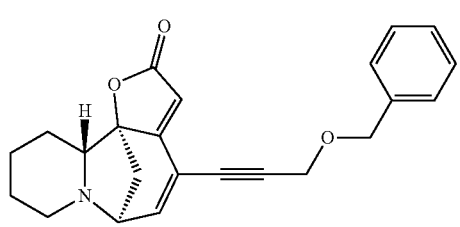
35
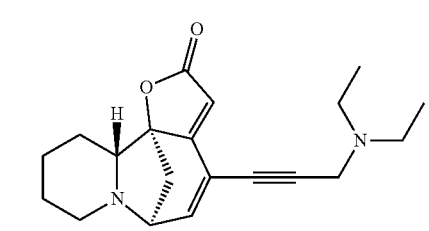
36
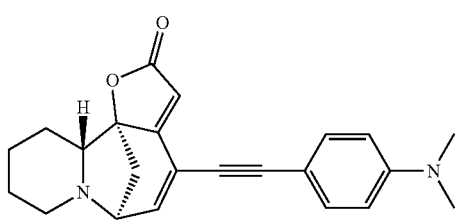
37
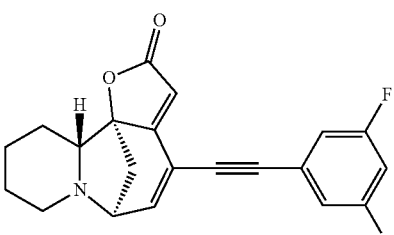
38
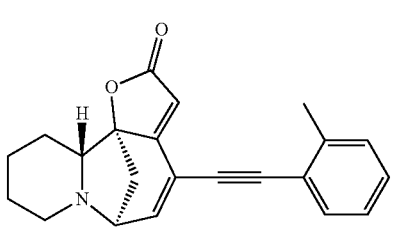
39
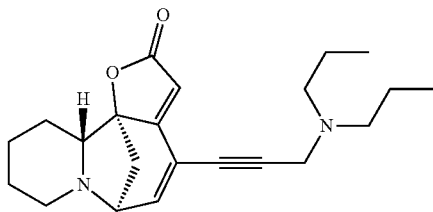
40
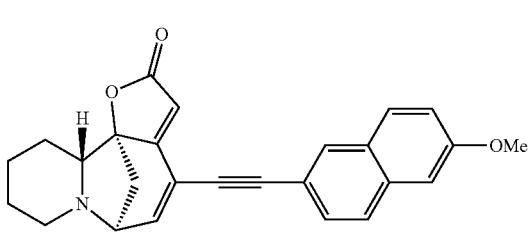
41
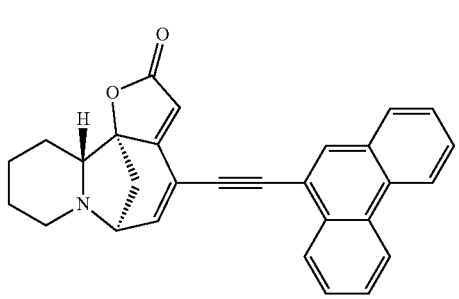

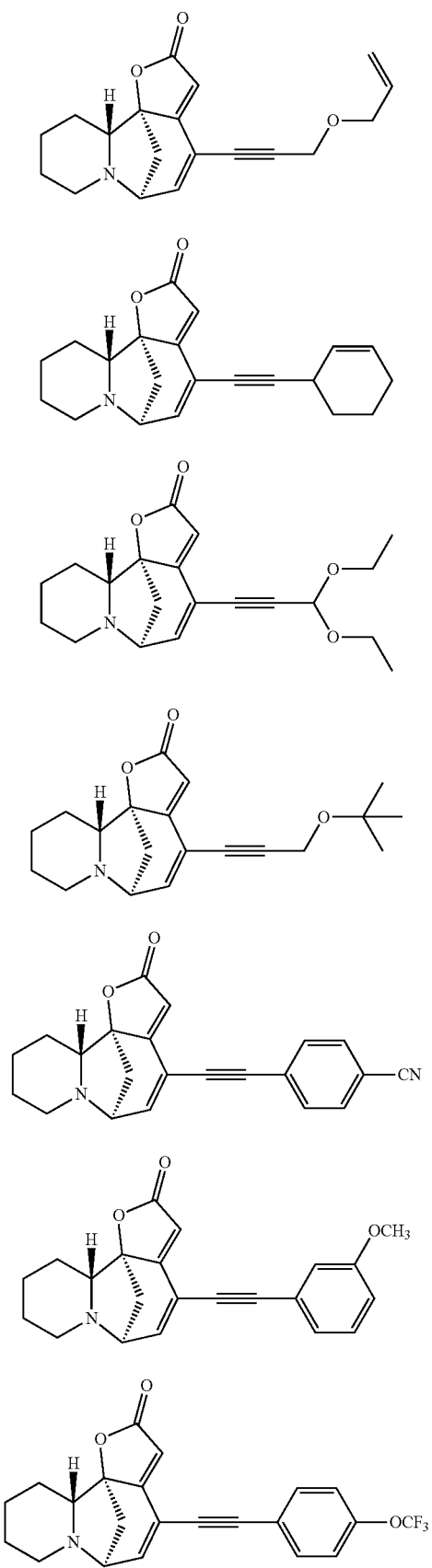
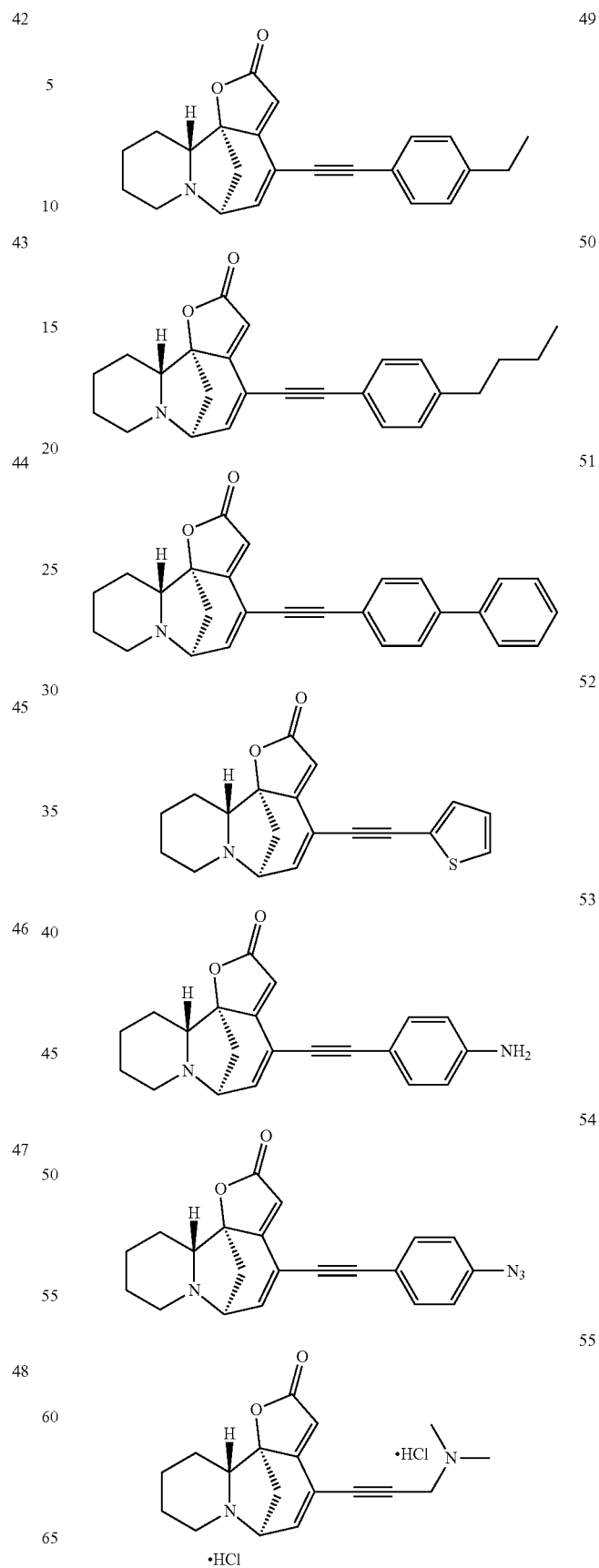

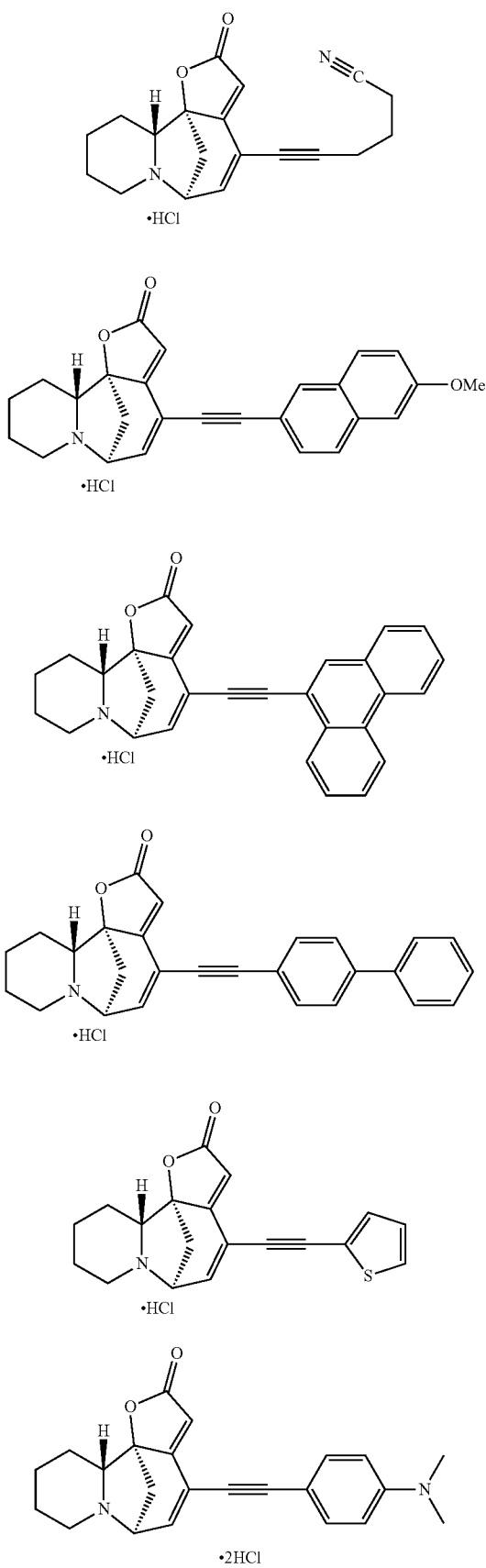
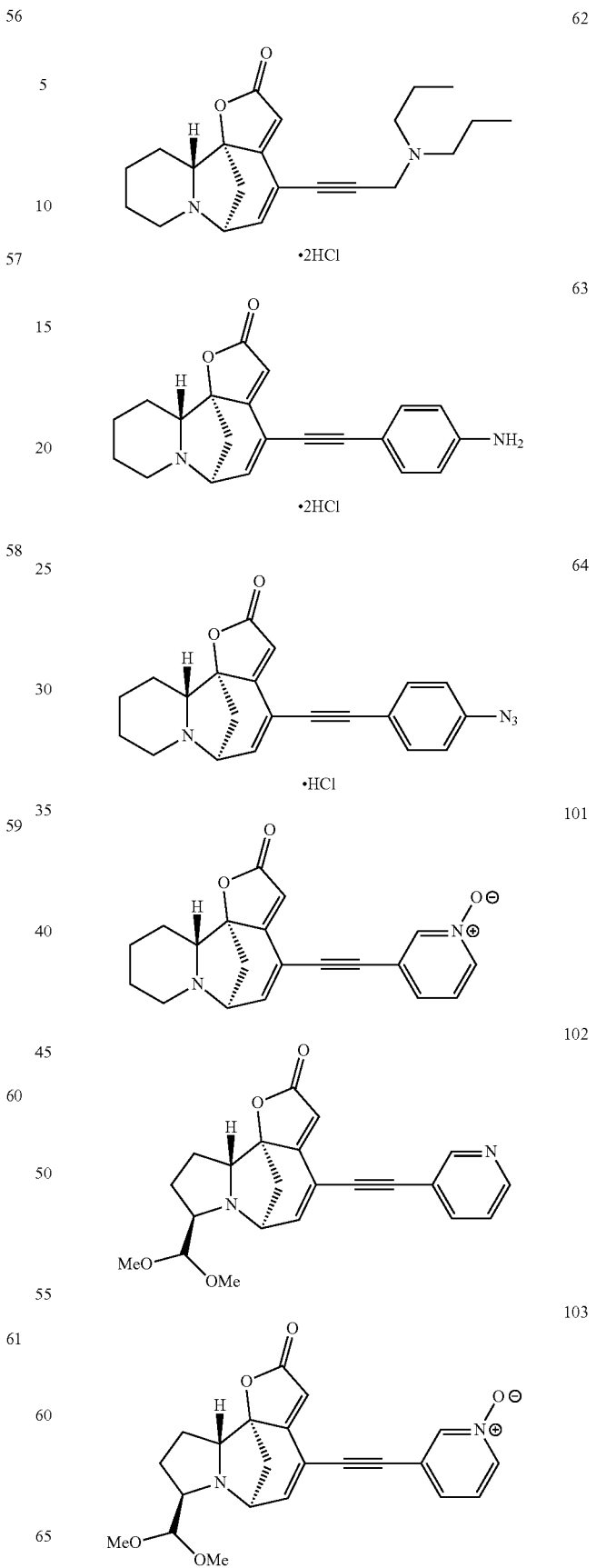

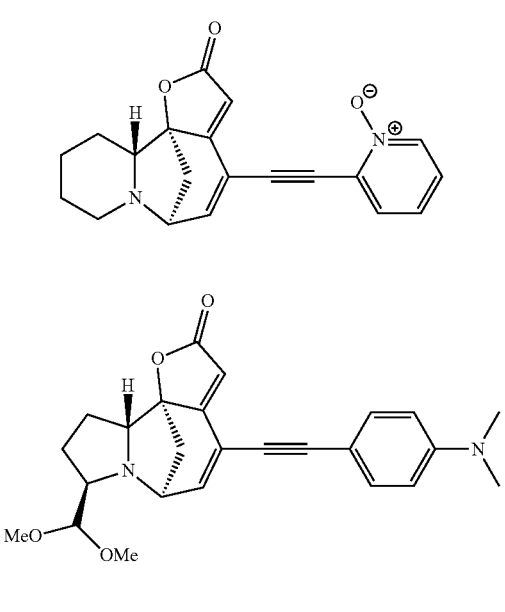

or pharmaceutically acceptable salts thereof.

13. The method of claim 8, further comprising: administering an anti-proliferative agent in combination with the securinine or norsecurinine analogue.

14. The method of claim 8, wherein the anti-proliferative agent is an anti-metabolite and/or a nucleoside analogue.

15. The method of claim 1, wherein the securinine or norsecurinine analogue is selected from:

-continued
67
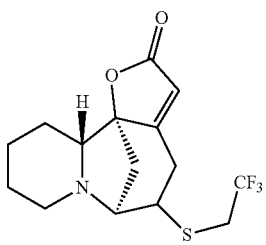
68
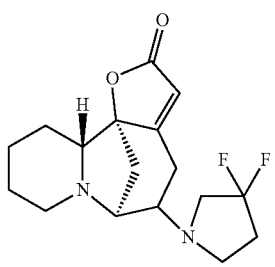
69
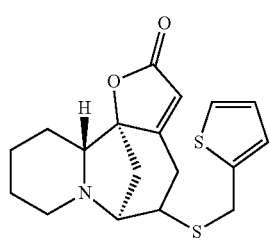
70
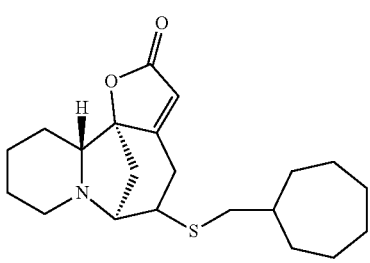
71
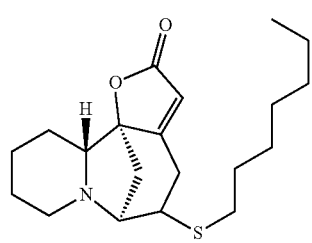
72
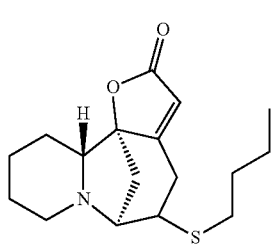
-continued
73
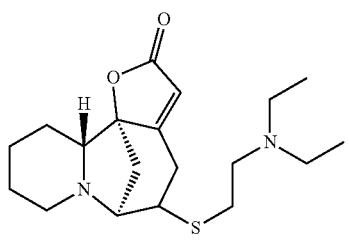
75
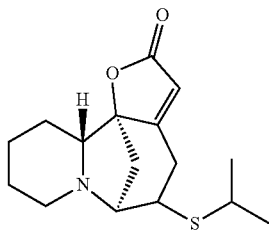
76
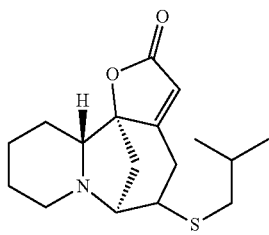
77
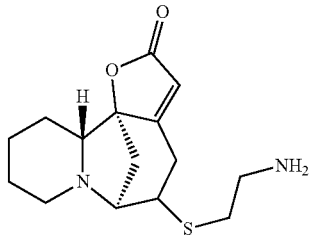
78
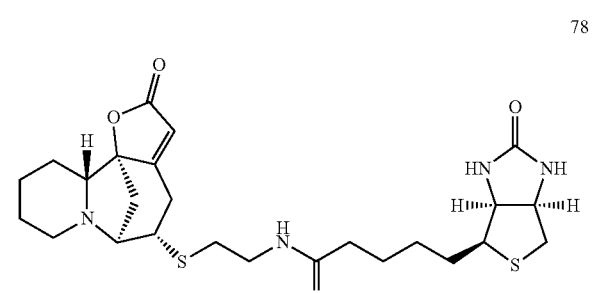
79
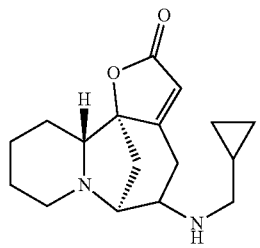

93 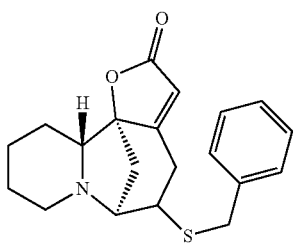
94 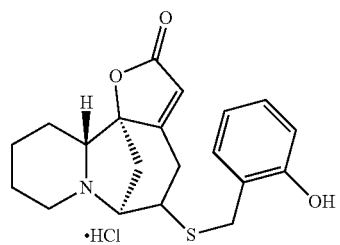
95 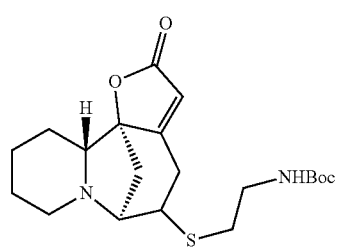
96 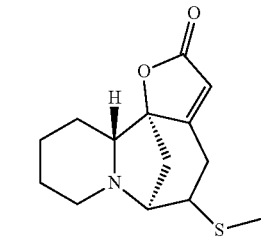
97 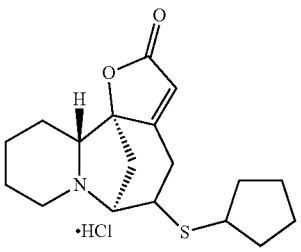
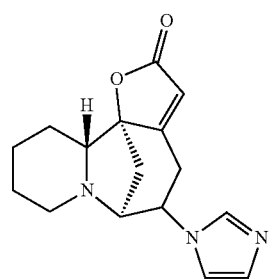
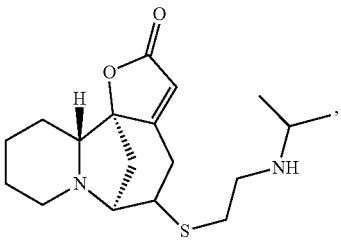
or pharmaceutically acceptable salts thereof.
16. The method of claim 8, wherein the securinine or norsecurinine analogue is selected from:
65 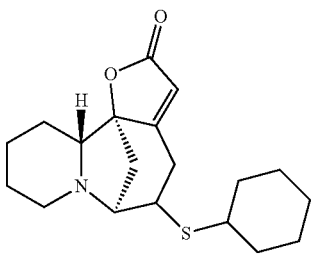
66 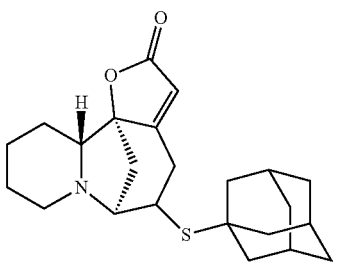
67 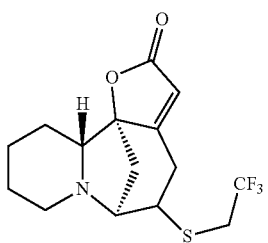
68 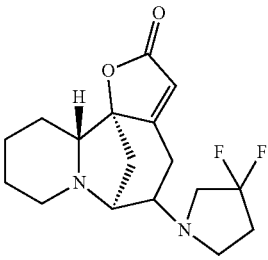
69 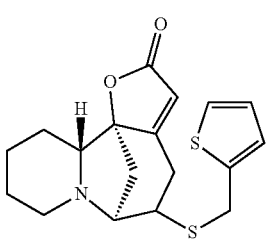

109  
-continued
70
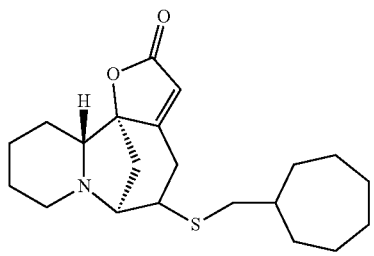
71
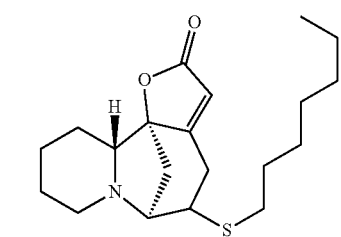
72
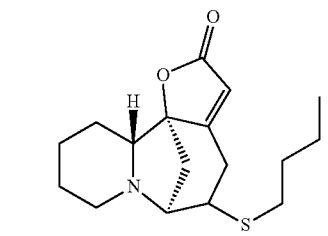
73
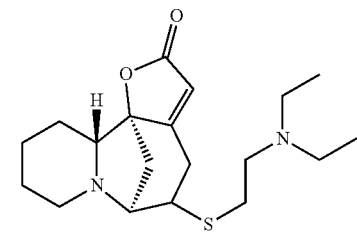
74
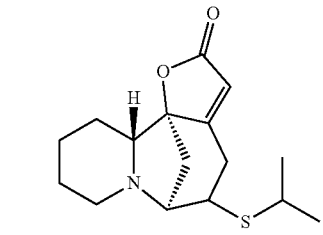
75
76
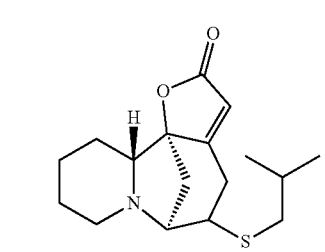
110  
-continued
77
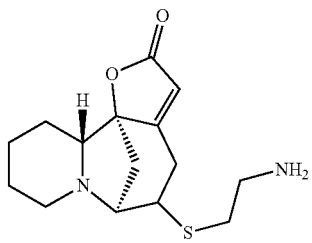
78
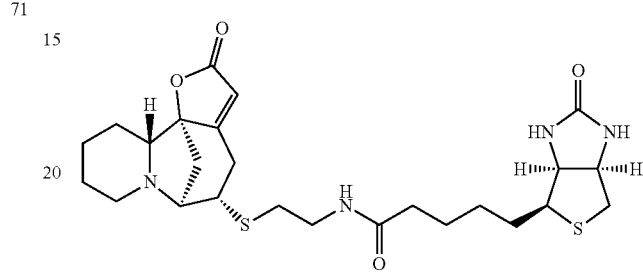
79
80
81
82

83
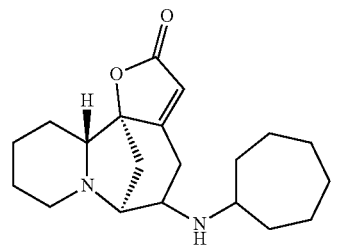
84
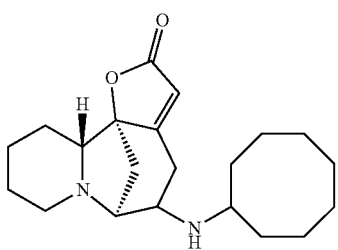
85
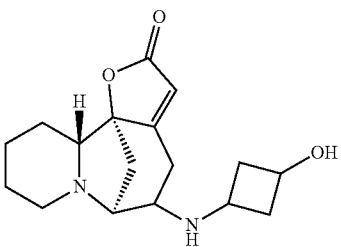
86
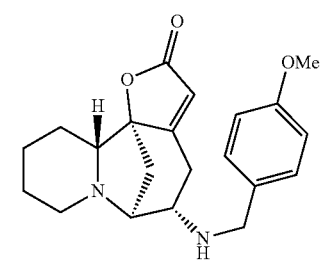
87
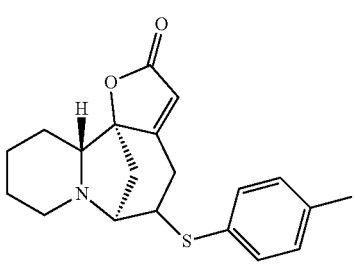
88
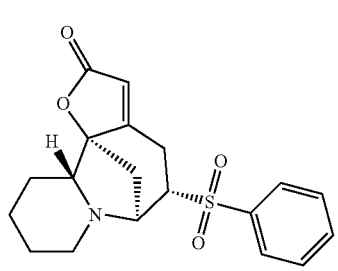
90
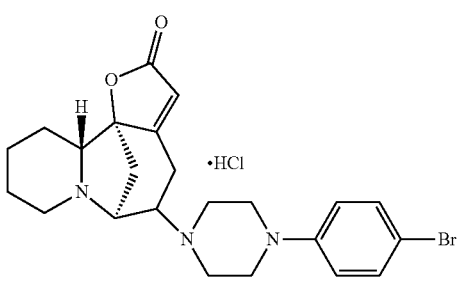
91
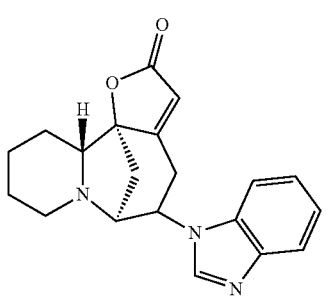
92
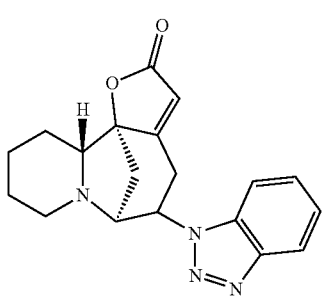
93
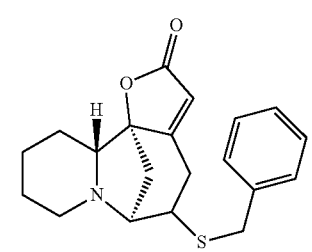
94
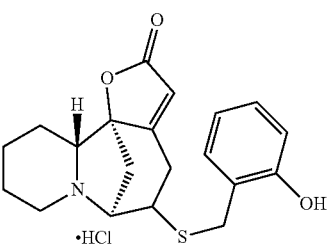

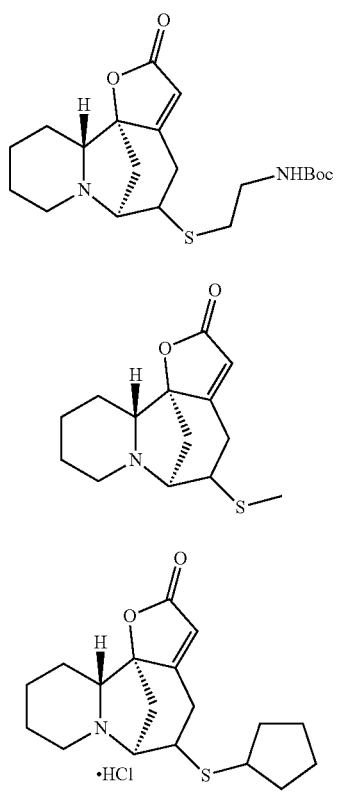

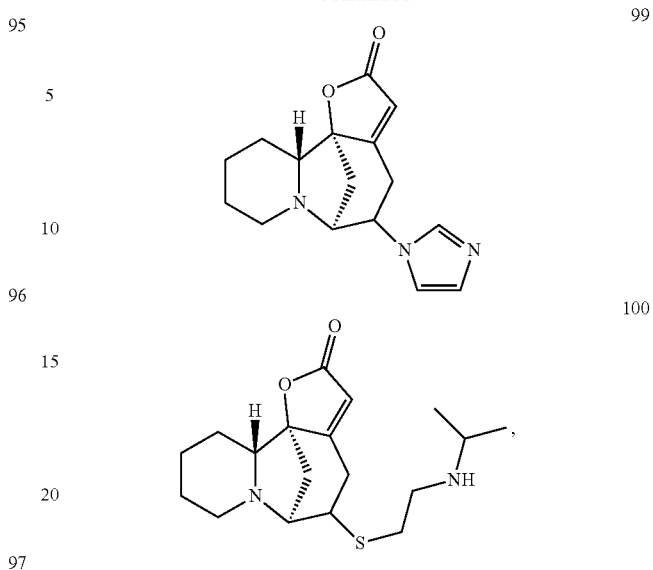

or pharmaceutically acceptable salts thereof.

17. The method of claim 8, wherein the cell is in a subject, and the subject has a myeloid disorder.

18. The method of claim 6, wherein the anti-proliferative agent is selected from the group consisting of: an alkylating agent, an antibiotic-type agent, a hormonal anticancer agent, an immunological agent, an interferon-type agent, and an antineoplastic agent.

* * * * *